United States Patent [19]

Takiguchi et al.

[11] Patent Number: 5,091,109
[45] Date of Patent: Feb. 25, 1992

[54] MESOMORPHIC COMPOUND, LIQUID CRYSTAL COMPOSITION CONTAINING SAME AND LIQUID CRYSTAL DEVICE USING SAME

[75] Inventors: Takao Takiguchi, Tokyo; Takashi Iwaki, Isehara; Takeshi Togano, Yokohama; Yoko Yamada, Atsugi; Shosei Mori, Atsugi; Shinichi Nakamura, Atsugi, all of Japan

[73] Assignee: Canon Kabushiki Kaisha, Tokyo, Japan

[21] Appl. No.: 564,077

[22] Filed: Aug. 8, 1990

[30] Foreign Application Priority Data

Aug. 25, 1989 [JP] Japan .................. 1-219768

[51] Int. Cl.$^5$ .................. C09K 19/34; C07D 85/14; G02F 1/13
[52] U.S. Cl. .................. 252/299.61; 252/299.01; 548/136; 359/104
[58] Field of Search .................. 252/299.01, 299.61, 252/299.62, 299.63, 299.5, 299.67; 350/350 S, 350 R; 548/136, 128

[56] References Cited

U.S. PATENT DOCUMENTS 4,367,924 1/1983 Clark et al. .................. 350/350 S

FOREIGN PATENT DOCUMENTS 107216 8/1981 Japan .
193426 11/1984 Japan .
193427 11/1984 Japan .

(List continued on next page.)

OTHER PUBLICATIONS

CA: 69002y, "2,5 diaryl-1,3.4 thiadiazyoles", vol. 68, 1968, p. 69002, author: Siegenrist.

(List continued on next page.)

Primary Examiner—John S. Maples
Assistant Examiner—Shean C. Wu
Attorney, Agent, or Firm—Fitzpatrick, Cella, Harper & Scinto

[57] ABSTRACT

A mesomorphic compound represented by the following formula (I):

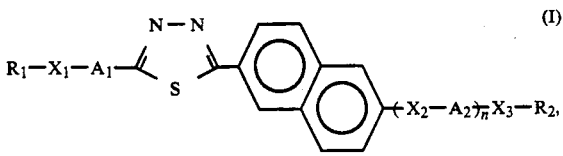

wherein $R_1$ and $R_2$ respectively denote an alkyl group having 1-16 carbon atoms capable of having a substituent; $X_1$, $X_2$ and $X_3$ respectively denote a single bond, —O—,

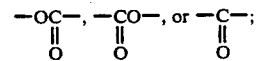

$A_1$ and $A_2$ respectively

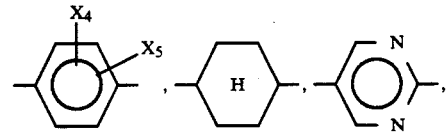

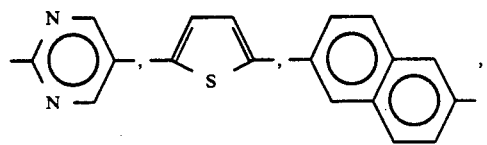

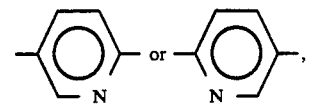

wherein $X_4$ and $X_5$ respectively denote hydrogen, fluorine, chlorine, bromine, —CH$_3$, —CN or —CF$_3$ with proviso that $X_1$ always denotes a single bond when $A_1$ denotes a single bond; and n is 0 or 1.

189 Claims, 2 Drawing Sheets

FOREIGN PATENT DOCUMENTS

| | | |
|---|---|---|
| 156046 | 8/1985 | Japan . |
| 156047 | 8/1985 | Japan . |
| 245142 | 10/1986 | Japan . |
| 242724 | 11/1986 | Japan . |
| 246722 | 11/1986 | Japan . |
| 246723 | 11/1986 | Japan . |
| 249024 | 11/1986 | Japan . |
| 249025 | 11/1986 | Japan . |
| 051644 | 3/1987 | Japan . |
| 045258 | 2/1988 | Japan . |
| 222148 | 9/1988 | Japan . |
| 061472 | 3/1989 | Japan . |
| 2-1482 | 1/1990 | Japan . |
| 0808019 | 10/1988 | World Int. Prop. O. . |

OTHER PUBLICATIONS

CA: 94: 174933g, "Liquid crystalline, 1,3.4 thiadiazoles," Hauschild et al., vol. 94, 1981, p. 174993-4 (American Chemical Society).

Helv. Chim. Acta., vol. 39, No. 59 (1956) 504:13.

Helv. Chim. Acta., vol. 40, No. 249 (1957) 2428:33.

Appl. Phys. Lett., vol. 18, No. 4 (Feb. 1971) 127:28.

R. Tschesche and W. Fuhrer. Chem. Ber., vol. III (1978) 3502:05.

P. B. Rasmussen et al., Bull. Soc. Chim. de France, No. 1 (1985) 62:65.

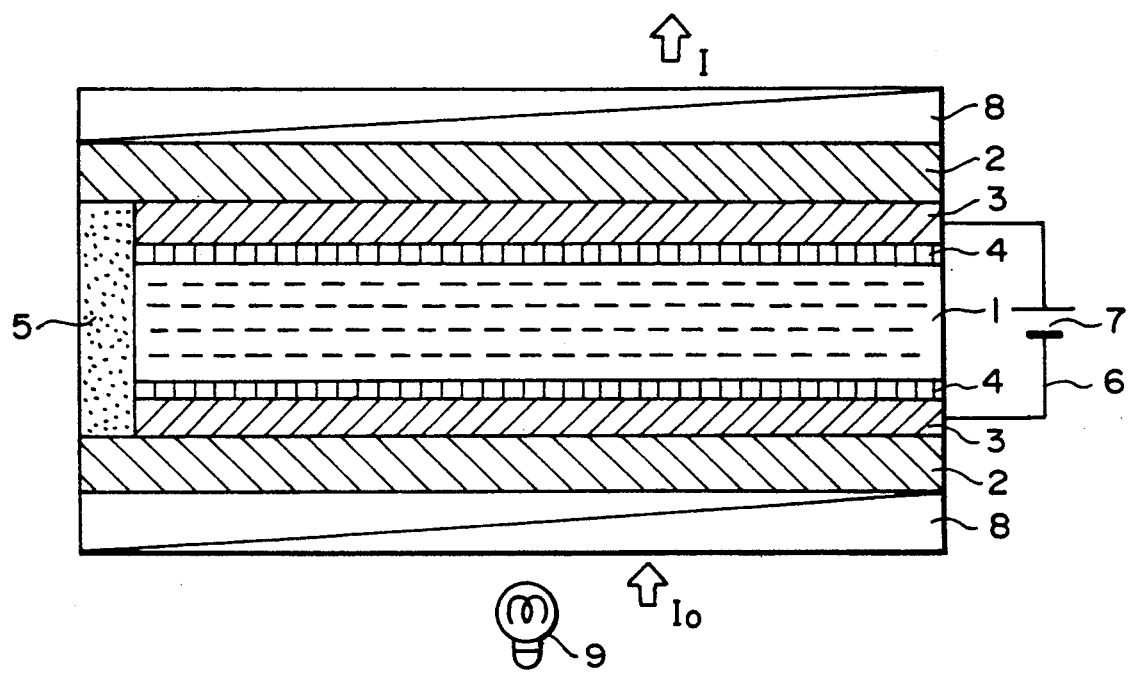
F I G. 1

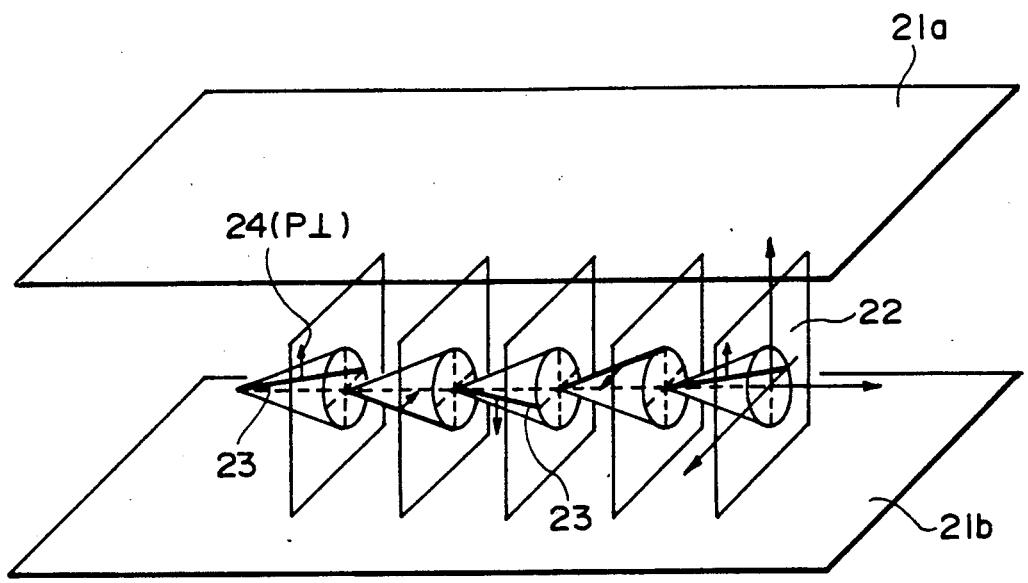
F I G. 2
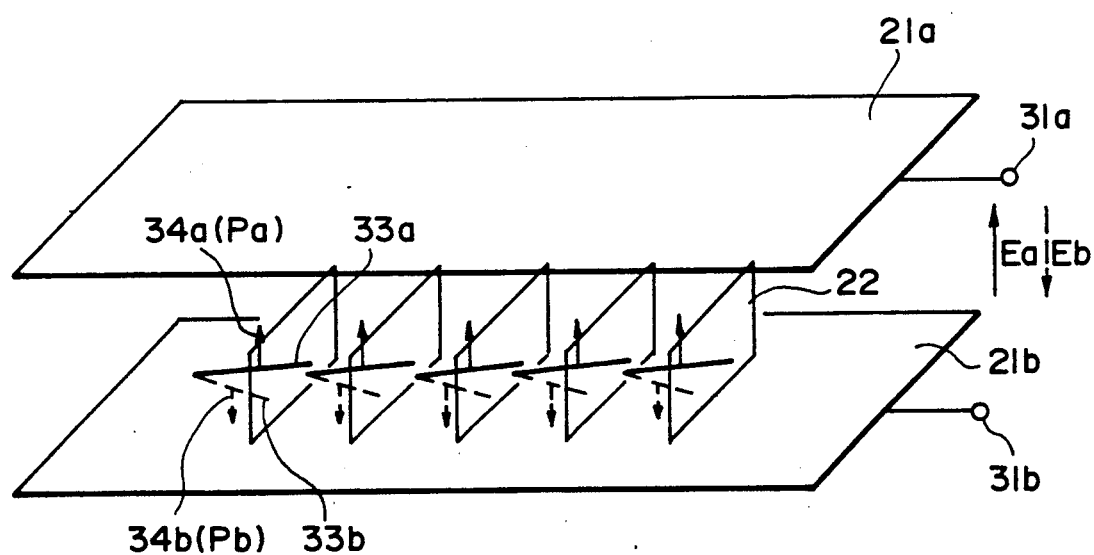
F I G. 3

MESOMORPHIC COMPOUND, LIQUID CRYSTAL COMPOSITION CONTAINING SAME AND LIQUID CRYSTAL DEVICE USING SAME

FIELD OF THE INVENTION AND RELATED ART

The present invention relates to a novel mesomorphic compound, a liquid crystal composition containing the compound and liquid crystal device using the composition, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127-128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and are vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density with respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second optically stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric field and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°-40 °C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

In a representative FLC cell structure, a pair of substrates are disposed, each substrate of e.g. glass being provided with an electrode pattern of e.g. ITO, further thereon with a layer of e.g. SiO$_2$ (about 1000 Å) for preventing short circuit between the pair of substrates and further thereon with a film of e.g. polyimide (PI; such as SP-510, 710, ... available from Toray K.K.) of about 400 Å in thickness, which is then treated for alignment control by rubbing with e.g. an acetate fiber-planted cloth. Such a pair of substrates are disposed opposite to each other so that their alignment control directions are symmetrical and the spacing between the substrates is held at 1-3 microns.

On the other hand, it is known that the ferroelectric liquid crystal molecules under such non-helical conditions are disposed in succession so that their directors (longer molecular axes) are gradually twisted between the substrates and do not show a uniaxial orientation or alignment (i.e., in a splay alignment state). A problem in this case is a low transmittance through the liquid crystal layer.

Transmitted light intensity I through a liquid crystal is given by the following equation with respect to the incident light intensity $I_0$ under cross nicols when the uniaxial alignment of the molecules is assumed:

$$I = I_0 \sin^2(4\theta a) \sin^2(\pi n d/\lambda) \qquad (1),$$

wherein $\Delta n$ denotes the refractive index anisotropy of the FLC; d, the cell thickness; $\lambda$, the wavelength of the incident light; and $\theta a$, a half of the angle between two stable states (tilt angle).

When a conventional FLC cell is used, it has been experimentally known that $\theta a$ is 5-8 degrees under a twisted alignment condition. The control of physical properties affecting the term $\Delta n d \pi/\lambda$ cannot be easily performed, so that it is desired to increase $\theta a$ to increase I. However, this has not been successfully accomplished by only a static alignment technique.

With respect to such a problem, it has been proposed to utilize a torque relating to a dielectric anisotropy $\Delta \epsilon$ of an FLC (1983 SID report from AT & T; Japanese Laid-Open Patent Applns. 245142/1986, 246722/1986, 246723/1986, 246724/1986, 249024/1986 and 249025/1986). More specifically, a liquid crystal molecule having a negative $\Delta \epsilon$ tends to become parallel to the substrates under application of an electric field. By utilizing this property, if an effective value of AC electric field is applied even in a period other than switching, the above-mentioned twisted alignment is removed, so that $\theta a$ is increased to provide an increased transmittance (AC stabilization effect).

SUMMARY OF THE INVENTION

An object of the present invention is to provide a novel mesomorphic compound, a liquid crystal composition with improved responsiveness containing the mesomorphic compound for providing a practical ferroelectric liquid crystal device, and a liquid crystal device using the liquid crystal composition.

Another object of the present invention is to provide a liquid crystal device using a liquid crystal composition containing a novel mesomorphic compound and showing improved display characteristics due to AC stabilization effect.

According to the present invention, there is provided a mesomorphic compound represented by the following formula (I):

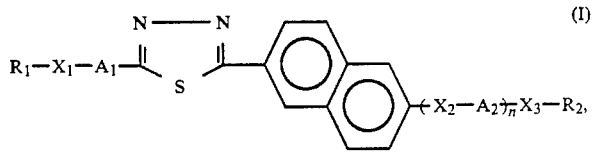

wherein $R_1$ and $R_2$ respectively denote an alkyl group having 1-16 carbon atoms capable of having a substituent; $X_1$, $X_2$ and $X_3$ respectively denote a single bond, —O—,

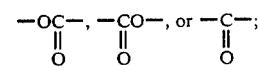

$A_1$ and $A_2$ respectively denote

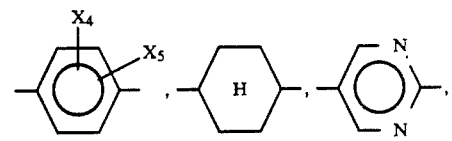

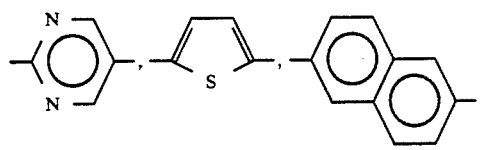

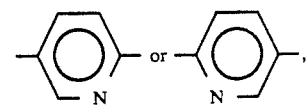

wherein $X_4$ and $X_5$ respectively denote hydrogen, fluorine, chlorine, bromine, —CH$_3$, —CN or —CF$_3$ with proviso that $X_1$ always denotes a single bond when $A_1$ denotes a single bond; and n is 0 or 1.

According to the present invention, there is further provided a liquid crystal composition containing at least one species of the mesomorphic compound as described above.

The present invention further provides a liquid crystal device comprising a pair of substrates and such a liquid crystal composition as described above disposed between the electrode plates.

Heretofore, mesomorphic compounds having thiadiazole rings have been shown in D. Demus et al., "Flüssige Kristalle in Tabellen II", pp. 359-361 (1984), and disclosed in Japanese Laid-Open Patent Applications (KOKAI) Nos. 51644/1987, 222148/1988 and 61472/1989 and W088/08019. With respect to a thiadiazole derivative having a naphthalene ring represented by the above formula (I) of the present invention, there is no suggestion except for W088/08019. Although W088/08019 discloses a broad general formula which can encompass the above thiadiazole derivative in its claim, there is no disclosure of a specific embodiment corresponding to the above formula (I) of the present invention. We found that the thiadiazole derivative having the naphthalene ring represented by the formula (I) had a wide temperature range of a mesomorphic phase (particularly a smectic C (SmC) phase) compared with the conventional thiadiazole derivatives. We also found that a liquid crystal device using a ferroelectric chiral smectic liquid crystal composition containing the above thiadiazole derivative of the invention showed an improved low-temperature operation characteristic, a decreased temperature-dependence of response speed, and an improved display characteristic when used in a driving method utilizing AC stabilization.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1 is a schematic sectional view of a liquid crystal display device using a ferroelectric liquid crystal; and FIGS. 2 and 3 are schematic perspective views of a device cell embodiment for illustrating the operation principle of a ferroelectric liquid crystal device.

DETAILED DESCRIPTION OF THE INVENTION

In the formula (I) as described above, preferred examples of $X_1$, $X_2$ and $X_3$ may respectively include the following combinations:

$X_1$ is a single bond, —O—, or

$X_2$ is a single bond, —O—,

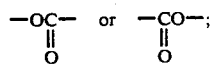

and
$X_3$ is a single bond, —O—,

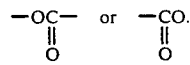

Further, preferred examples of $R_1$ and $R_2$ in the formula (I) may respectively include the following groups (i) to (iv):

(i) n-alkyl group having 1-16 carbon atoms, particularly having 3-12 carbon atoms;

(ii)

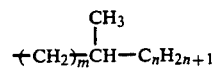

wherein m is an integer of 1-6 and n is an integer of 2-8 (optically active or inactive);

(iii)

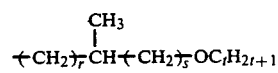

wherein r is an integer of 0-6, s is 0 or 1 and t is an integer of 1-12 (optically active or inactive); and (iv)

wherein m is 0 or 1 and x is an integer of 1-14.

Herein, * denotes an optically active center.

Further, preferred examples of $A_1$ and $A_2$ may respectively include the following combinations:

$A_1$ is

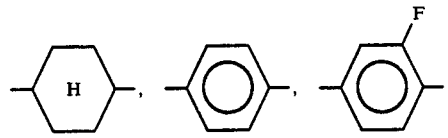

or a single bond, particularly

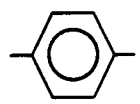

or a single bond; $A_2$ is

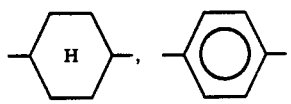

or a single bond, particularly a single bond.

The compounds represented by the general formula (I) may be synthesized through the following reaction schemes A and B.

REACTION SCHEME A

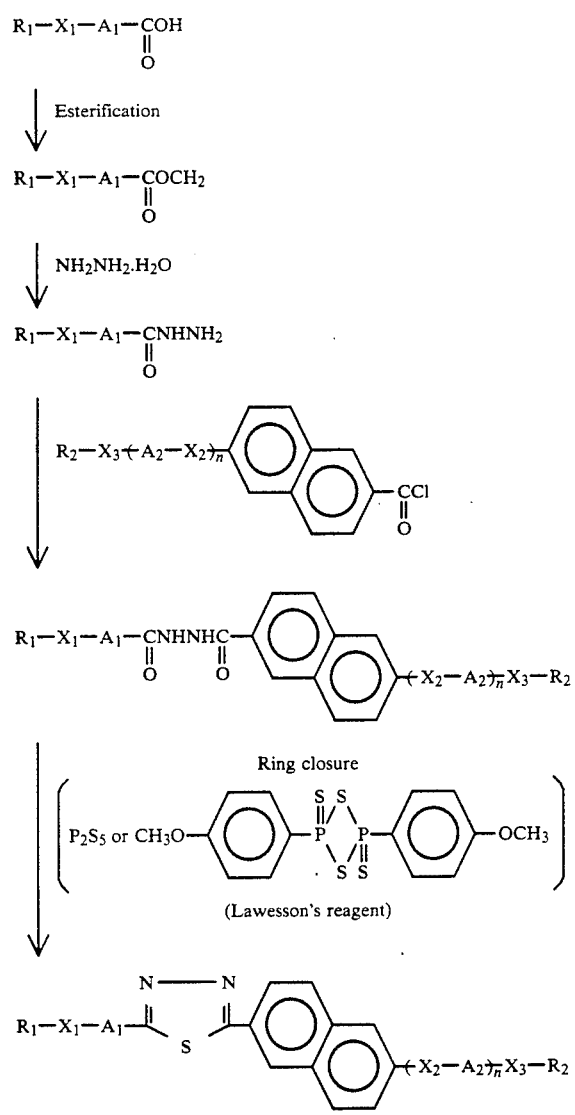

REACTION SCHEME B

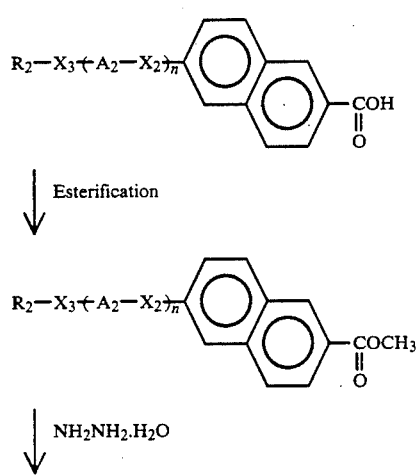

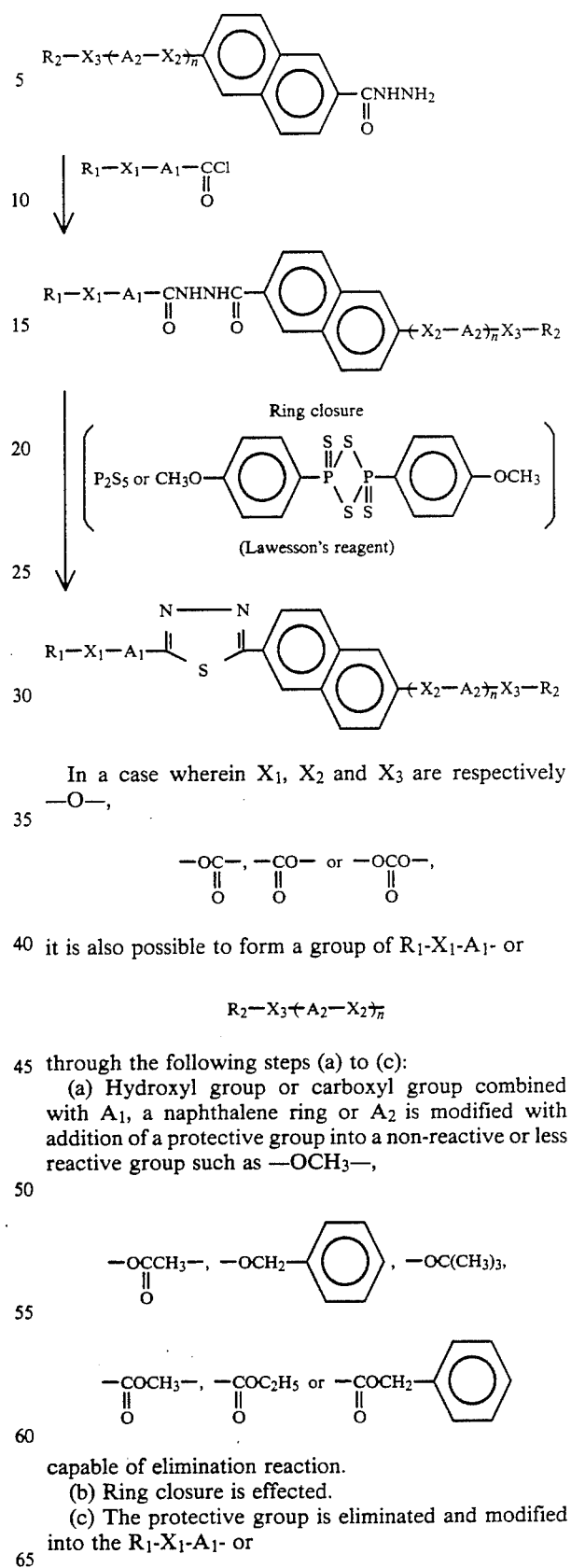

In a case wherein $X_1$, $X_2$ and $X_3$ are respectively —O—, $$-O\underset{\underset{O}{\|}}{C}-, \quad -\underset{\underset{O}{\|}}{C}O- \quad \text{or} \quad -O\underset{\underset{O}{\|}}{C}O-,$$

it is also possible to form a group of $R_1\text{-}X_1\text{-}A_1\text{-}$ or $$R_2-X_3+A_2-X_2\!\!\rightarrow_{\!\!n}$$

through the following steps (a) to (c):

(a) Hydroxyl group or carboxyl group combined with $A_1$, a naphthalene ring or $A_2$ is modified with addition of a protective group into a non-reactive or less reactive group such as —$OCH_3$—, $$-O\underset{\underset{O}{\|}}{C}CH_3-, \quad -OCH_2-\!\!\bigcirc\!\!, \quad -OC(CH_3)_3,$$

$$-\underset{\underset{O}{\|}}{C}OCH_3-, \quad -\underset{\underset{O}{\|}}{C}OC_2H_5 \quad \text{or} \quad -\underset{\underset{O}{\|}}{C}OCH_2-\!\!\bigcirc$$

capable of elimination reaction.

(b) Ring closure is effected.

(c) The protective group is eliminated and modified into the $R_1\text{-}X_1\text{-}A_1\text{-}$ or $$R_2-X_3+A_2-X_2\!\!\rightarrow_{\!\!n}$$

structure.
Specific examples of the mesomorphic compounds represented by the above-mentioned general formula (I) may include those shown by the following structural formulas.
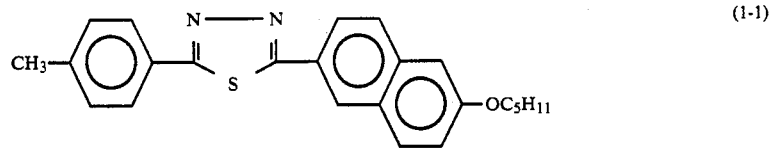 (1-1)
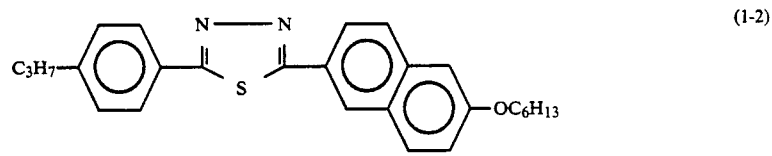 (1-2)
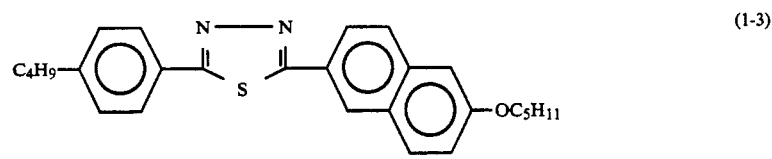 (1-3)
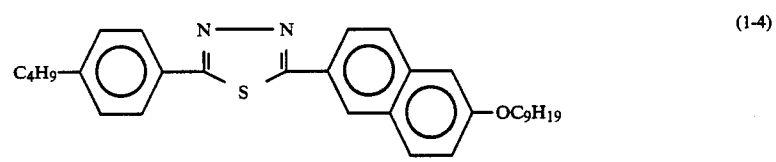 (1-4)
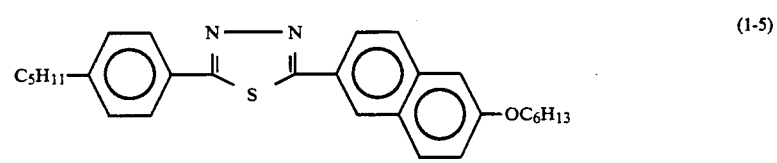 (1-5)
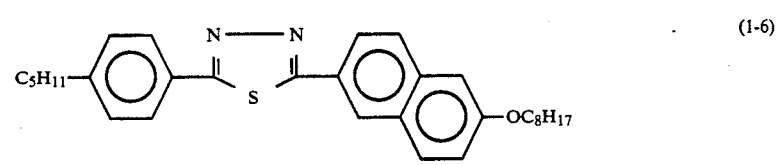 (1-6)
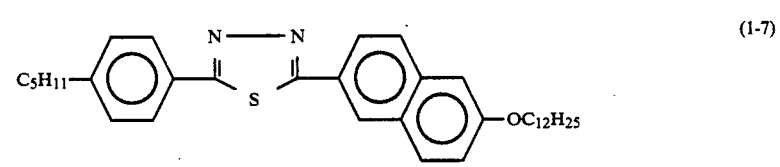 (1-7)
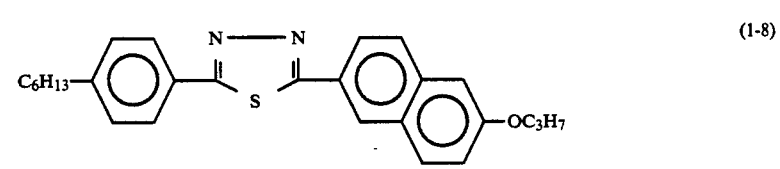 (1-8)
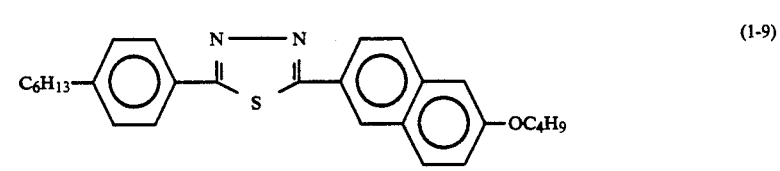 (1-9)
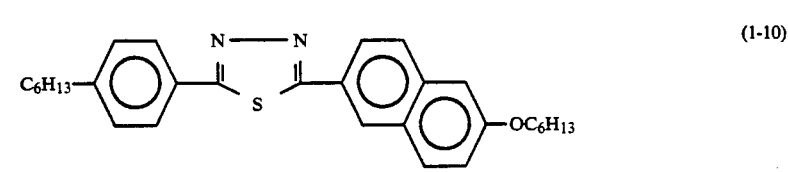 (1-10)

-continued
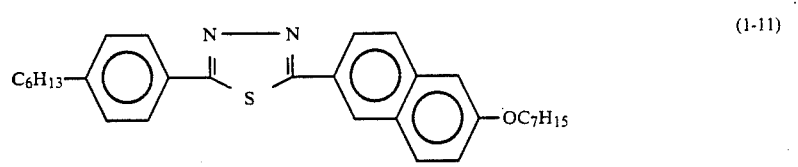 (1-11)
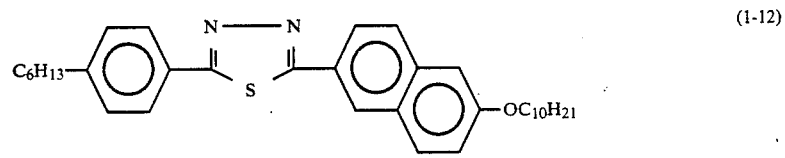 (1-12)
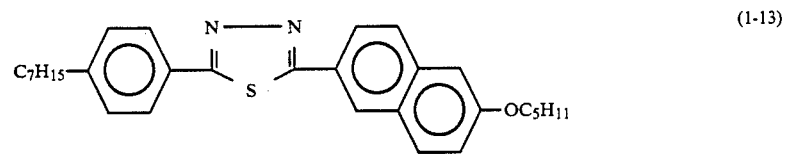 (1-13)
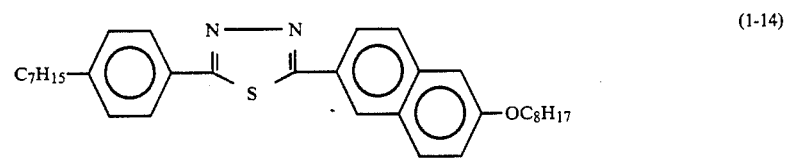 (1-14)
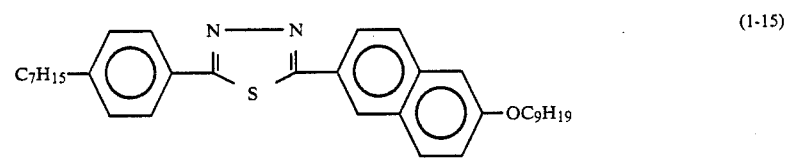 (1-15)
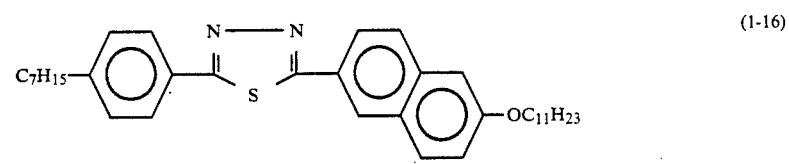 (1-16)
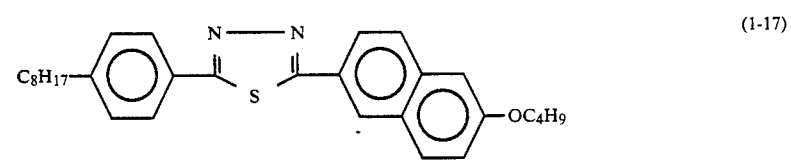 (1-17)
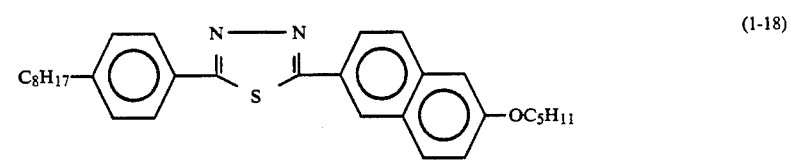 (1-18)
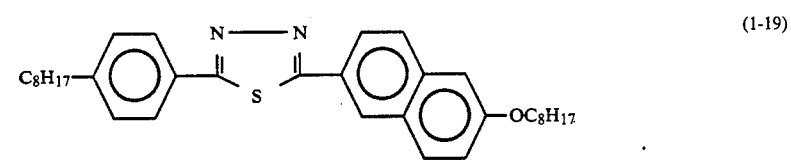 (1-19)
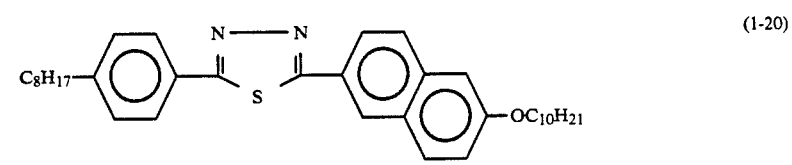 (1-20)

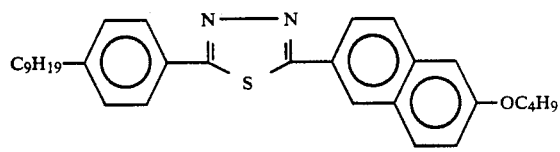
(1-21)
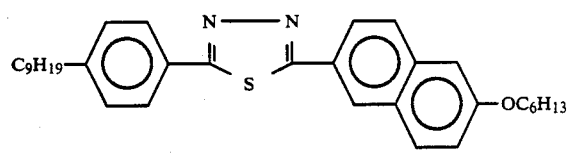
(1-22)
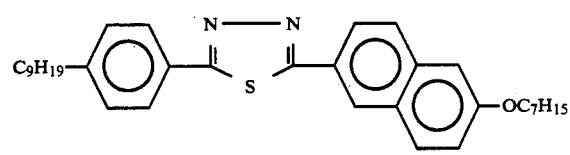
(1-23)
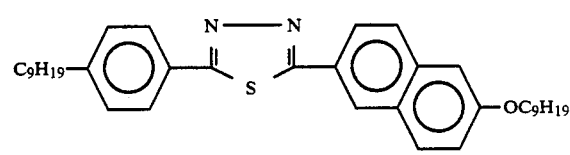
(1-24)
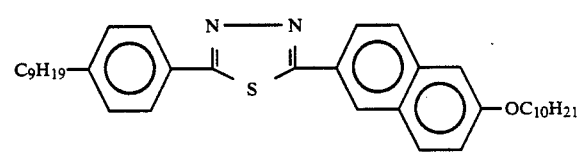
(1-25)
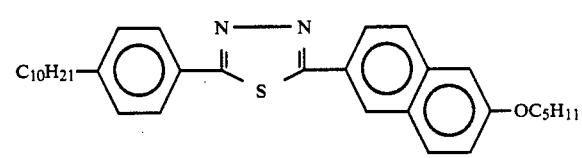
(1-26)
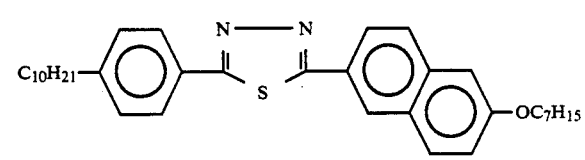
(1-27)
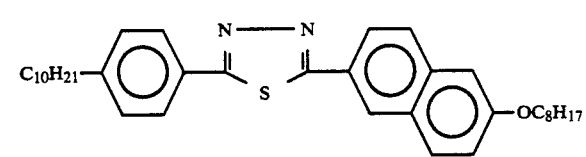
(1-28)
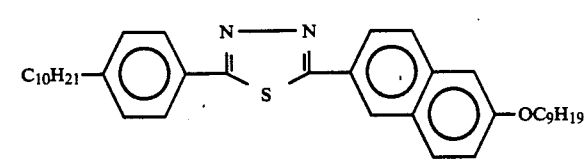
(1-29)
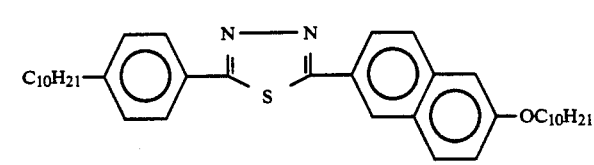
(1-30)

-continued
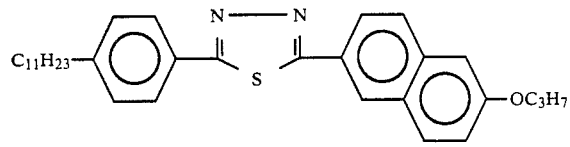 (1-31)
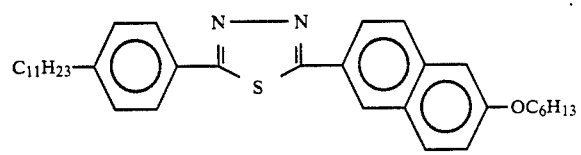 (1-32)
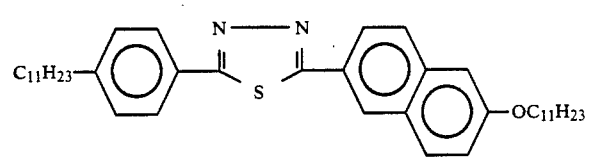 (1-33)
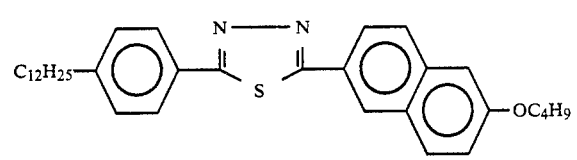 (1-34)
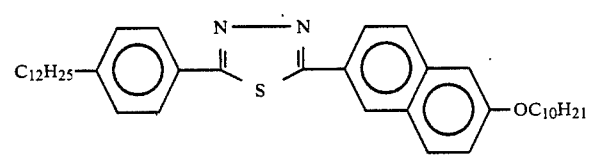 (1-35)
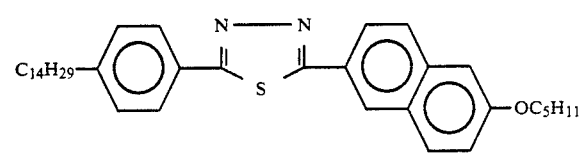 (1-36)
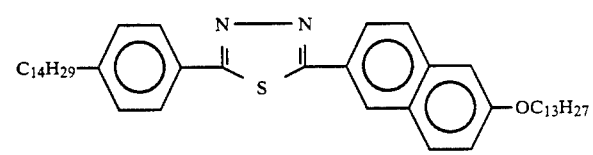 (1-37)
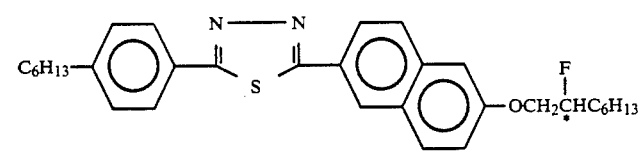 (1-38)
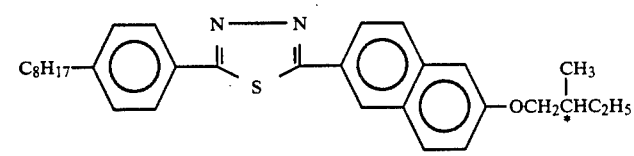 (1-39)
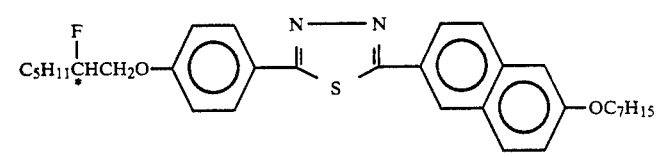 (1-40)

-continued
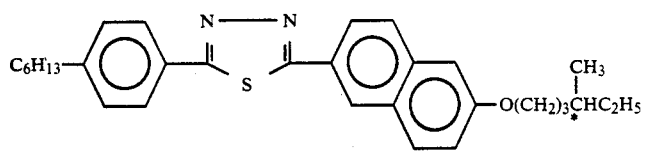 (1-41)
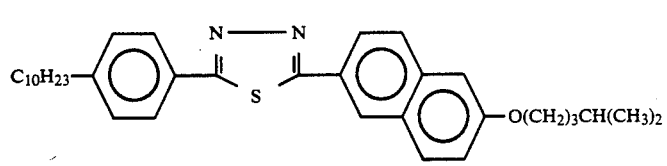 (1-42)
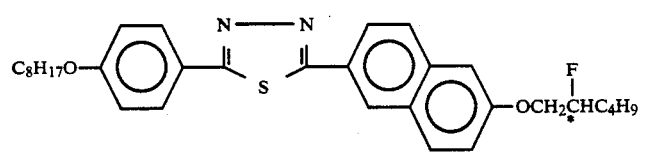 (1-43)
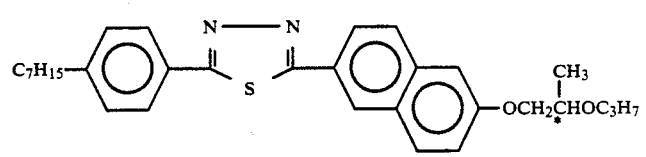 (1-44)
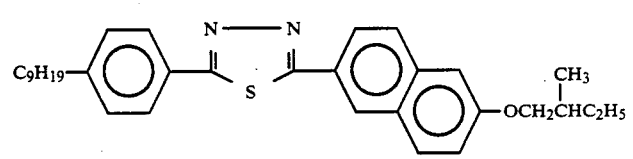 (1-45)
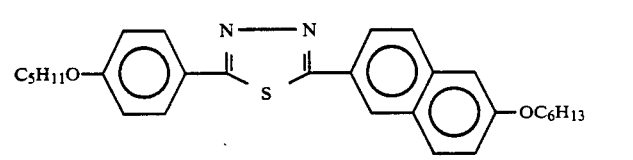 (1-46)
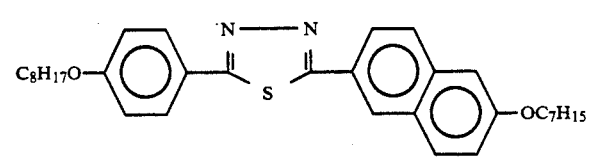 (1-47)
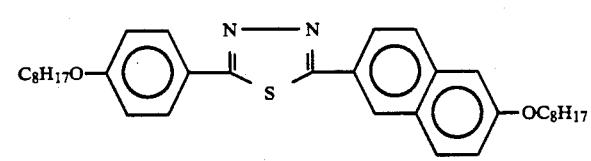 (1-48)
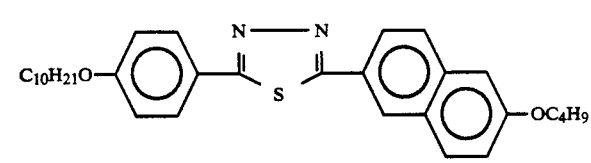 (1-49)
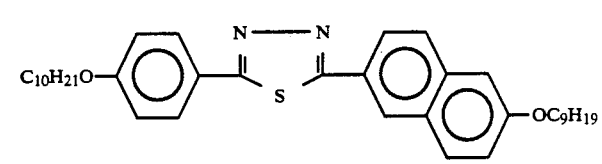 (1-50)

-continued
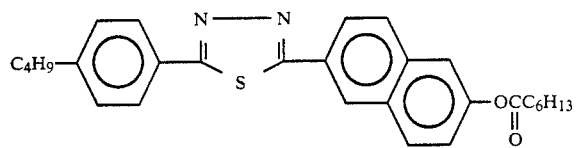 (1-51)
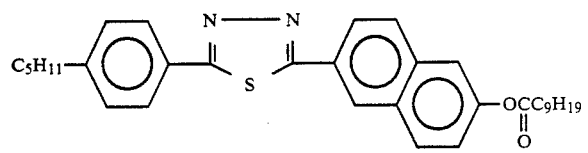 (1-52)
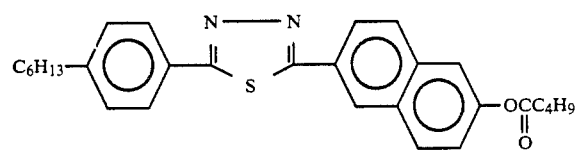 (1-53)
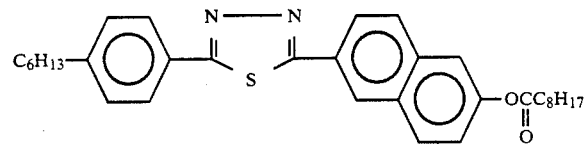 (1-54)
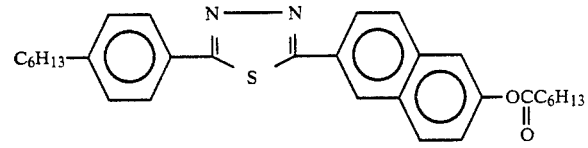 (1-55)
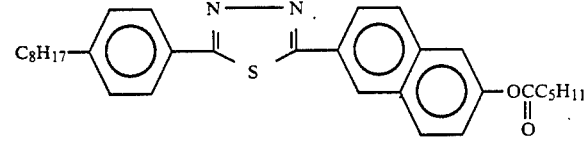 (1-56)
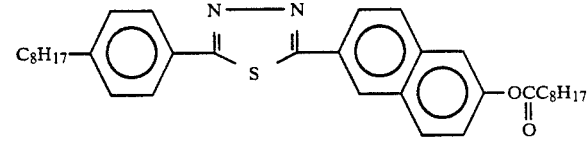 (1-57)
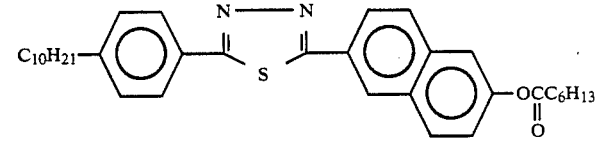 (1-58)
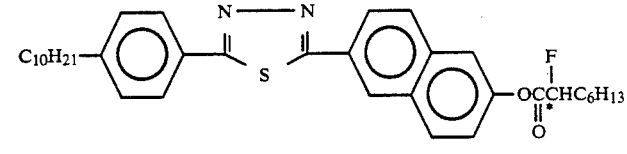 (1-59)
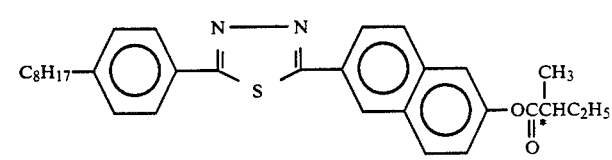 (1-60)

-continued
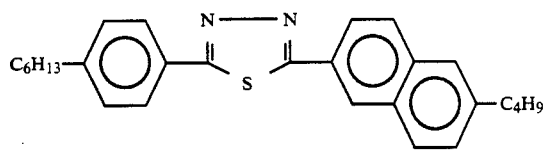 (1-61)
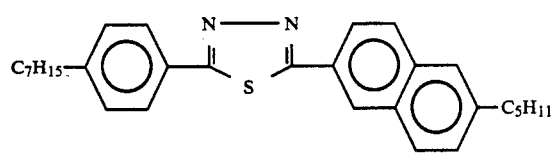 (1-62)
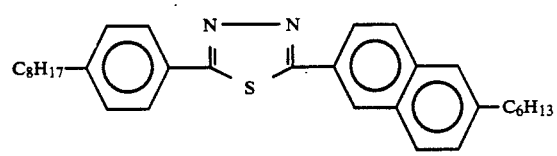 (1-63)
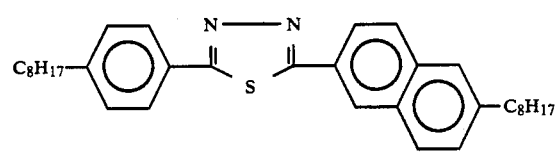 (1-64)
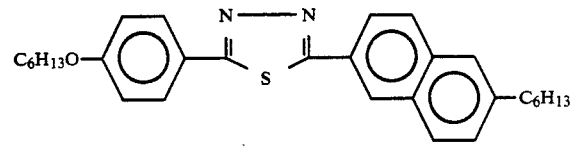 (1-65)
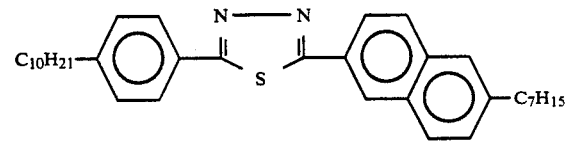 (1-66)
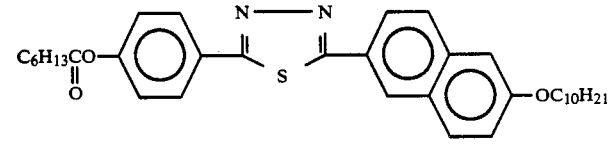 (1-67)
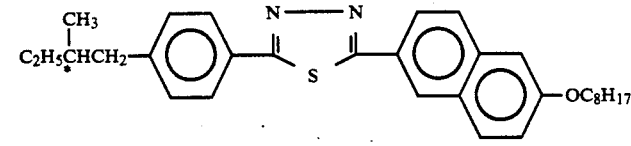 (1-68)
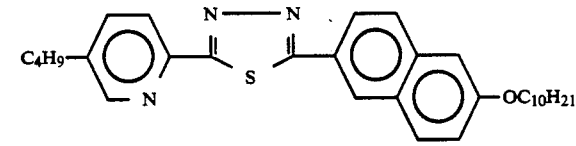 (1-69)
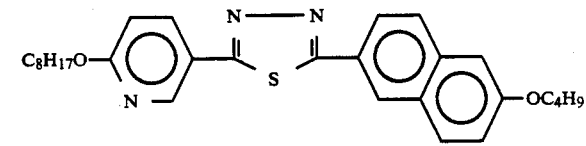 (1-70)

-continued
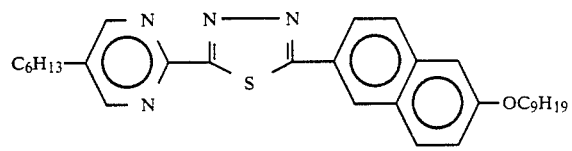 (1-71)
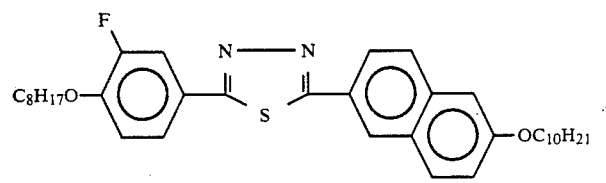 (1-72)
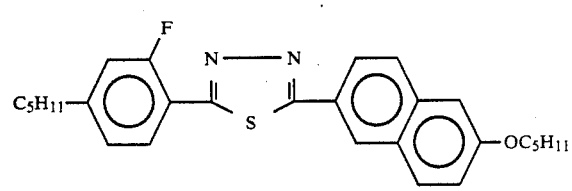 (1-73)
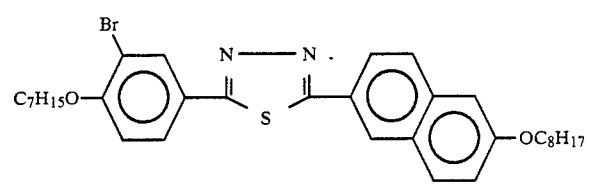 (1-74)
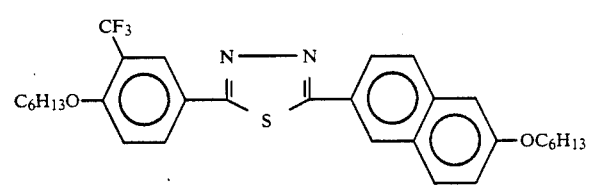 (1-75)
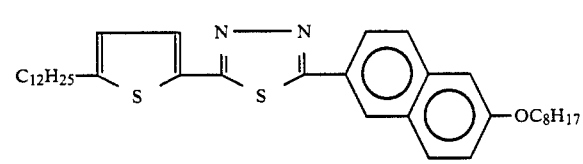 (1-76)
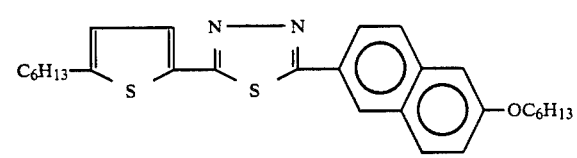 (1-77)
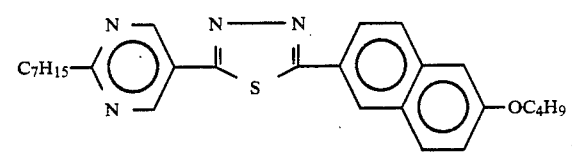 (1-78)
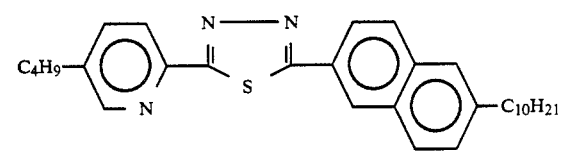 (1-79)

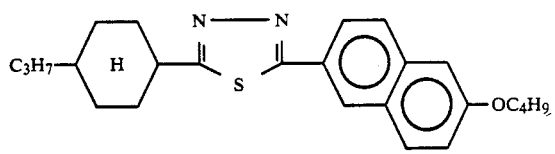 (1-80)
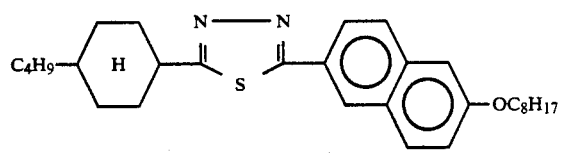 (1-81)
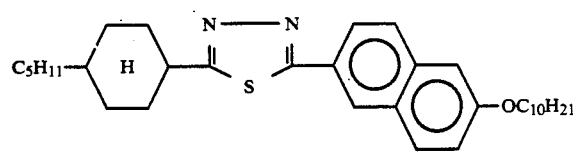 (1-82)
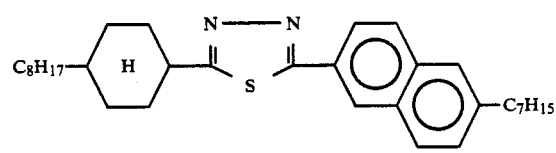 (1-83)
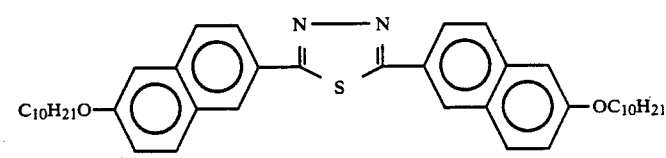 (1-84)
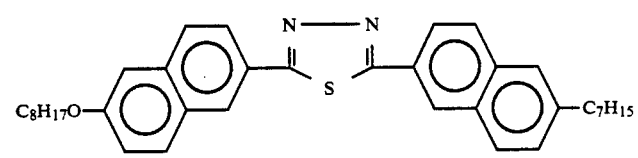 (1-85)
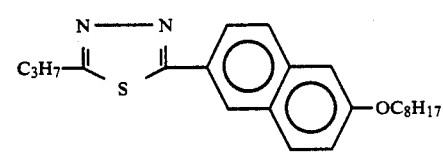 (1-86)
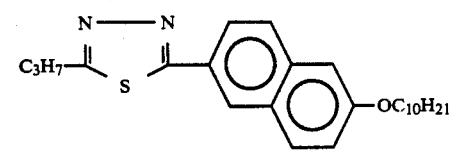 (1-87)
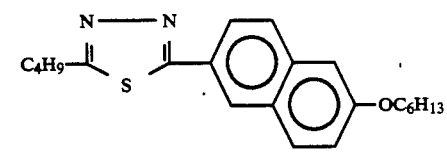 (1-88)
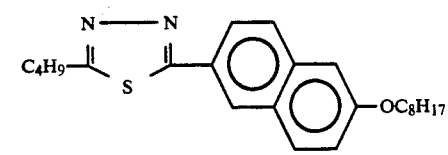 (1-89)

-continued
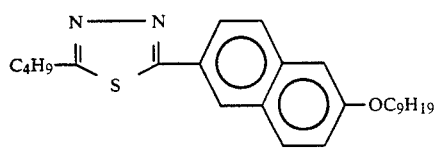 (1-90)
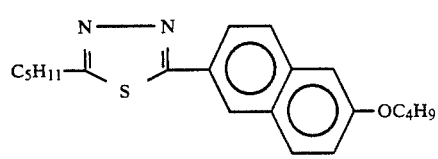 (1-91)
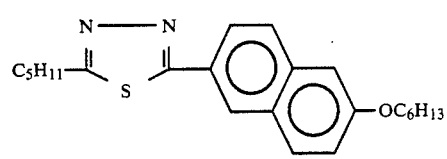 (1-92)
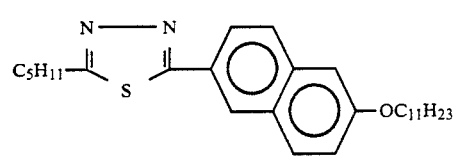 (1-93)
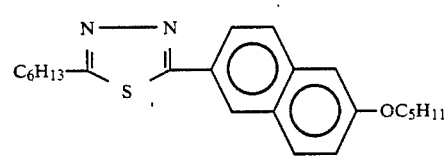 (1-94)
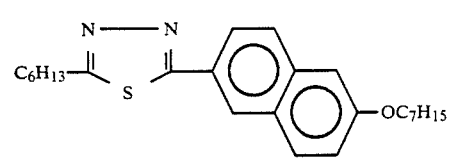 (1-95)
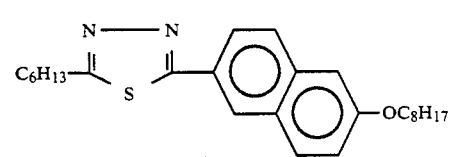 (1-96)
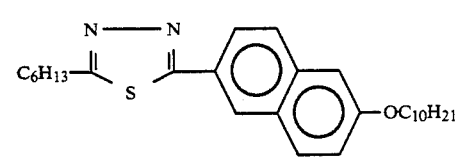 (1-97)
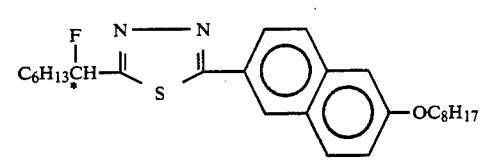 (1-98)
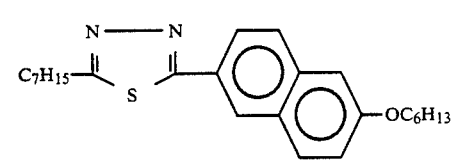 (1-99)

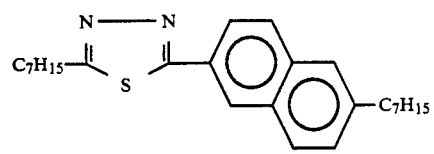
(1-100)
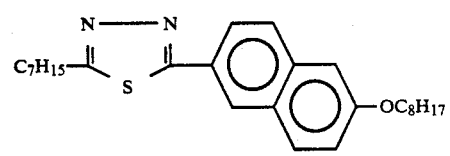
(1-101)
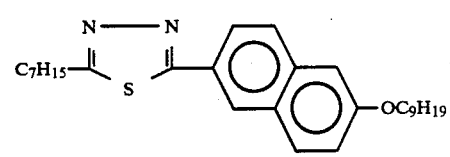
(1-102)
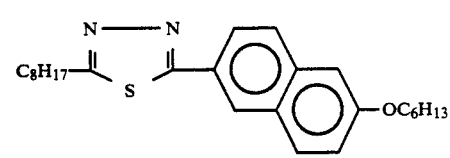
(1-103)
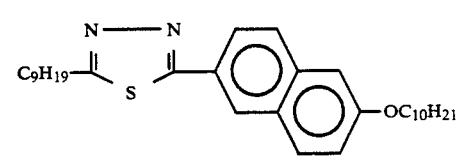
(1-104)
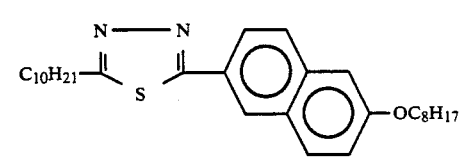
(1-105)
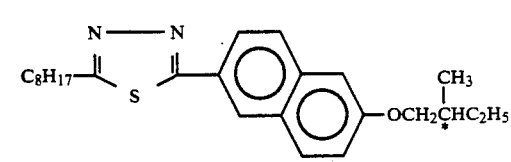
(1-106)
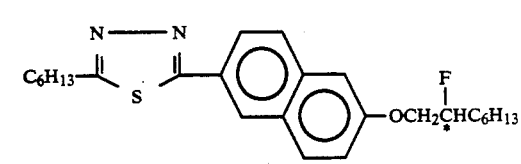
(1-107)
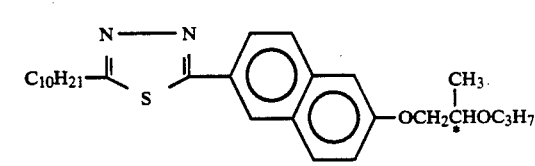
(1-108)
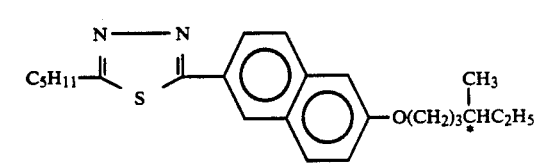
(1-109)

-continued
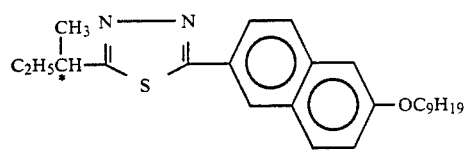 (1-110)
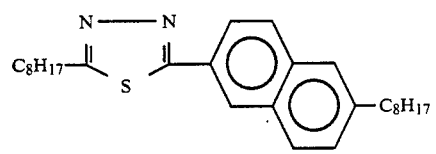 (1-111)
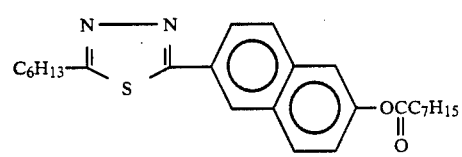 (1-112)
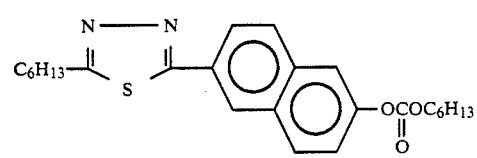 (1-113)
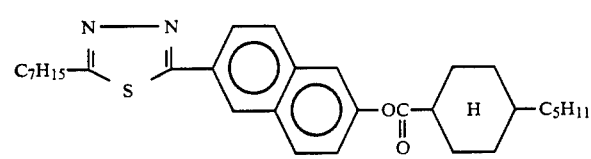 (1-114)
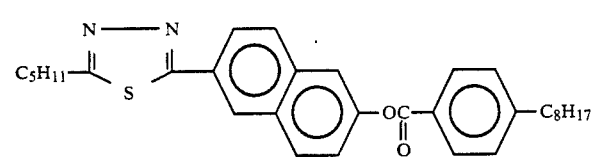 (1-115)
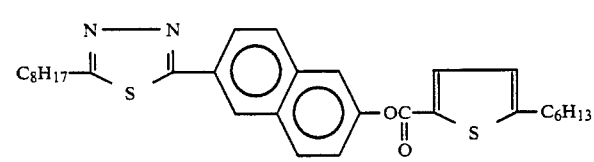 (1-116)
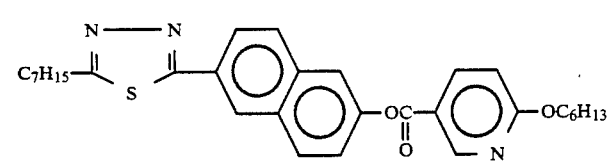 (1-117)
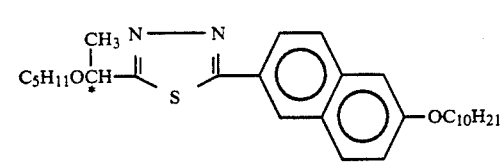 (1-118)
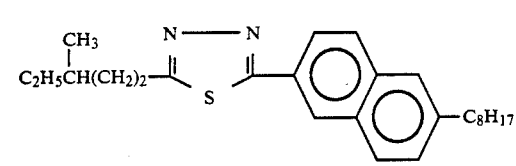 (1-119)

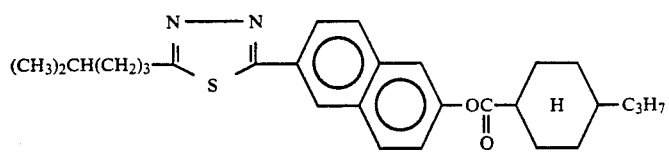 (1-120)
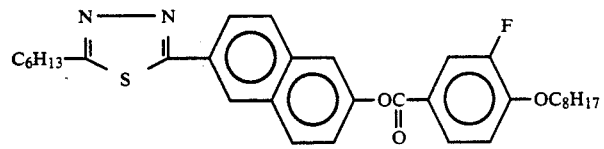 (1-121)
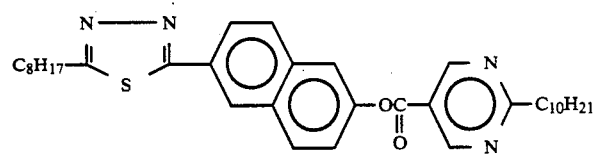 (1-122)
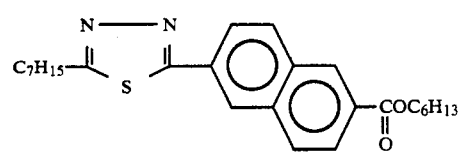 (1-123)
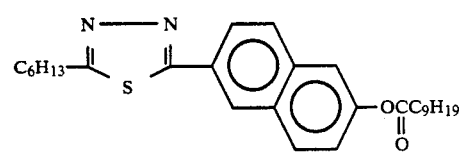 (1-124)
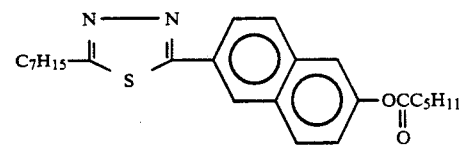 (1-125)
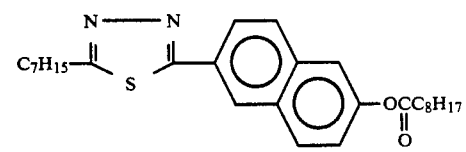 (1-126)
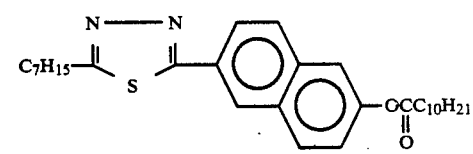 (1-127)
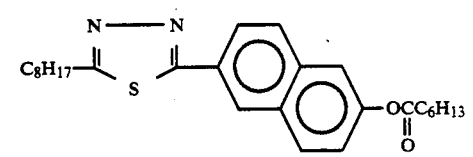 (1-128)
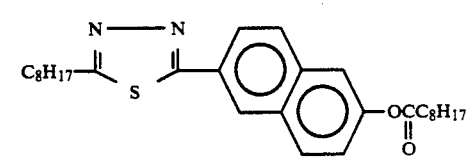 (1-129)

-continued
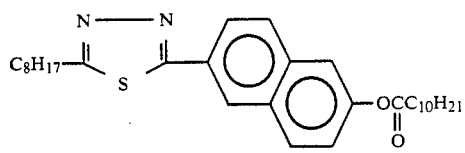 (1-130)
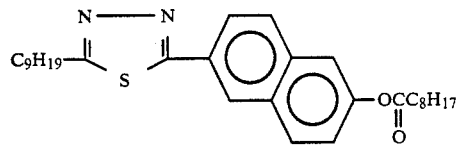 (1-131)
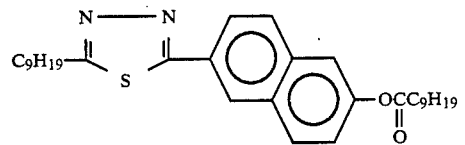 (1-132)
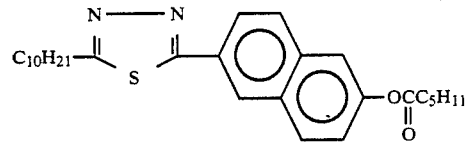 (1-133)
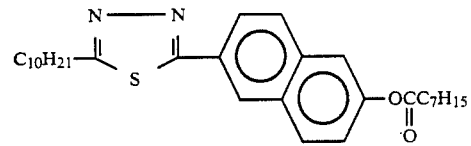 (1-134)
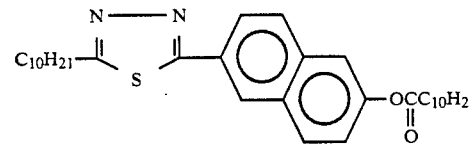 (1-135)
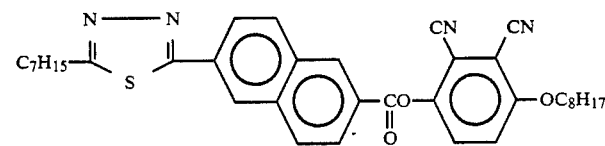 (1-136)
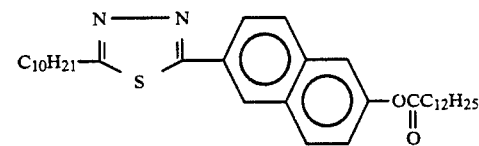 (1-137)
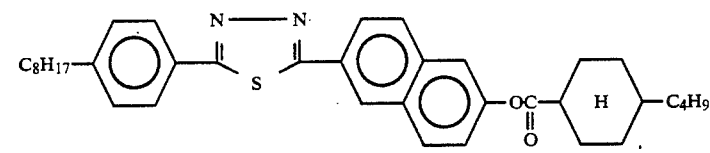 (1-138)
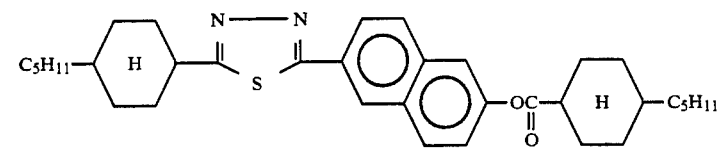 (1-139)

-continued
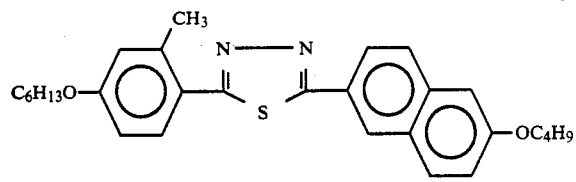 (1-140)
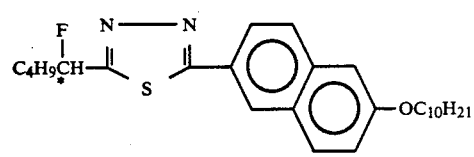 (1-141)
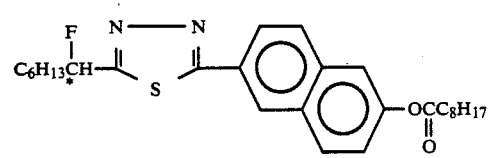 (1-142)
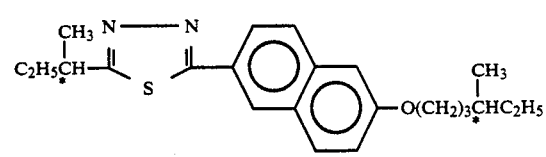 (1-143)
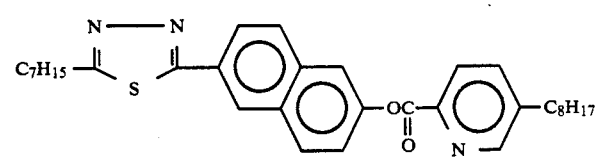 (1-144)
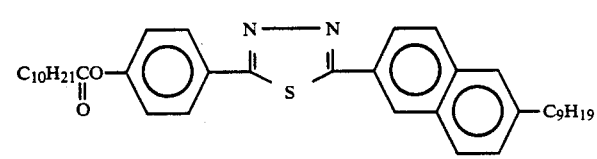 (1-145)
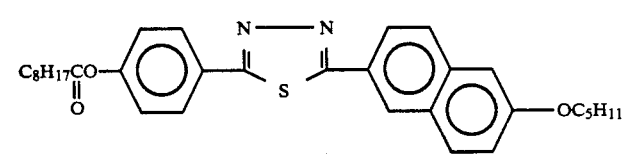 (1-146)
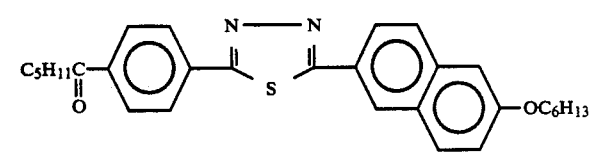 (1-147)
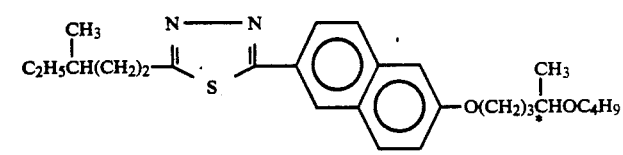 (1-148)
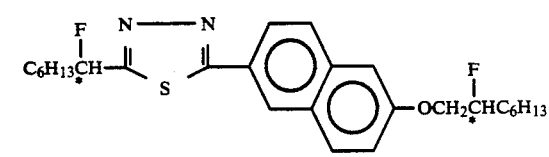 (1-149)

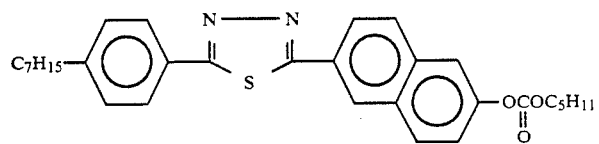 (1-150)
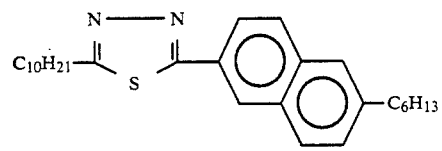 (1-151)
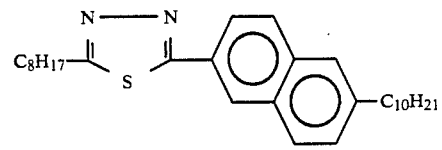 (1-152)
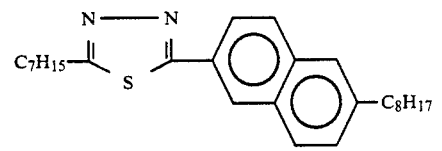 (1-153)
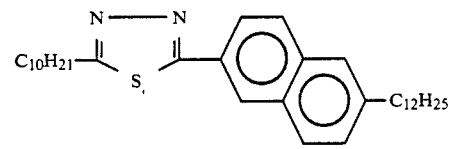 (1-154)
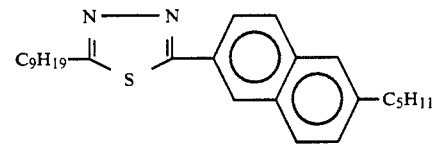 (1-155)
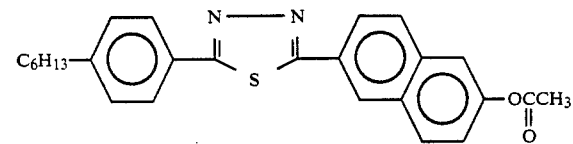 (1-156)
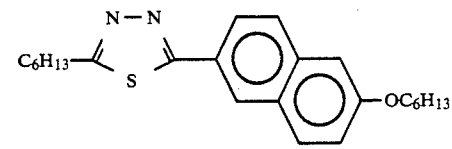 (1-157)
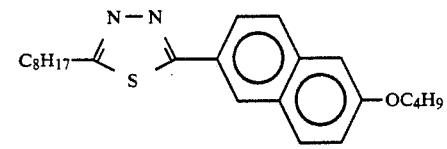 (1-158)
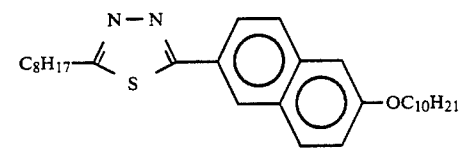 (1-159)

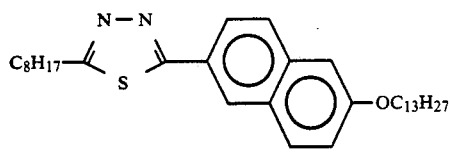 (1-160)

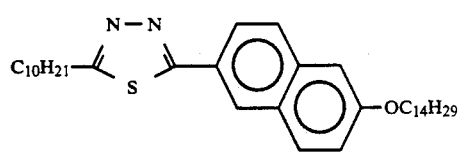 (1-161)

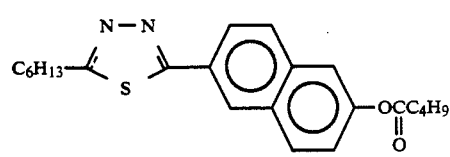 (1-162)

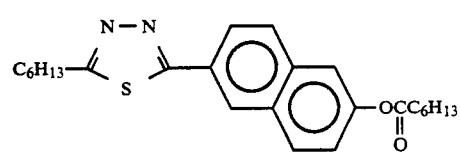 (1-163)

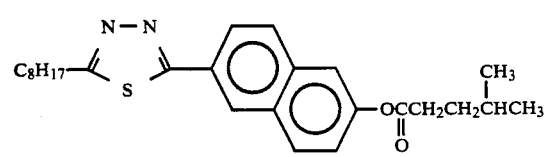 (1-164)

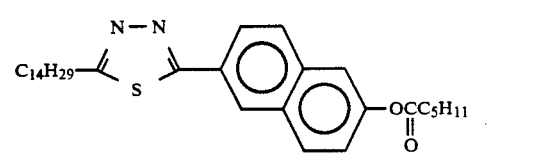 (1-165)

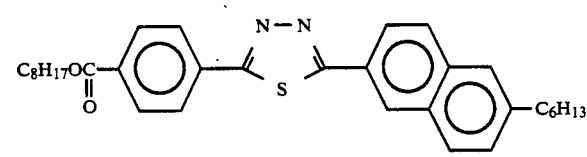 (1-166)

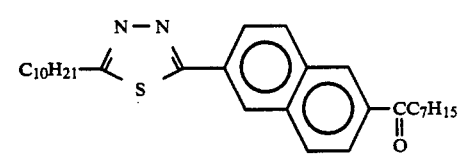 (1-167)

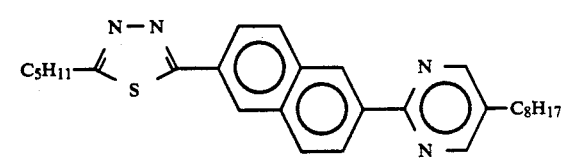 (1-168)

The liquid crystal composition according to the present invention may be obtained by mixing at least one species of the compound represented by the formula (I) and at least one species of another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compound as described above may include those denoted by the following structural formulas.

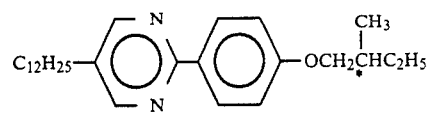 (1)
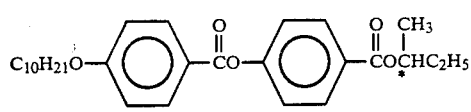 (2)
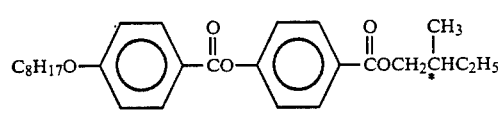 (3)
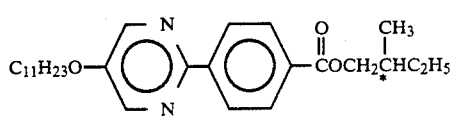 (4)
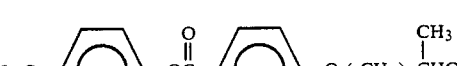 (5)
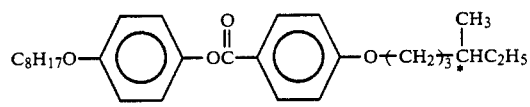 (6)
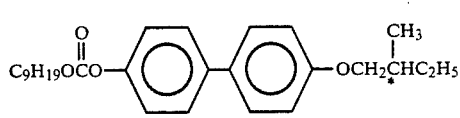 (7)
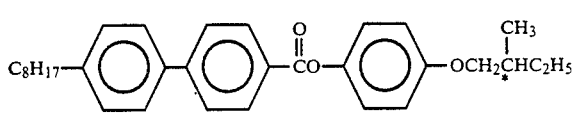 (8)
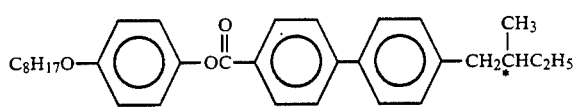 (9)
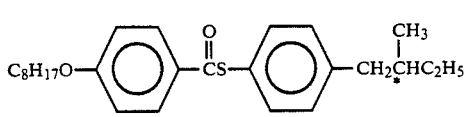 (10)
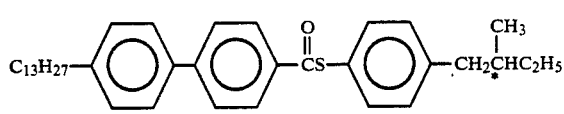 (11)
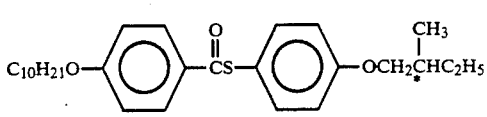 (12)
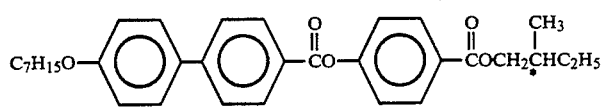 (13)
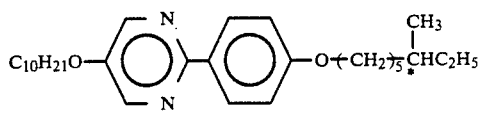

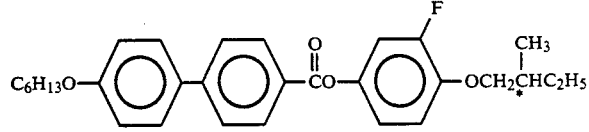 (14)
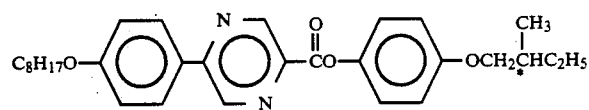 (15)
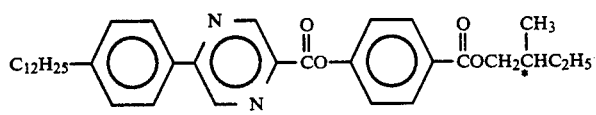 (16)
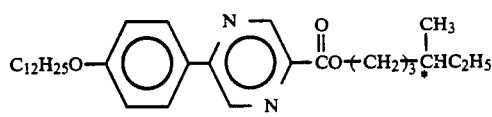 (17)
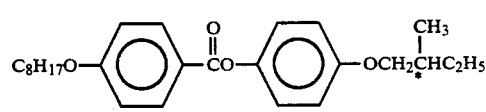 (18)
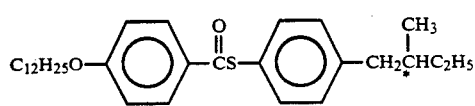 (19)
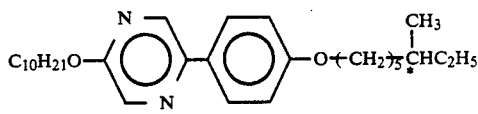 (20)
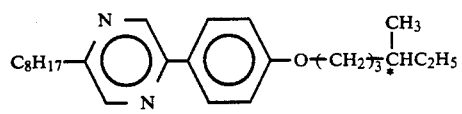 (21)
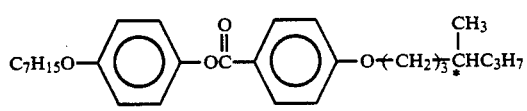 (22)
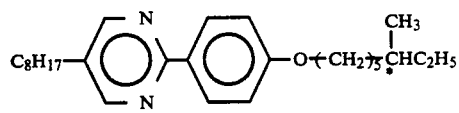 (23)
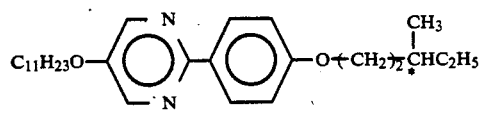 (24)
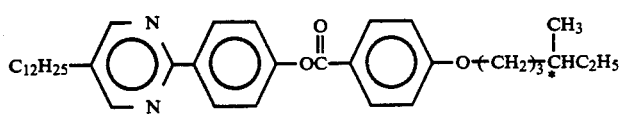 (25)
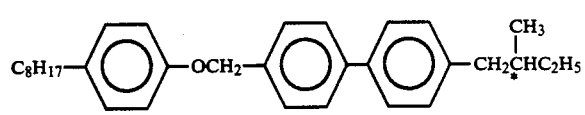 (26)

-continued
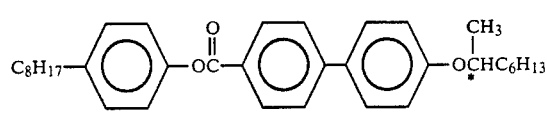 (27)
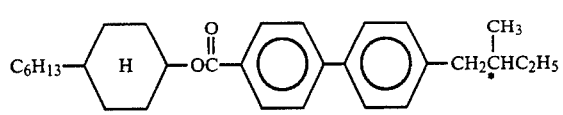 (28)
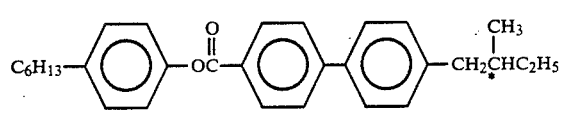 (29)
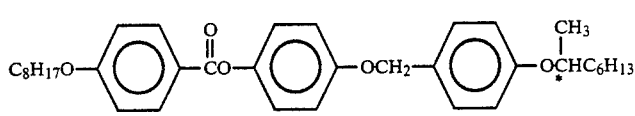 (30)
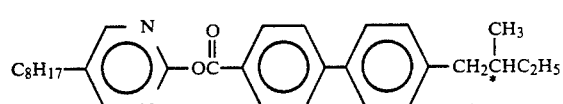 (31)
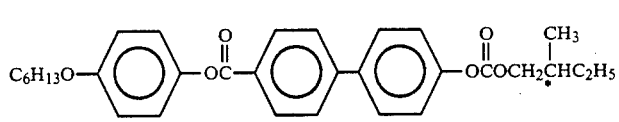 (32)
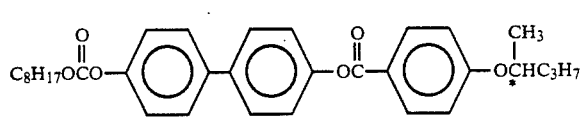 (33)
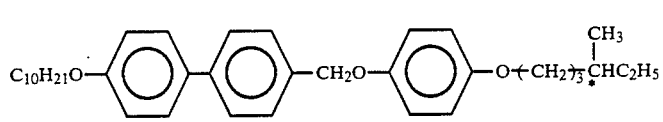 (34)
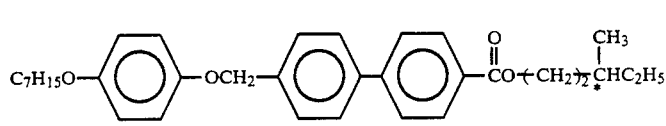 (35)
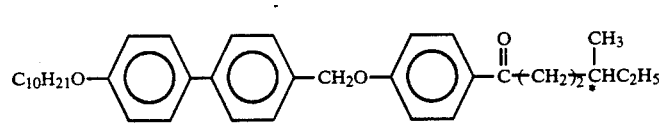 (36)
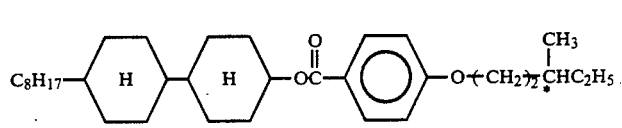 (37)
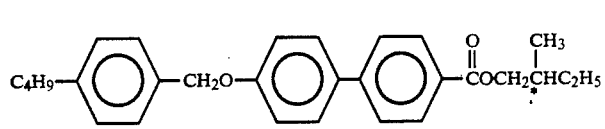 (38)
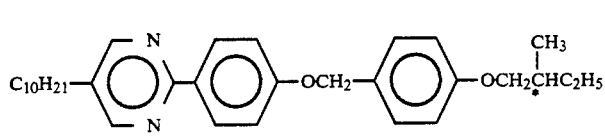 (39)

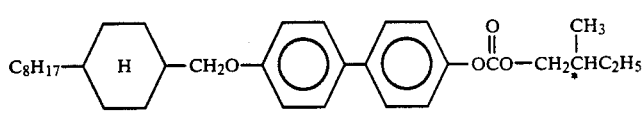
(40)
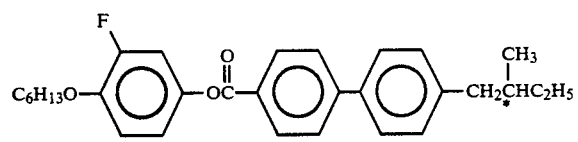
(41)
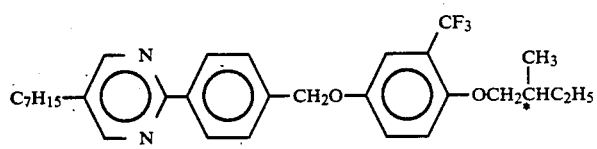
(42)
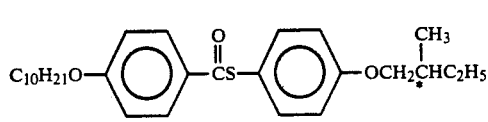
(43)
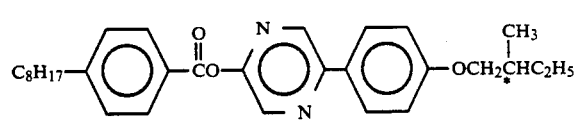
(44)
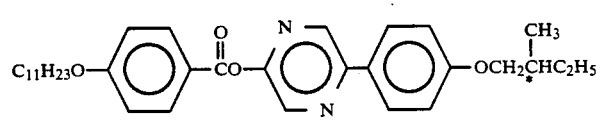
(45)
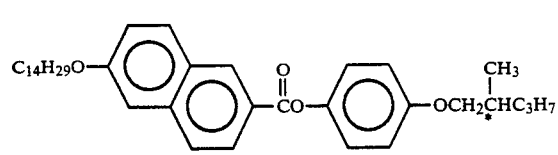
(46)
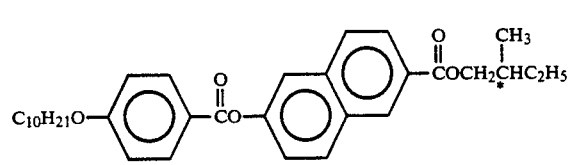
(47)
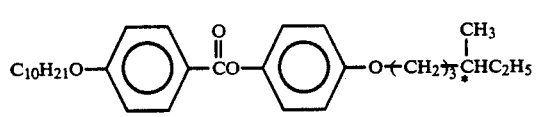
(48)
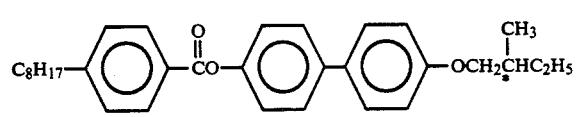
(49)
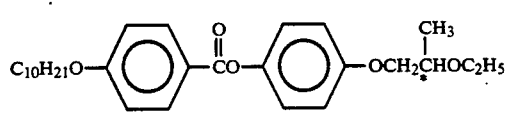
(50)
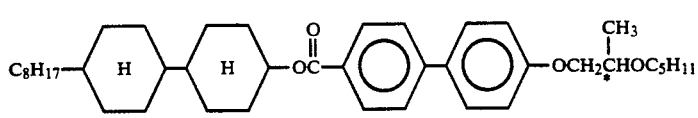
(51)

-continued
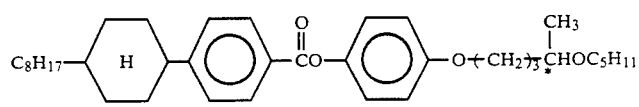 (52)
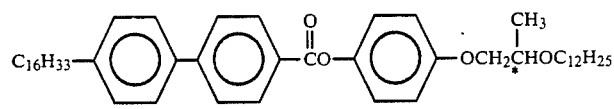 (53)
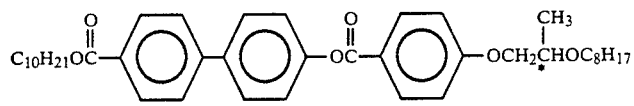 (54)
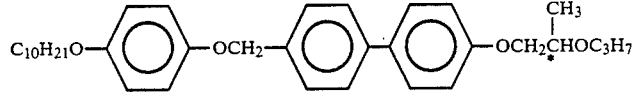 (55)
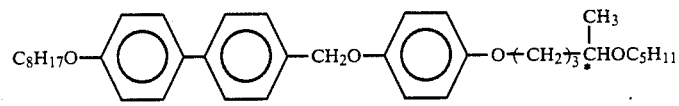 (56)
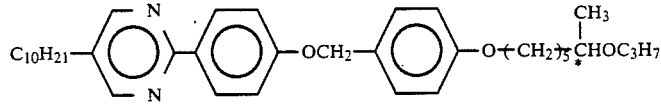 (57)
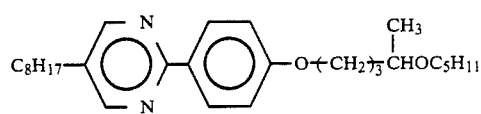 (58)
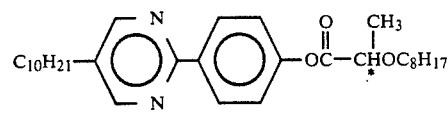 (59)
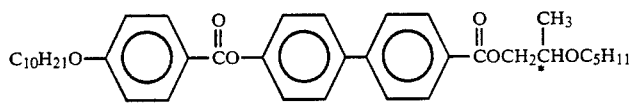 (60)
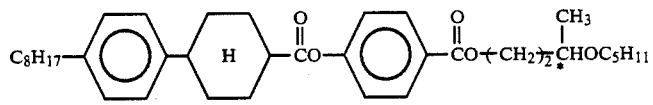 (61)
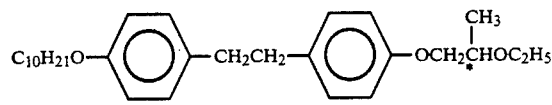 (62)
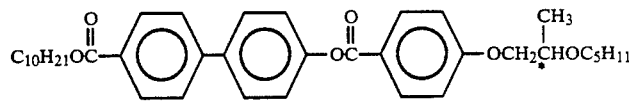 (63)
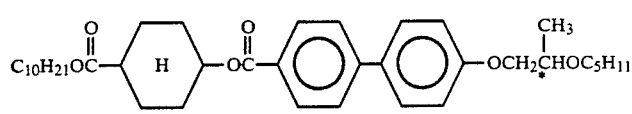 (64)

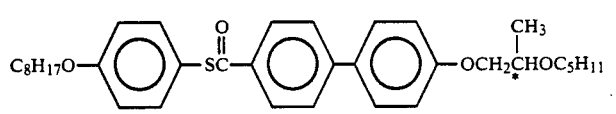 (65)
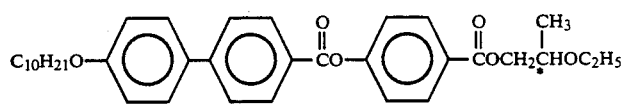 (66)
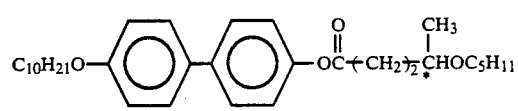 (67)
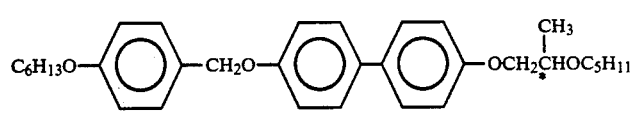 (68)
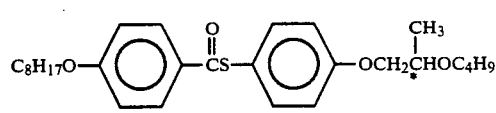 (69)
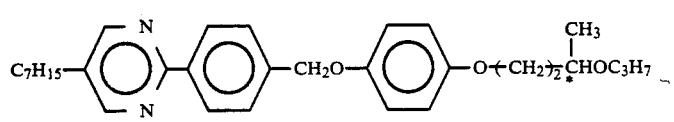 (70)
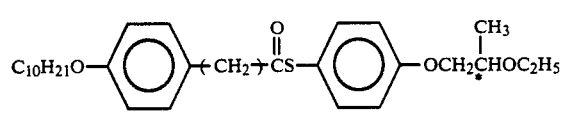 (71)
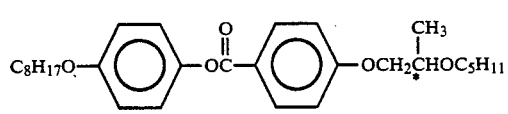 (72)
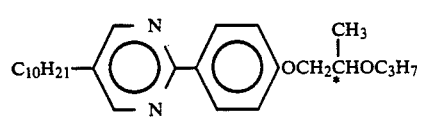 (73)
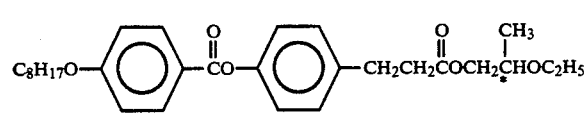 (74)
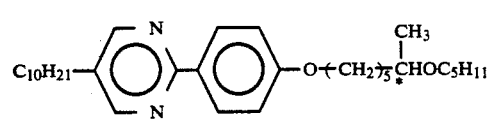 (75)
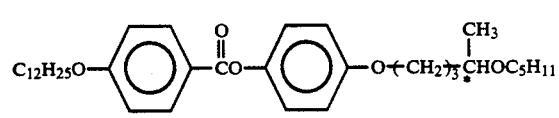 (76)
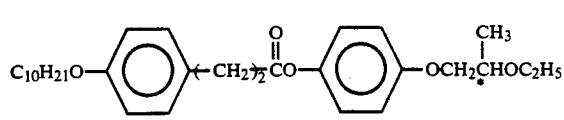 (77)

-continued
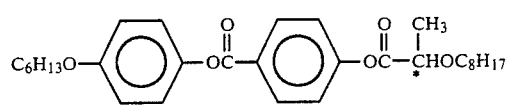 (78)
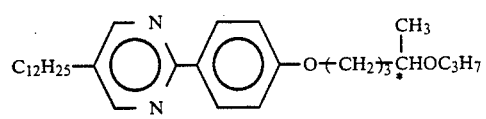 (79)
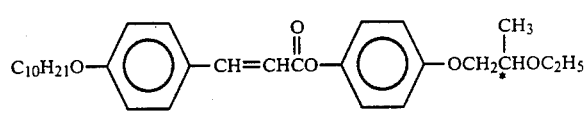 (80)
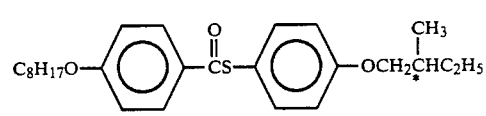 (81)
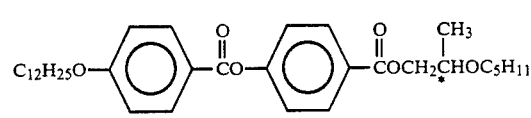 (82)
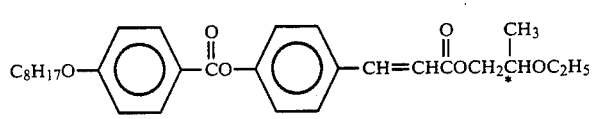 (83)
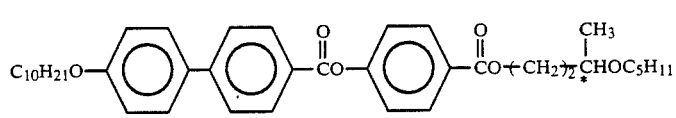 (84)
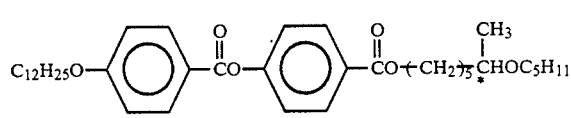 (85)
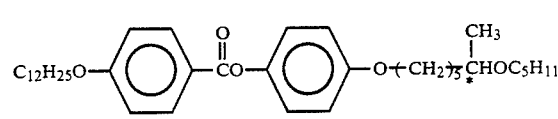 (86)
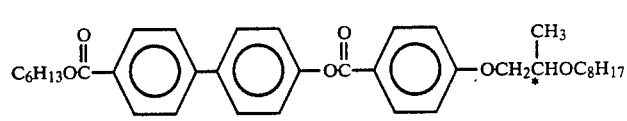 (87)
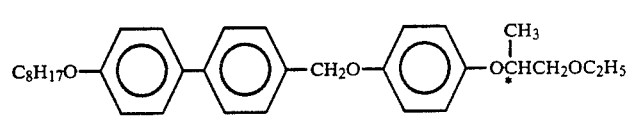 (88)
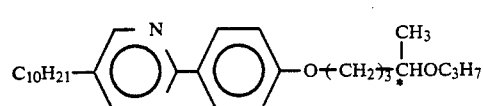 (89)
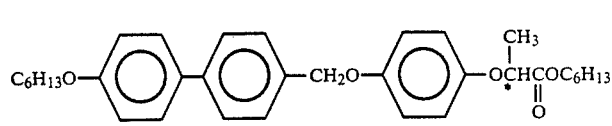 (90)

-continued
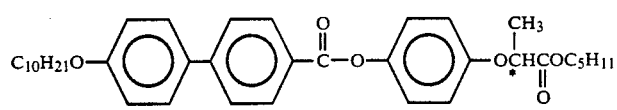 (91)
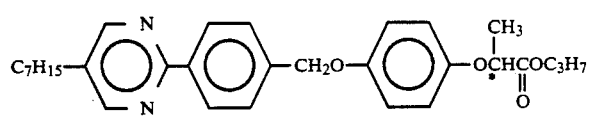 (92)
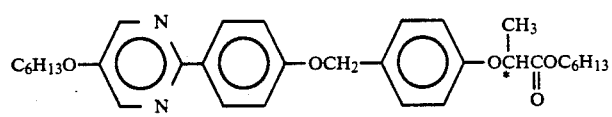 (93)
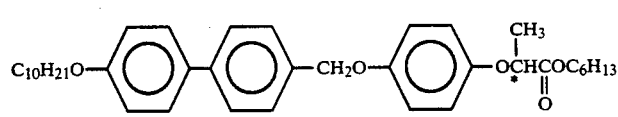 (94)
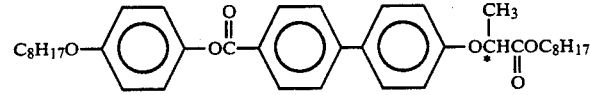 (95)
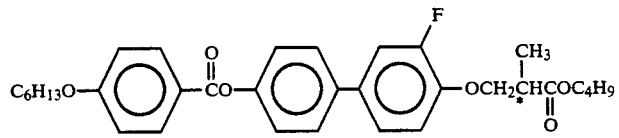 (96)
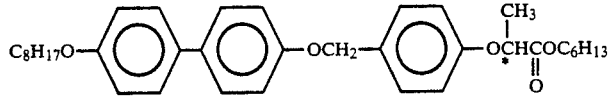 (97)
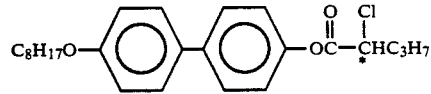 (98)
 (99)
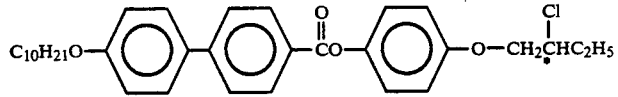 (100)
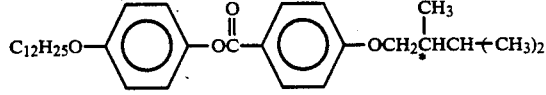 (101)
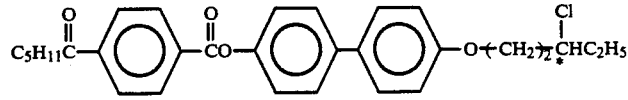 (102)
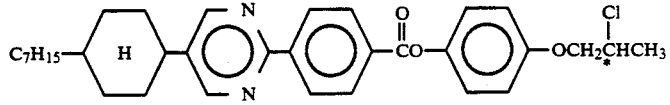 (103)

-continued
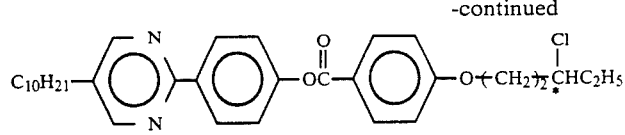 (104)
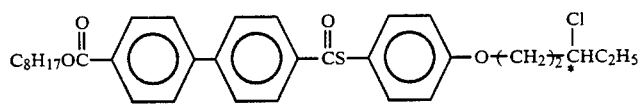 (105)
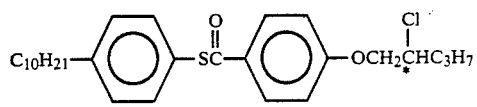 (106)
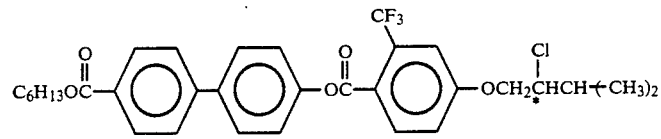 (107)
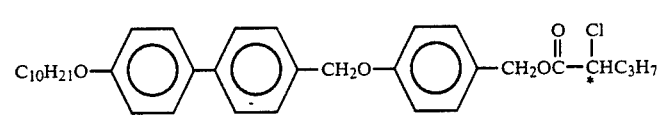 (108)
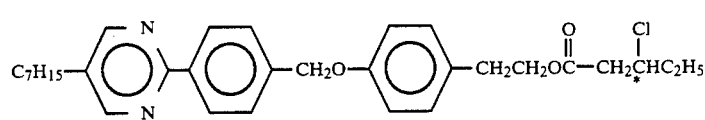 (109)
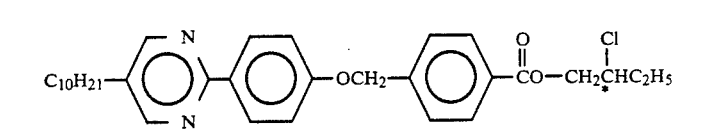 (110)
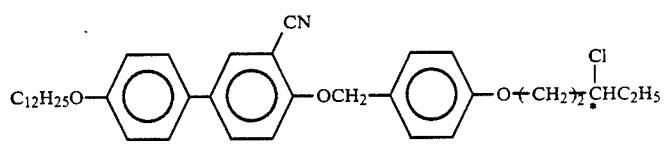 (111)
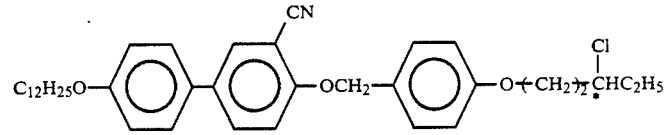 (112)
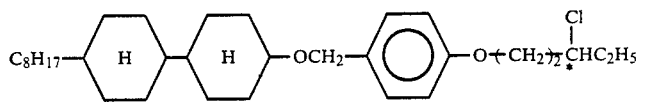 (113)
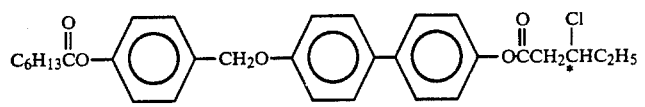 (114)
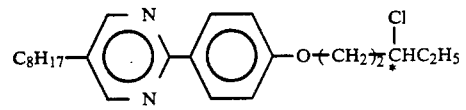 (115)
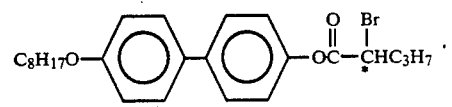 (116)

-continued
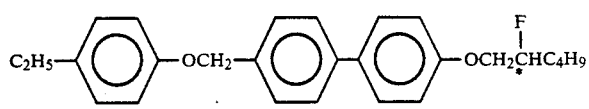 (117)
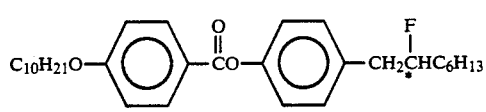 (118)
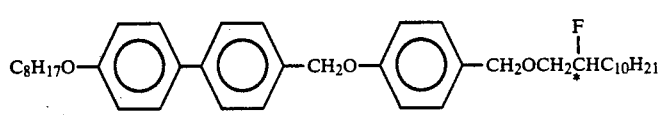 (119)
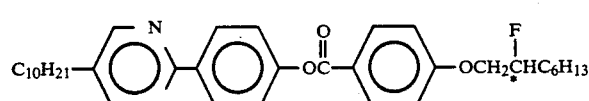 (120)
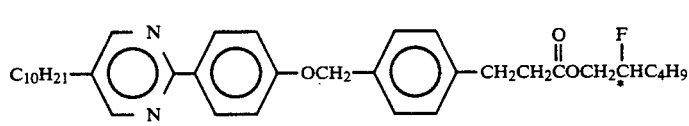 (121)
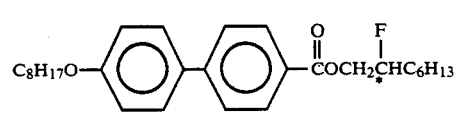 (122)
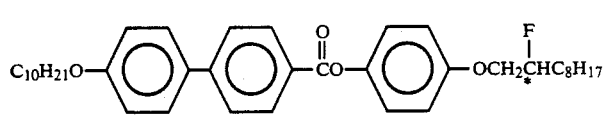 (123)
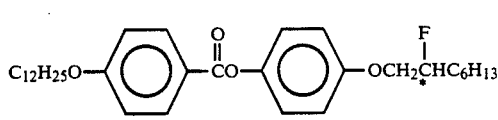 (124)
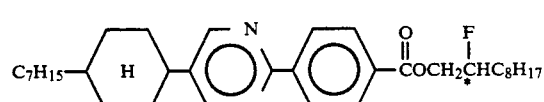 (125)
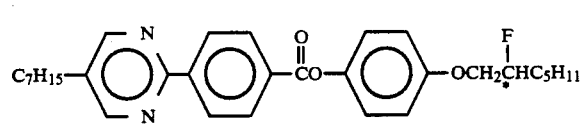 (126)
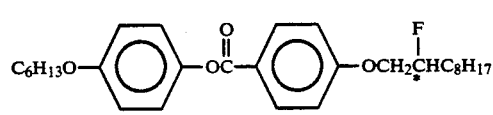 (127)
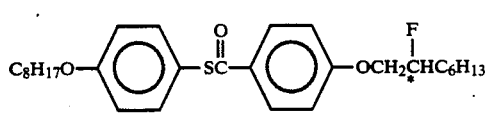 (128)
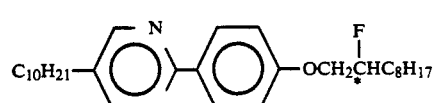 (129)

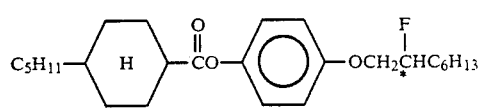 (130)
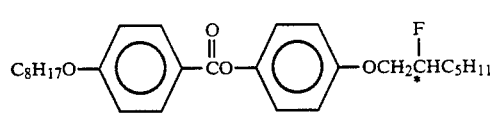 (131)
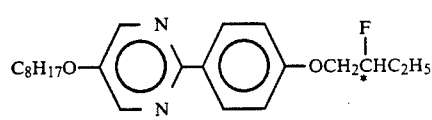 (132)
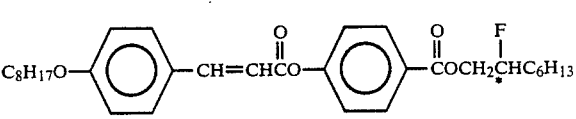 (133)
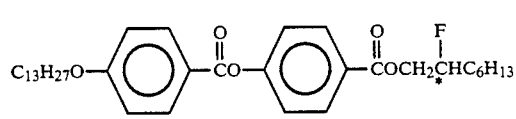 (134)
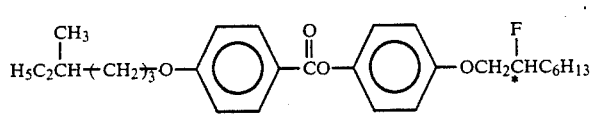 (135)
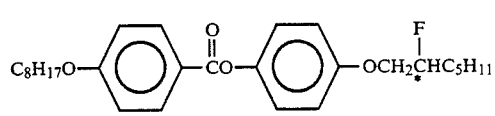 (136)
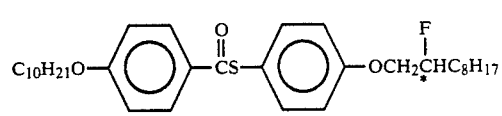 (137)
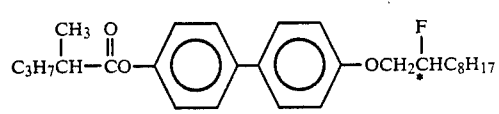 (138)
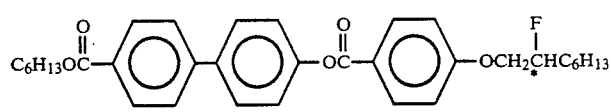 (139)
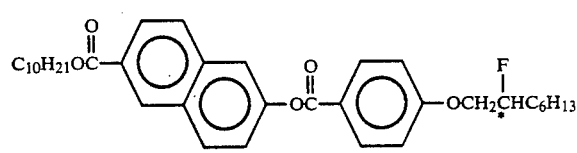 (140)
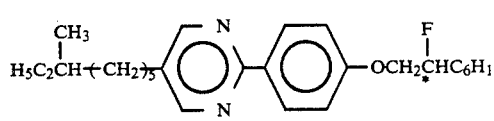 (141)
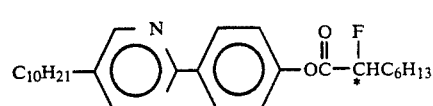 (142)

-continued
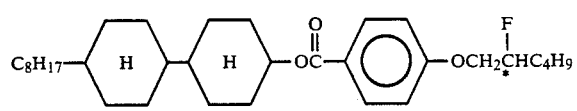 (143)
 (144)
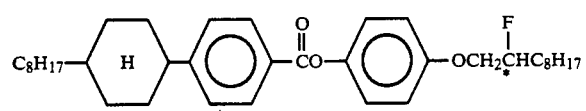 (145)
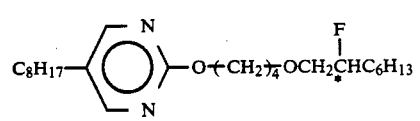 (146)
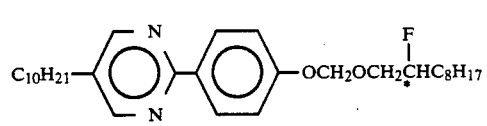 (147)
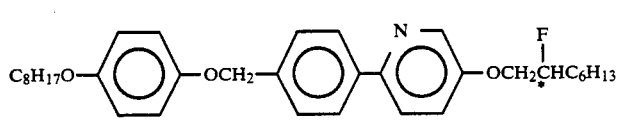 (148)
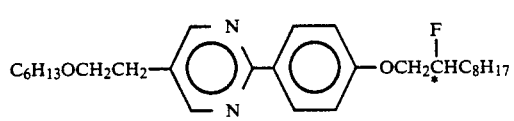 (149)
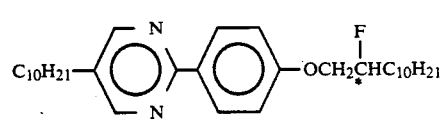 (150)
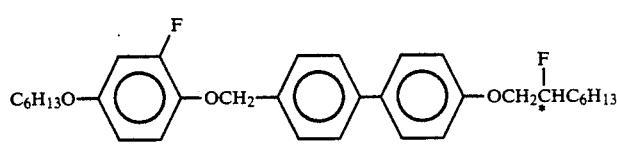 (151)
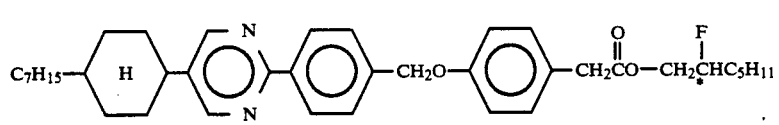 (152)
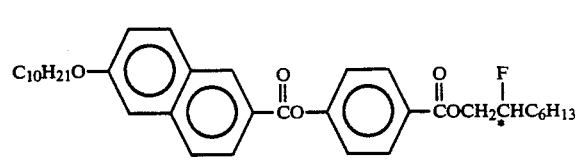 (153)
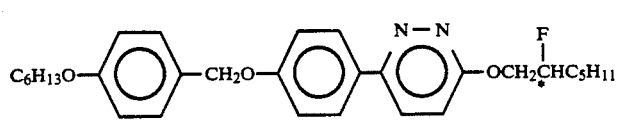 (154)
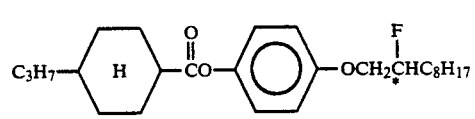 (155)

-continued
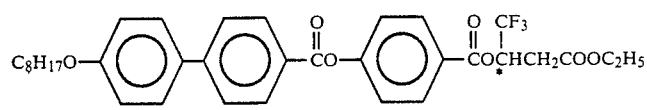 (156)
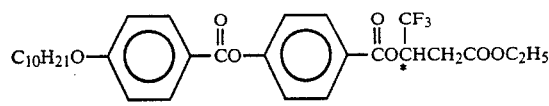 (157)
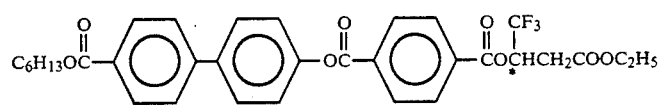 (158)
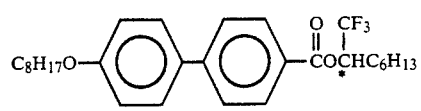 (159)
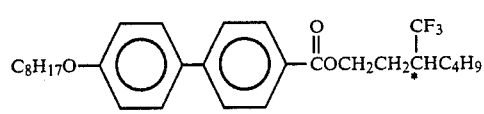 (160)
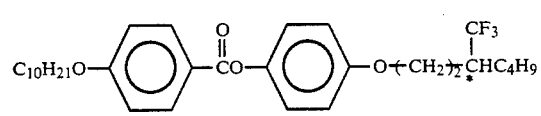 (161)
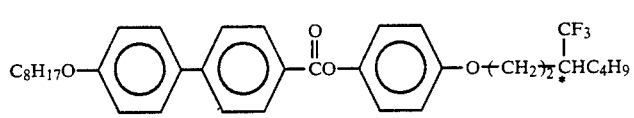 (162)
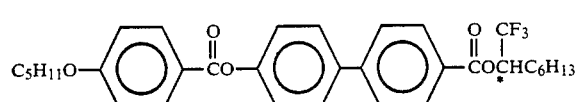 (163)
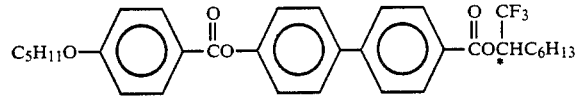 (164)
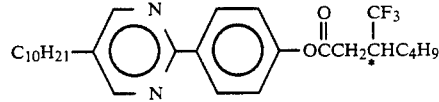 (165)
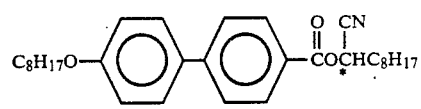 (166)
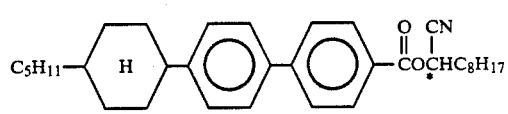 (167)
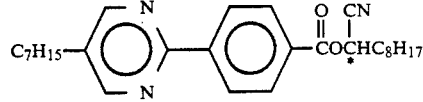 (168)

-continued
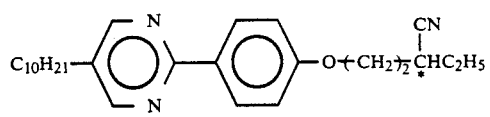 (169)
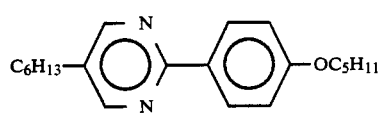 (170)
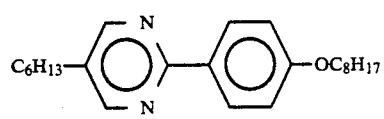 (171)
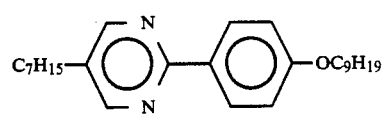 (172)
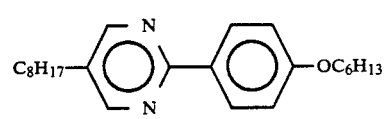 (173)
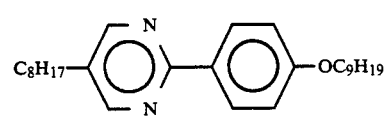 (174)
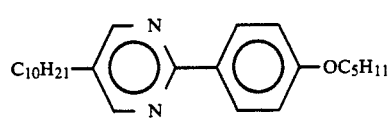 (175)
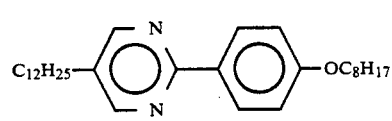 (176)
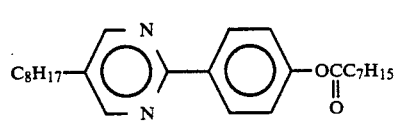 (177)
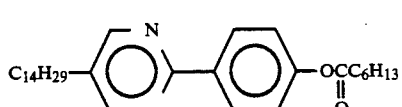 (178)
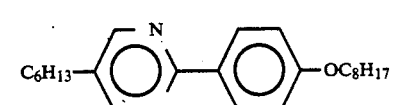 (179)
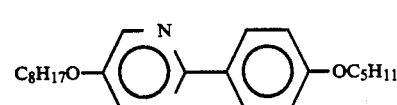 (180)
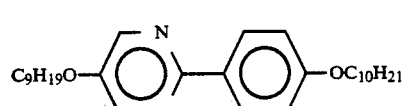 (181)

-continued
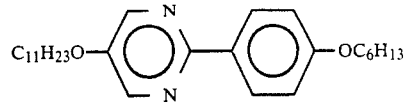 (182)
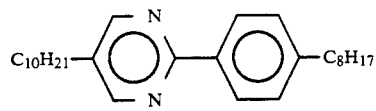 (183)
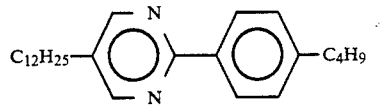 (184)
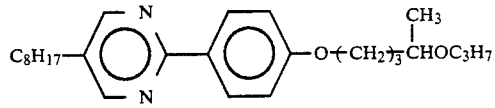 (185)
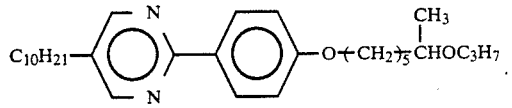 (186)
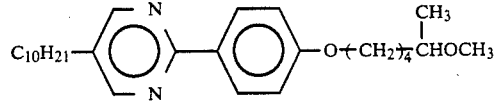 (187)
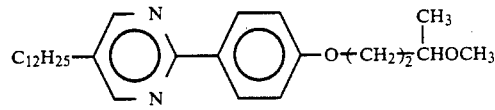 (188)
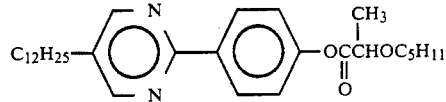 (189)
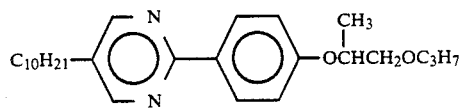 (190)
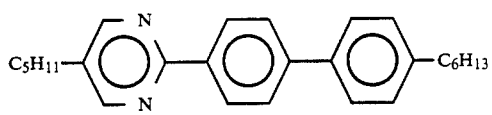 (191)
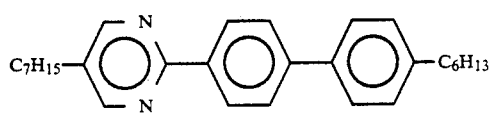 (192)
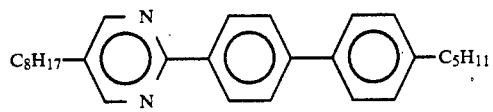 (193)
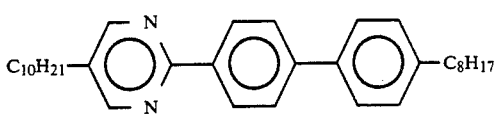 (194)

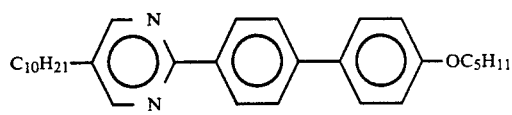 (195)
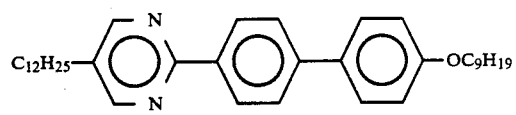 (196)
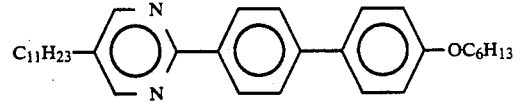 (197)
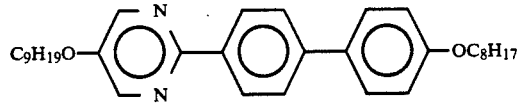 (198)
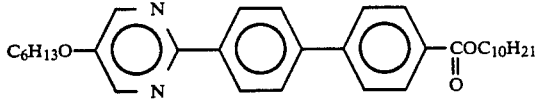 (199)
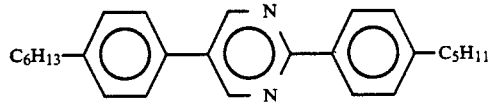 (200)
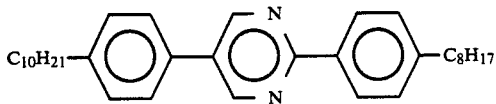 (201)
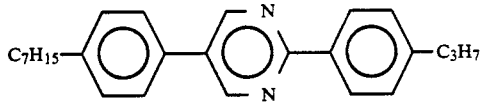 (202)
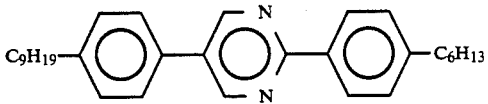 (203)
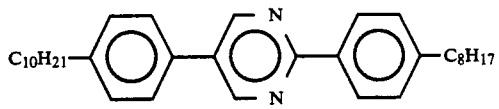 (204)
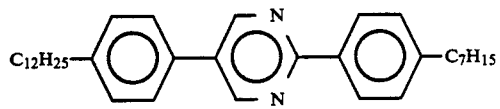 (205)
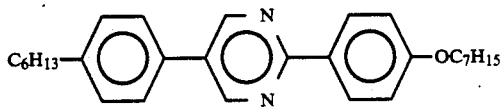 (206)
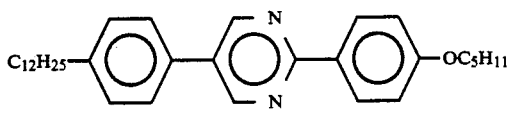 (207)

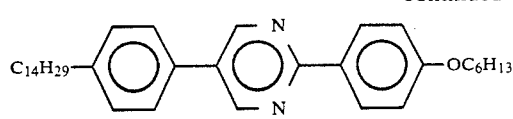 (208)
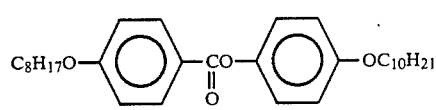 (209)
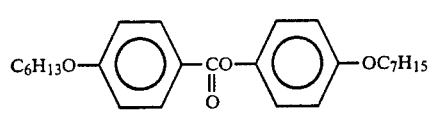 (210)
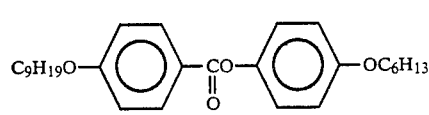 (211)
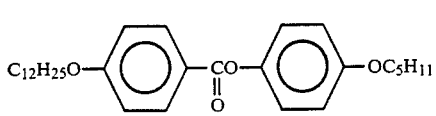 (212)
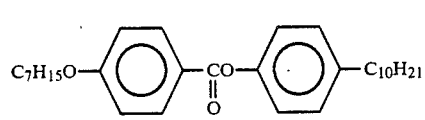 (213)
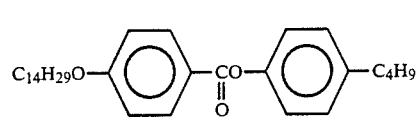 (214)
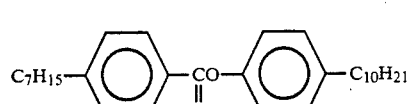 (215)
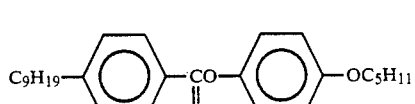 (216)
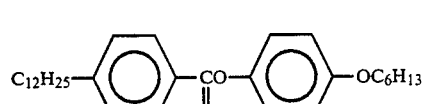 (217)
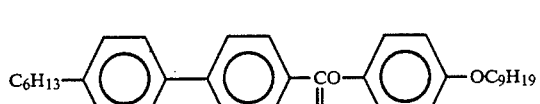 (218)
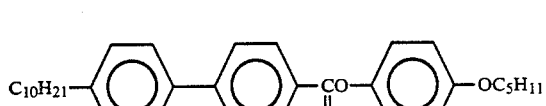 (219)
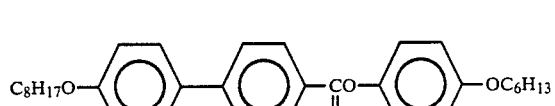 (220)

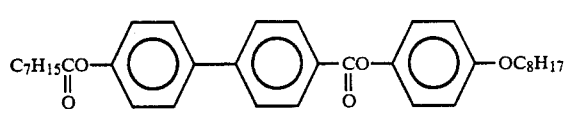 (221)
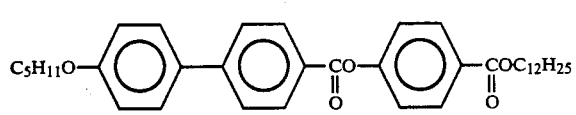 (222)
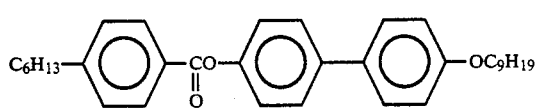 (223)
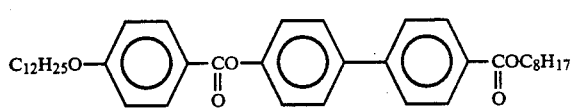 (224)
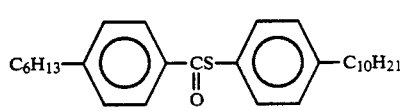 (225)
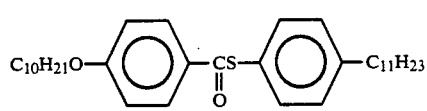 (226)
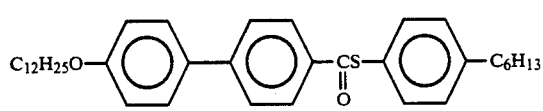 (227)
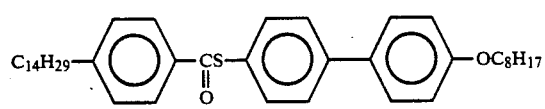 (228)
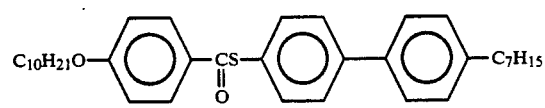 (229)
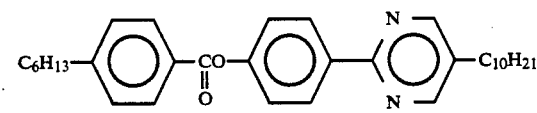 (230)
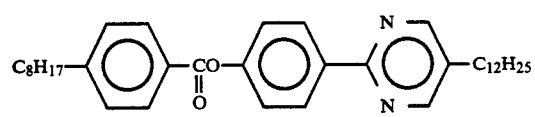 (231)
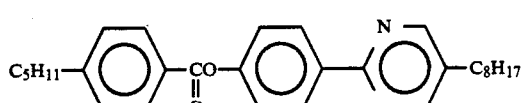 (232)
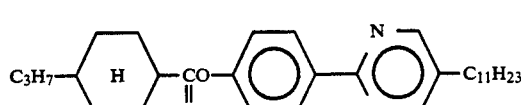 (233)

-continued
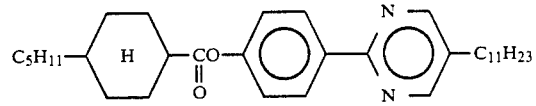 (234)
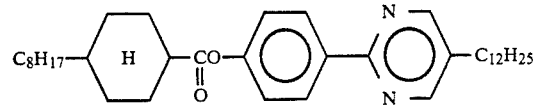 (225)
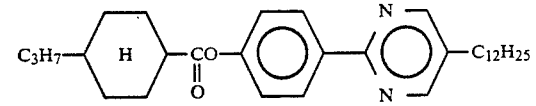 (236)
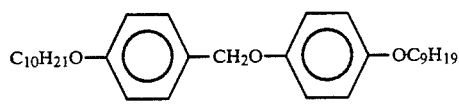 (237)
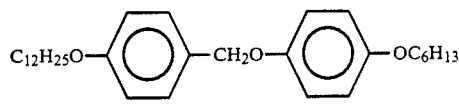 (238)
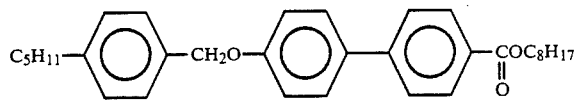 (239)
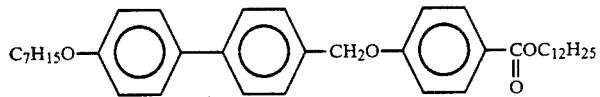 (240)
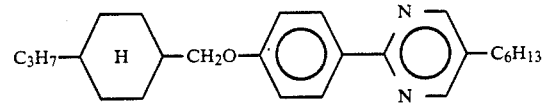 (241)
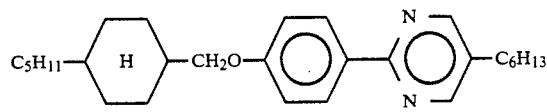 (242)
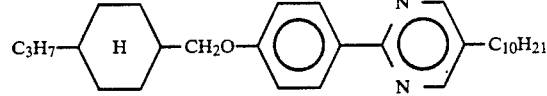 (243)
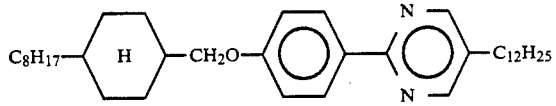 (244)
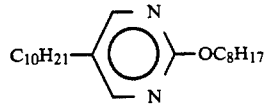 (245)
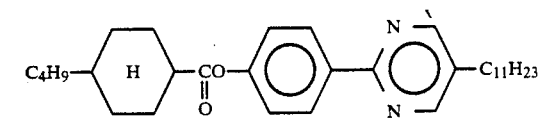 (246)

-continued

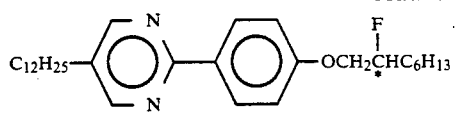 (247)

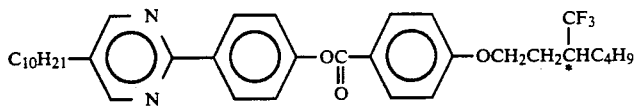 (248)

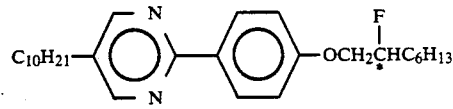 (249)

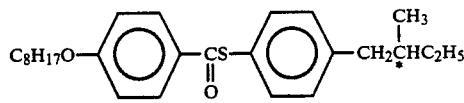 (250)

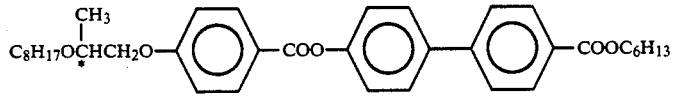 (251)

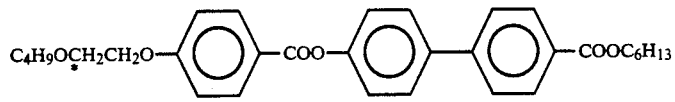 (252)

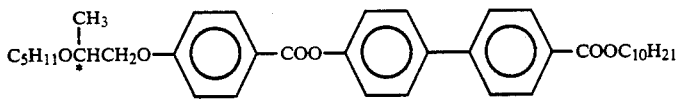 (253)

In formulating the liquid crystal composition according to the present invention, it is desirable to mix 1-500 wt. parts, preferably 2-100 wt. parts, of a compound represented by the formula (I) with 100 wt. parts of at least one species of another mesomorphic compound other than the compound represented by the formula (I).

Further, when two or more species of the compounds represented by the formula (I) are used, the two or more species of the compounds of the formula (I) may be used in a total amount of 1-500 wt. parts, preferably 2-100 wt. parts, per 100 wt. parts of at least one species of another mesomorphic compound other than the two or more species of the compounds of the formula (I).

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows a high-speed responsiveness, small temperature-dependence of response speed and wide drive voltage margin when contained in a device.

Particularly, in order to show a good alignment characteristic to form a uniform monodomain, the ferroelectric liquid crystal may show a phase transition series comprising isotropic phase-Ch phase (cholesteric phase)-SmA phase (smectic A phase)-SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P_\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments ($P_\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages as described above. First is that the response speed is quite fast. Second is that the orientation of the liquid crystal molecules shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

2-(4-decylphenyl)-5-(6-decyloxynaphthalene-2-yl)-1,3,4-thiadiazole (Example Compound No. 1-30) was synthesized through the following steps i) and ii).

Step i)

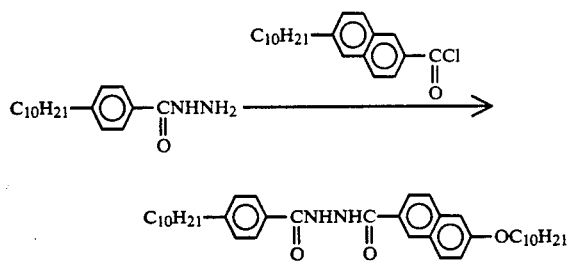

In a 50 ml-three-necked flask, 0.80 g (2.89 mM) of 4-decylbenzohydrazide, 1.10 g (3.17 mM) of 6-decyloxy-2-naphthoyl chloride and 20 ml of dioxane were placed and heated to 85°–90° C. under stirring. To the mixture, 1.10 ml (13.6 mM) of pyridine was added, followed by stirring by 1 hour at 85°–90° C. After the reaction, the reaction mixture was cooled and poured into 150 ml of iced water to precipitate a crystal. The crystal was recovered by filtration, followed by washing with water and further washing with methanol to obtain 1.69 g of N-4-decylbenzoyl-N'-(6-decyloxy-2-naphthoyl)hydrazine (Yield: 99.5%).

Step ii)

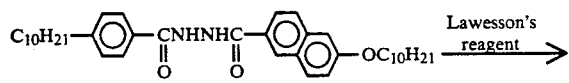

In a 50 ml-round-bottomed flask, 0.80 g (1.36 mM) of N-4-decylbenzoyl-N'-(6-decyloxy-2-naphthoyl)-hydrazine, 0.60 g (1.48 mM) of Lawesson's reagent and 12 ml of tetrahydrofuran were placed, followed by refluxing for 50 minutes under stirring. After the reaction, the reaction mixture was poured into a solution of 0.50 g of sodium hydroxide in 100 ml of iced water to precipitate a crystal. The crystal was recovered by filtration, followed by washing with water and further washing with methanol. The resultant crystal was recrystallized from a mixture solvent (toluene-methanol) and further recrystallized from tetrahydrofuran to obtain 0.51 g of 2-(4-decylphenyl)-5-(6-decyloxynaphthalene-2-yl)-1,3,4-thiadiazole (Yield: 64.0%).

Phase transition temperature (°C.)

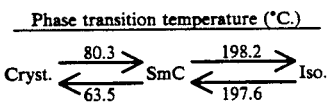

Herein, the respective symbols denote the following phases, Iso.: isotropic phase, SmC: smectic C phase, and Cryst.: crystal.

EXAMPLE 2

2-hexyl-5-(6-decyloxynaphthalene-2-yl)-1,3,4-thiadiazole (Example Compound No. 1-97) was synthesized through the following steps i) and ii).

Step i)

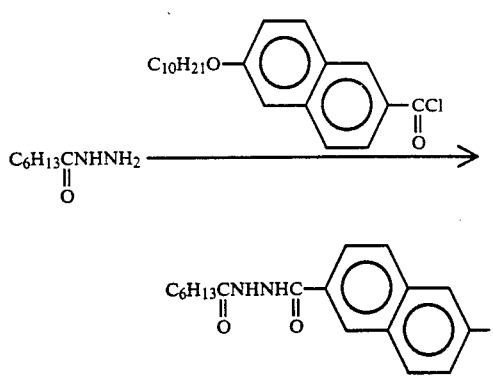

In a 50 ml-three-necked flask, 0.40 g (2.77 mM) of heptanohydrazide, 1.05 g (3.03 mM) of 6-decyloxy-2-naphthoyl chloride and 20 ml of dioxane were placed and heated to about 85° C. under stirring. To the mixture, 1.05 ml (13.0 mM) of pyridine was added, followed by heating to 90°–92° C. and stirring for 40 minutes at 90°–92° C. After the reaction, the reaction mixture was cooled and poured into 150 ml of iced water to precipitate a crystal. The crystal was recovered by filtration, followed by washing with water and further washing with acetone to obtain 1.21 g of N-heptanoyl-N'-(6-decyloxy-2-naphthoyl)hydrazine (Yield: 96.0%).

Step ii)

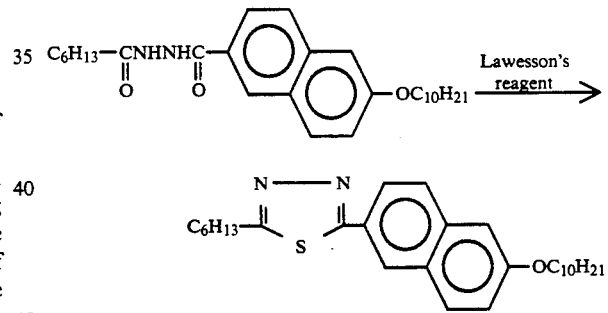

In a 50 ml-round-bottomed flask, 1.20 g (2.64 mM) of N-heptanoyl-N'-(6-decyloxy-2-naphthoyl)-hydrazine, 1.20 g (2.97 mM) of Lawesson's reagent and 15 ml of tetrahydrofuran were placed, followed by refluxing for 45 minutes under stirring. After the reaction, the reaction mixture was poured into a solution of 0.95 g of sodium hydroxide in 100 ml of iced water to precipitate a crystal. The crystal was recovered by filtration, followed by washing with water and purified by silica gel column chromatography (eluent: toluene). The resultant crystal was recrystallized from a mixture solvent (toluene-methanol) two times and further recrystallized from ethyl acetate and from toluene each once to obtain 0.54 g of 2-hexyl-5-(6-decyloxynaphthalene-2-yl)-1,3,4-thiadiazole (Yield: 45.2%).

Phase transition temperature (°C.)

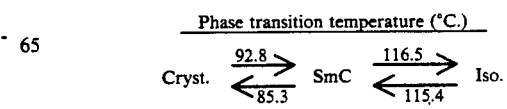

COMPARATIVE EXAMPLE 1

2-hexyl-5-(4-decyloxyphenyl)-1,3,4-thiadiazole was synthesized through the following reaction scheme.

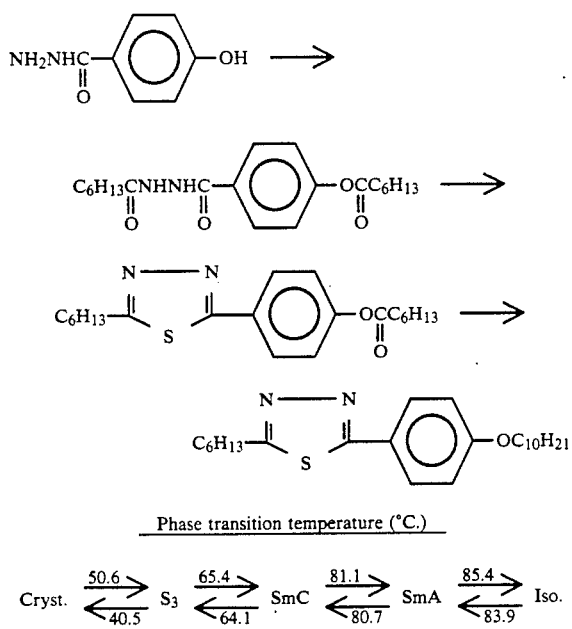

Phase transition temperature (°C.)

$$Cryst. \underset{40.5}{\overset{50.6}{\rightleftarrows}} S_3 \underset{64.1}{\overset{65.4}{\rightleftarrows}} SmC \underset{80.7}{\overset{81.1}{\rightleftarrows}} SmA \underset{83.9}{\overset{85.4}{\rightleftarrows}} Iso.$$

$S_3$: smectic phase (unidentified)
SmA: smectic A phase

As is apparent from Example 2 and Comparative Example 1, 2-hexyl-5-(6-decyloxynaphthalene-2-yl)-1,3,4-thiadiazole having an introduced naphthalene ring according to the present invention showed a smetic C phase in a wider temperature range.

EXAMPLE 3

2-(4-hexylphenyl)-5-(6-butoxynaphthalene-2-yl)-1,3,4-thiadiazole (Example Compound No. 1-9) was synthesized through the following steps i) to v).

Step i)

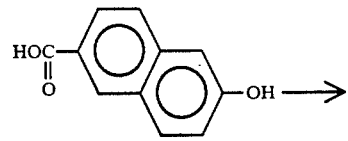

-continued

In a 30 ml-round-bottomed flask, 2.00 g (10.6 mM) of 6-hydroxy-2-naphthoic acid, 4.0 ml of acetic anhydride and two drops of concentrated sulfuric acid were placed, followed by heat-stirring for 1 hour at about 90° C. The reaction mixture was cooled to room temperature and poured into 100 ml of iced water to precipitate a crystal. The crystal was recovered by filtration, followed by washing with water and recrystallization from ethanol to obtain 1.48 g of 6-acetoxy-2-naphthoic acid (Yield: 60.5%).

2.0 ml of thionyl chloride and a drop of N,N-dimethylformamide were added to 1.45 g (6.30 mM) of 6-acetoxy-2-naphthoic acid, followed by refluxing for 30 minutes under stirring. Excessive thionyl chloride was distilled off from the above mixture under reduced pressure to obtain 6-acetoxy-2-naphthoyl chloride.

Step ii)

In a 100 ml-three-necked flask, 1.30 g (5.90 mM) of 4-hexylbenzohydrazide was placed and a solution of the above-prepared 6-acetoxy-2-naphthoyl chloride in 45 ml of dioxane was added thereto, followed by heating to about 83° C. To the mixture, 2.20 ml of pyridine was added under stirring, followed by stirring for 25 minutes at 83°-83.5° C. After the reaction, the reaction mixture was cooled on an iced water bath and poured into 300 ml of iced water to precipitate a crystal. The crystal was recovered by filtration, followed by washing with water and further washing with methanol to obtain 2.22 g of N-4-hexylbenzoyl-N'-(6-acetoxy-2-naphthoyl)hydrazine (Yield: 87.0%).

Step iii)

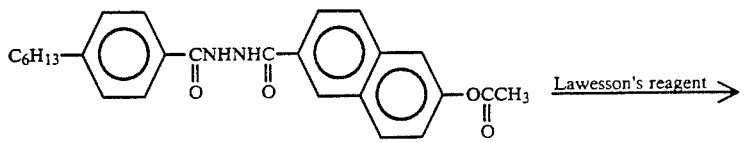

Step iii)

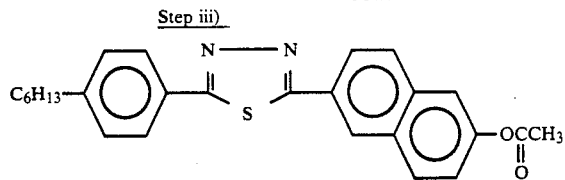

In a 100 ml-round-bottomed flask, 2.20 g (5.09 mM) of N-4-hexylbenzoyl-N'-(6-acetoxy-2-naphthoyl)hydrazine, 2.21 g (5.46 mM) of Lawesson's reagent and 30 ml of tetrahydrofuran were placed, followed by refluxing for 40 minutes under stirring. After the reaction, the reaction mixture was cooled on an iced water bath and poured into a solution of 1.69 g of sodium hydroxide in 200 ml of iced water to precipitate a crystal. The crystal was recovered by filtration and washed with water, followed by recrystallization from acetone to obtain 1.62 g of 2-(4-hexylphenyl)-5-(6-acetoxynaphthalene-2-yl)-1,3,4-thiadiazole (Example Compound No. 1-156) (Yield: 74.0 %).

Phase transition temperature (°C.)

Cryst. $\underset{\overset{\longrightarrow}{\longleftarrow 120.0}}{149.7}$ N. $\underset{\overset{\longrightarrow}{\longleftarrow 248.8}}{249.8}$ Iso.

N: nematic phase

Step iv)

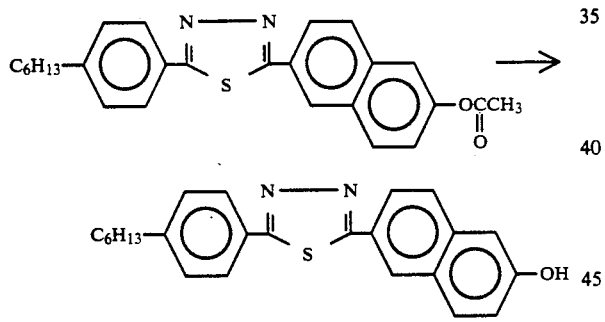

0.62 g (9.39 mM) of potassium hydroxide was dissolved in 30 ml of ethanol at 60°-65° C. To the solution, 1.50 g (3.48 mM) of 2-(4-hexylphenyl)-5-(6-acetoxynaphthalene-2-yl)-1,3,4-thiadiazole was added, followed by stirring for 10 minutes at 60°-65° C. The reaction mixture was poured into 100 ml of iced water and 0.83 ml of concentrated hydrochloric acid was added thereto to precipitate a crystal. The crystal was recovered by filtration and washed with water, followed by recrystallization from acetone to obtain 1.19 g of 2-(4-hexylphenyl)-5-(6-hydroxynaphthalene-2-yl)-1,3,4-thiadiazole (Yield: 87.9%).

Step v)

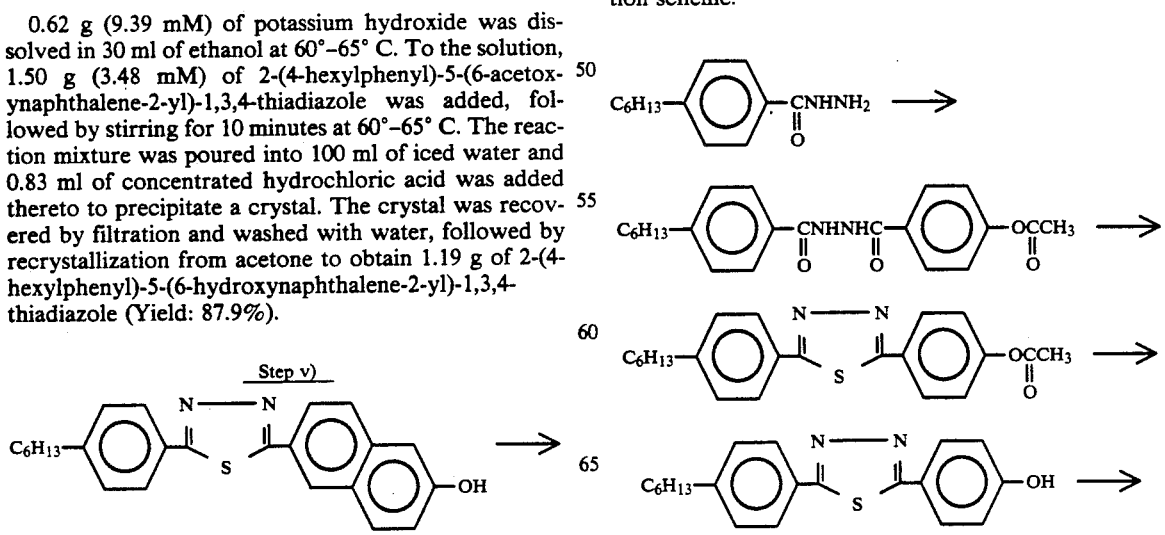

In a 20 ml-round-bottomed flask, 0.30 g (0.77 mM) of 2-(4-hexylphenyl)-5-(6-hydroxynaphthalene-2-yl)-1,3,4-thiadiazole, 0.08 g (1.21 mM) of potassium hydroxide was 4 ml of n-butanol were placed and dissolved at about 80° C. To the mixture, 0.12 ml (1.12 mM) of n-butyl bromide was added at 80° C. under stirring, followed by refluxing for 4 hours and 10 minutes under stirring. After the reaction, the reaction mixture was cooled on an iced water bath to precipitate a crystal. The crystal was recovered by filtration and washed with methanol. The resultant crystal was dissolved in toluene and washed with water, followed by drying with anhydrous sodium sulfate and distilling-off of the solvent. The residue was purified by silica gel column chromatography (eluent: toluene) and recrystallized from a mixture solvent (toluene-methanol) to obtain 0.25 g of 2-(4-hexylphenyl)-5(6-butoxynaphthalene-2-yl)-1,3,4-thiadiazole (Yield: 72.8%)

Phase transition temperature (°C.)

Cryst. $\underset{\overset{\longrightarrow}{\longleftarrow 58.1}}{79.5}$ SmC $\underset{\overset{\longrightarrow}{\longleftarrow 154.5}}{155.1}$ N. $\underset{\overset{\longrightarrow}{\longleftarrow 230.0}}{230.7}$ Iso.

COMPARATIVE EXAMPLE 2

2-(4-hexylphenyl)-5-(4-butoxyphenyl)-1,3,4-thiadiazole was synthesized through the following reaction scheme.

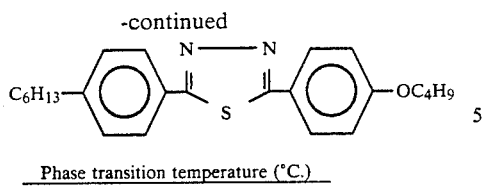

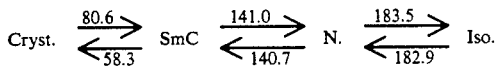

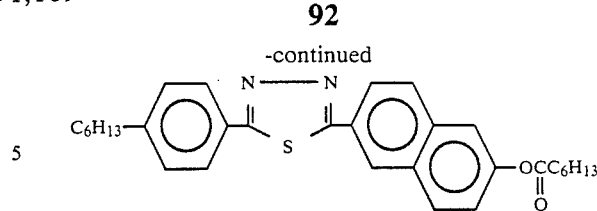

Cryst. $\underset{58.3}{\overset{80.6}{\rightleftarrows}}$ SmC $\underset{140.7}{\overset{141.0}{\rightleftarrows}}$ N. $\underset{182.9}{\overset{183.5}{\rightleftarrows}}$ Iso.

As is apparent from Example 3 and Comparative Example 2, 2-(4-hexylphenyl)-5-(6-butoxynaphthalene-2-yl)-1,3,4-thiadiazole having a naphthalene ring introduced thereto according to the present invention showed a smectic C phase in a wider temperature range.

EXAMPLE 4

2-(4-hexylphenyl)-5-(6-heptanoyloxynaphthalene-2-yl)-1,3,4-thiadiazole (Example Compound No. 1-55) was synthesized through the following reaction scheme.

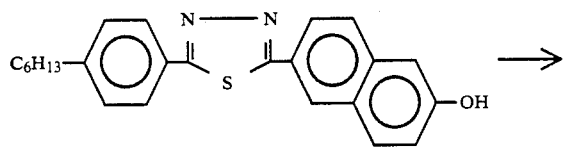

In a 30 ml-round-bottomed flask, 0.30 g (0.77 mM) of 2-(4-hexylphenyl)-5-(6-hydroxynaphthalene-2-yl)-1,3,4-thiadiazole was dissolved in 5 ml of pyridine. To the solution, 0.20 ml (1.29 mM) of heptanoyl chloride was added dropwise under cooling with an iced water bath and stirring. After the addition, the iced water bath was removed. Then, the mixture was stirred for 7 hours at room temperature and left standing overnight at room temperature. The resultant mixture was poured into 100 ml of iced water to precipitate a crystal. The crystal was recovered by filtration, washed with water and dissolved in toluene under heating, followed by drying with anhydrous sodium sulfate and distilling-off of the solvent. The residue was purified by silica gel column chromatography (eluent: toluene) and recrystallized from a mixture solvent (toluene-acetone) to obtain 0.27 g of 2-(4-hexylphenyl)-5-(6-heptanoyloxynaphthalene-2-yl)-1,3,4-thiadiazole (Yield: 69.8%)

Cryst. $\underset{73.3}{\overset{82.3}{\rightleftarrows}}$ SmC $\underset{199.3}{\overset{199.4}{\rightleftarrows}}$ N. $\underset{225.0}{\overset{225.2}{\rightleftarrows}}$ Iso.

EXAMPLE 5

A liquid crystal composition A was prepared by mixing the following compounds in respectively indicated proportions.

| Ex. Comp. No. | Structural formula | wt. parts |
|---|---|---|
| 173 | 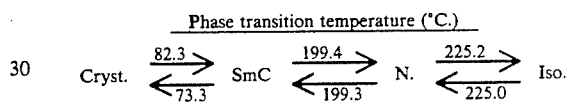 $C_6H_{13}O$—⬡—(N=N)—$C_8H_{17}$ | 46.14 |
| 174 | $C_9H_{19}O$—⬡—(N=N)—$C_8H_{17}$ | 23.07 |
| 245 | $C_8H_{17}O$—⬡—(N=N)—$C_{10}H_{21}$ | 11.54 |
| 233 | $C_3H_7$—(H)—CO—O—⬡—(N=N)—$C_{11}H_{23}$ | 3.56 |
| 246 | $C_4H_9$—(H)—CO—O—⬡—(N=N)—$C_{11}H_{23}$ | 3.56 |

-continued

| Ex. Comp. No. | Structural formula | wt. parts |
|---|---|---|
| 234 | $C_5H_{11}$—[cyclohexyl-H]—CO—O—[phenyl]—[pyrimidinyl-N,N]—$C_{11}H_{23}$ | 7.13 |
| 247 | $C_{12}H_{25}$—[pyrimidinyl-N,N]—[phenyl]—OCH$_2$*CHF—C$_6$H$_{13}$ | 2.50 |
| 249 | $C_{10}H_{21}$—[pyrimidinyl-N,N]—[phenyl]—OCH$_2$*CHF—C$_6$H$_{13}$ | 2.50 |

The liquid crystal composition A was further mixed with the following Example Compound N. 1-97 in the proportions indicated below to provide a liquid crystal composition B.

| Ex. Comp. No. | Structural formula | wt. parts |
|---|---|---|
| 1-97 | 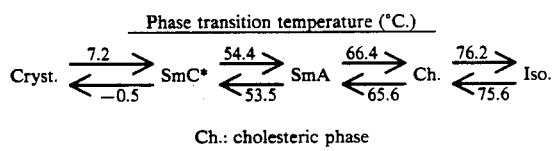 | 5 |
| | Composition A | 95 |

The liquid crystal composition B showed the following phase transition series.

Phase transition temperature (°C.)

$$\text{Cryst.} \underset{-0.5}{\overset{7.2}{\rightleftarrows}} \text{SmC*} \underset{53.5}{\overset{54.4}{\rightleftarrows}} \text{SmA} \underset{65.6}{\overset{66.4}{\rightleftarrows}} \text{Ch.} \underset{75.6}{\overset{76.2}{\rightleftarrows}} \text{Iso.}$$

Ch.: cholesteric phase

EXAMPLE 6

Two 0.7 mm-thick glass plates were provided and respectively coated with an ITO film to form an electrode for voltage application, which was further coated with an insulating layer of vapor-deposited SiO$_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 5 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polarization Ps and optical response time (time from voltage application until the transmittance change reaches 90% of the maximum under the application of a peak-to-peak voltage Vpp of 20 V in combination with right-angle cross-nicol polarizers).

The results are shown below.

| | 10° C. | 30° C. | 45° C. |
|---|---|---|---|
| Response time (μsec) | 488 | 232 | 135 |
| Ps (nC/cm$^2$) | 3.43 | 2.64 | 1.66 |

EXAMPLE 7

A liquid crystal composition C was prepared by mixing the following compounds in respectively indicated proportions.

| Ex. Comp. No. | Structural formula | wt. parts |
|---|---|---|
| 173 | C₆H₁₃O—⟨phenyl⟩—⟨pyrimidine⟩—C₈H₁₇ | 51.57 |
| 174 | C₉H₁₉O—⟨phenyl⟩—⟨pyrimidine⟩—C₈H₁₇ | 25.79 |
| 245 | C₈H₁₇O—⟨phenyl⟩—⟨pyrimidine⟩—C₁₀H₂₁ | 12.89 |
| 233 | C₃H₇—⟨cyclohexyl-H⟩—CO-O—⟨phenyl⟩—⟨pyrimidine⟩—C₁₁H₂₃ | 1.19 |
| 246 | C₄H₉—⟨cyclohexyl-H⟩—CO-O—⟨phenyl⟩—⟨pyrimidine⟩—C₁₁H₂₃ | 1.19 |
| 234 | C₅H₁₁—⟨cyclohexyl-H⟩—CO-O—⟨phenyl⟩—⟨pyrimidine⟩—C₁₁H₂₃ | 2.37 |
| 247 | C₁₂H₂₅—⟨pyrimidine⟩—⟨phenyl⟩—OCH₂*CHFC₆H₁₃ | 2.50 |
| 249 | C₁₀H₂₁—⟨pyrimidine⟩—⟨phenyl⟩—OCH₂*CHFC₆H₁₃ | 2.50 |

The liquid crystal composition C was further mixed with the following Example Compound No. 1-9 in the proportions indicated below to provide a liquid crystal composition D.

| Ex. Comp. No. | Structural formula | wt. parts |
|---|---|---|
| 1-9 | C₆H₁₃—⟨phenyl⟩—CH=N—S—N=CH—⟨naphthyl⟩—OC₄H₉ | 10 |
| | Composition C | 90 |

The liquid crystal composition D showed the following phase transition series.

Phase transition temperature (°C.)

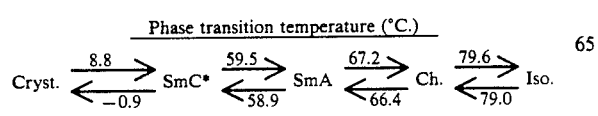

EXAMPLE 8

A ferroelectric liquid crystal device was prepared in the same manner as in Example 6 except for using the above liquid crystal composition D, and subjected to measurement of the magnitude of spontaneous polarization Ps and optical response time in the same manner as in Example 6.

The results are shown below.

| | 10° C. | 30° C. | 45° C. |
|---|---|---|---|
| Response time (μsec) | 804 | 307 | 180 |

| | 10° C. | 30° C. | 45° C. |
|---|---|---|---|
| -continued | | | |
| Ps (nC/cm$^2$) | 4.27 | 2.90 | 1.96 |

EXAMPLE 9

A liquid crystal composition E was prepared by mixing the following compounds in respectively indicated proportions.

| Ex. Comp. No. | Structural formula | wt. parts |
|---|---|---|
| 20 |  $C_{10}H_{21}O$—pyridine—phenyl—$O(CH_2)_5^*CH(CH_3)C_2H_5$ | 15 |
| 21 | $C_8H_{17}$—pyridine—phenyl—$O(CH_2)_3^*CH(CH_3)C_2H_5$ | 15 |
| 58 | $C_8H_{17}$—pyridine—phenyl—$O(CH_2)_3^*CH(CH_3)OC_5H_{11}$ | 10 |
| 89 | $C_{10}H_{21}$—pyridine—phenyl—$O(CH_2)_3^*CH(CH_3)OC_3H_7$ | 20 |
| 120 | $C_{10}H_{21}$—pyridine—phenyl—$OC(O)$—phenyl—$OCH_2^*CH(F)C_6H_{13}$ | 13 |
| 129 | $C_{10}H_{21}$—pyridine—phenyl—$OCH_2^*CH(F)C_8H_{17}$ | 7 |
| 236 | $C_3H_7$—cyclohexyl—$C(O)O$—phenyl—pyrimidine—$C_{12}H_{25}$ | 15 |
| 242 | $C_5H_{11}$—cyclohexyl—$CH_2O$—phenyl—pyrimidine—$C_6H_{13}$ | 5 |

The liquid crystal composition E was further mixed with the following Example Compounds in the proportions respectively indicated below to provide a liquid crystal composition F.

| Ex. Comp. No. | Structural formula | wt. parts |
|---|---|---|
| 1-3 | $C_4H_9$—phenyl—thiadiazole—naphthyl—$OC_5H_{11}$ | 3 |
| 1-25 | $C_9H_{19}$—phenyl—thiadiazole—naphthyl—$OC_{10}H_{21}$ | 2 |

| Ex. Comp. No. | Structural formula | wt. parts |
|---|---|---|
| | Composition E | 95 |

A ferroelectric liquid crystal device was prepared in the same manner as in Example 6 except that the liquid crystal composition F was injected into a cell. The measured values of the response time of the device were as follows.

| | 15° C. | 25° C. | 35° C. |
|---|---|---|---|
| Response time (μsec) | 141 | 95 | 81 |

COMPARATIVE EXAMPLE 3

A ferroelectric liquid crystal device was prepared in the same manner as in Example 6 except that the liquid crystal composition E prepared in Example 9 was injected into a cell. The measured values of the response time of the device were as follows.

| | 15° C. | 25° C. | 35° C. |
|---|---|---|---|
| Response time (μsec) | 155 | 100 | 80 |

EXAMPLE 10

A liquid crystal composition G was prepared in the same manner as in Example 9 except that the following Example Compounds were used instead of Examples Compounds Nos. 1-3 and 1-25 in respectively indicated proportions.

| Ex. Comp. No. | Structural formula | wt. parts |
|---|---|---|
| 1-10 | $C_6H_{13}$—⟨phenyl⟩—C(=N–N=)S—⟨naphthyl⟩—$OC_6H_{13}$ | 2 |
| 1-38 | $C_6H_{13}$—⟨phenyl⟩—C(=N–N=)S—⟨naphthyl⟩—$OCH_2\overset{*}{C}HC_6H_{13}$ (F) | 3 |
| 1-56 | $C_8H_{17}$—⟨phenyl⟩—C(=N–N=)S—⟨naphthyl⟩—$OCC_5H_{11}$ (∥O) | 2 |
| | Composition E | 93 |

A ferroelectric liquid crystal device was prepared in the same manner as in Example 6 except for using the composition G. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 128 | 88 | 77 |

EXAMPLE 11

A liquid crystal composition H was prepared in the same manner as in Example 9 except that the following Example Compounds were used instead of Example Compounds Nos. 1-3 and 1-25 in respectively indicated proportions.

| Ex. Comp. No. | Structural formula | wt. parts |
|---|---|---|
| 1-60 | $C_8H_{17}$—⟨phenyl⟩—C(=N–N=)S—⟨naphthyl⟩—$OC\overset{*}{C}HC_2H_5$ ($CH_3$, ∥O) | 2 |

-continued

| Ex. Comp. No. | Structural formula | wt. parts |
|---|---|---|
| 1-69 | 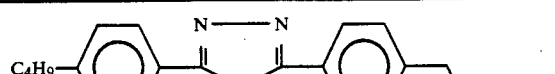 | 2 |
| 1-104 | | 2 |
| | Composition E | 94 |

A ferroelectric liquid crystal device was prepared in the same manner as in Example 6 except for using the composition H. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 132 | 90 | 82 |

EXAMPLE 12

A liquid crystal composition I was prepared in the same manner as in Example 9 except that the following Example Compounds were used instead of Example Compounds Nos. 1-3 and 1-25 in respectively indicated proportions.

A ferroelectric liquid crystal device was prepared in the same manner as in Example 6 except for using the composition I. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 132 | 95 | 80 |

EXAMPLE 13

A liquid crystal composition J was prepared in the same manner as in Example 9 except that the following Example Compounds were used instead of Example Compounds Nos. 1-3 and 1-25 in respectively indicated proportions.

| Ex. Comp. No. | Structural formula | wt. parts |
|---|---|---|
| 1-98 |  | 2 |
| 1-116 | | 2 |
| 1-120 | | 2 |
| 1-132 | | 3 |
| | Composition E | 91 |

| Ex. Comp. No. | Structural formula | wt. parts |
|---|---|---|
| 1-71 | C$_6$H$_{13}$—[pyrazine]—C(=S)—N=N—[naphthalene]—OC$_9$H$_{19}$ (thiadiazole linkage) | 2 |
| 1-72 | C$_8$H$_{17}$O—[C$_6$H$_3$F]—C(=S)—N=N—[naphthalene]—OC$_{10}$H$_{21}$ (thiadiazole linkage) | 1 |
| 1-83 | C$_8$H$_{17}$—[cyclohexyl-H]—C(=S)—N=N—[naphthalene]—C$_7$H$_{15}$ (thiadiazole linkage) | 2 |
| 1-108 | C$_{10}$H$_{21}$—C(=S)—N=N—[naphthalene]—OCH$_2$C*H(CH$_3$)OC$_3$H$_7$ (thiadiazole linkage) | 2 |
| Composition E | | 93 |

A ferroelectric liquid crystal device was prepared in the same manner as in Example 6 except for using the composition J. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 134 | 99 | 81 |

EXAMPLE 14

A liquid crystal composition K was prepared by mixing the following compounds in respectively indicated proportions.

| Ex. Comp. No. | Structural formula | wt. parts |
|---|---|---|
| 8 | C$_8$H$_{17}$O—[phenyl]—OC(=O)—[phenyl]—CH$_2$C*H(CH$_3$)C$_2$H$_5$ | 16 |
| 9 | C$_8$H$_{17}$O—[phenyl]—C(=O)S—[phenyl]—CH$_2$C*H(CH$_3$)C$_2$H$_5$ | 22.5 |
| 18 | C$_8$H$_{17}$O—[phenyl]—C(=O)O—[phenyl]—OCH$_2$C*H(CH$_3$)C$_2$H$_5$ | 64 |
| 23 | C$_8$H$_{17}$—[pyrimidine]—[phenyl]—O(CH$_2$)$_3$C*H(CH$_3$)C$_2$H$_5$ | 10 |

-continued

| Ex. Comp. No. | Structural formula | wt. parts |
| --- | --- | --- |
| 24 | $C_{11}H_{23}O-\text{[pyrimidine]}-\text{[phenyl]}-O(CH_2)_2\overset{*}{C}H(CH_3)C_2H_5$ | 10 |
| 43 | $C_{10}H_{21}O-\text{[phenyl]}-\underset{\underset{O}{\|\|}}{CS}-\text{[phenyl]}-OCH_2\overset{*}{C}H(CH_3)C_2H_5$ | 22.5 |
| 63 | $C_{10}H_{21}O\underset{\underset{O}{\|\|}}{C}-\text{[phenyl]}-\text{[phenyl]}-O\underset{\underset{O}{\|\|}}{C}-\text{[phenyl]}-OCH_2\overset{*}{C}H(CH_3)OC_5H_{11}$ | 15 |
| 87 | $C_6H_{13}O\underset{\underset{O}{\|\|}}{C}-\text{[phenyl]}-\text{[phenyl]}-O\underset{\underset{O}{\|\|}}{C}-\text{[phenyl]}-OCH_2\overset{*}{C}H(CH_3)OC_8H_{17}$ | 15 |
| 124 | $C_{12}H_{25}O-\text{[phenyl]}-\underset{\underset{O}{\|\|}}{C}O-\text{[phenyl]}-OCH_2\overset{*}{C}H(F)C_6H_{13}$ | 6.75 |
| 136 | $C_8H_{17}O-\text{[phenyl]}-\underset{\underset{O}{\|\|}}{C}O-\text{[phenyl]}-OCH_2\overset{*}{C}H(F)C_5H_{11}$ | 18.75 |
| 236 | $C_3H_7-\text{[cyclohexyl-H]}-\underset{\underset{O}{\|\|}}{C}O-\text{[phenyl]}-\text{[pyrimidine]}-C_{12}H_{25}$ | 20 |

The liquid crystal composition K was further mixed with the following Example Compounds in the proportions respectively indicated below to provide a liquid crystal composition L.

| Ex. Comp. No. | Structural formula | wt. parts |
| --- | --- | --- |
| 1-6 | $C_5H_{11}-\text{[phenyl]}-\text{[thiadiazole]}-\text{[naphthyl]}-OC_8H_{17}$ | 1 |
| 1-64 | $C_8H_{17}-\text{[phenyl]}-\text{[thiadiazole]}-\text{[naphthyl]}-C_8H_{17}$ | 1 |
| 1-73 | $C_5H_{11}-\text{[phenyl(F)]}-\text{[thiadiazole]}-\text{[naphthyl]}-OC_5H_{11}$ | 2 |

| Ex. Comp. No. | Structural formula | wt. parts |
|---|---|---|
| 1-106 | 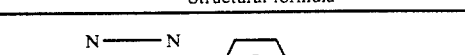 | 2 |
| | Composition K | 94 |

A ferroelectric liquid crystal device was prepared in the same manner as in Example 6 except for using the composition L. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

| | 15° C. | 25° C. | 35° C. |
|---|---|---|---|
| Response time (μsec) | 450 | 270 | 195 |

EXAMPLE 15

A liquid crystal composition M was prepared in the same manner as in Example 14 except that the following Example Compounds were used instead of Example Compounds Nos. 1-6, 1-64, 1-73 and 1-106 in respectively indicated proportions.

| Ex. Comp. No. | Structural formula | wt. parts |
|---|---|---|
| 1-44 | C7H15—⟨⟩—C(=N—N)S—C(naphthyl)—OCH2*CHOC3H7 with CH3 | 3 |
| 1-52 | C5H11—⟨⟩—C(=N—N)S—C(naphthyl)—OCC9H19 (O) | 1 |
| 1-103 | C8H17—C(=N—N)S—C(naphthyl)—OC6H13 | 2 |
| 1-111 | C8H17—C(=N—N)S—C(naphthyl)—OC8H17 | 2 |
| | Composition K | 92 |

COMPARATIVE EXAMPLE 4

A ferroelectric liquid crystal device was prepared in the same manner as in Example 6 except that the liquid crystal composition K prepared in Example 14 was injected into a cell. The measured values of the response time of the device were as follows.

| Response time (μsec) | 379 | 253 | 198 |
|---|---|---|---|

A ferroelectric liquid crystal device was prepared in the same manner as in Example 6 except for using the composition M. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

| | 15° C. | 25° C. | 35° C. |
|---|---|---|---|
| Response time (μsec) | 316 | 208 | 173 |

Further, when the device was driven, a clear switching action was observed, and good bistability was shown after the termination of the voltage application.

EXAMPLE 16

A liquid crystal composition N was prepared in the same manner as in Example 14 except that the following Example Compounds were used instead of Example Compounds Nos. 1-6, 1-64, 1-73 and 1-106 in respectively indicated proportions.

| Ex. Comp. No. | Structural formula | wt. parts |
|---|---|---|
| 1-15 | 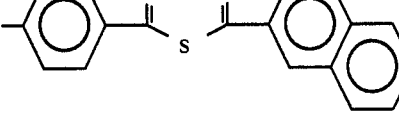 | 1 |
| 1-61 | 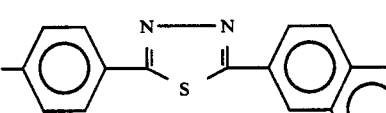 | 1 |
| 1-113 |  | 2 |
| 1-118 | 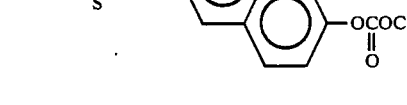 | 3 |
| Composition K | | 93 |

A ferroelectric liquid crystal device was prepared in the same manner as in Example 6 except for using the composition N. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

| | 15° C. | 25° C. | 35° C. |
|---|---|---|---|
| Response time (μsec) | 321 | 210 | 176 |

Further, when the device was driven, a clear switching action was observed, and good bistability was shown after the termination of the voltage application.

EXAMPLE 17

A liquid crystal composition O was prepared in the same manner as in Example 14 except that the following Example Compounds were used instead of Example Compounds Nos. 1-6, 1-64, 1-73 and 1-106 in respectively indicated proportions.

| Ex. Comp. No. | Structural formula | wt. parts |
|---|---|---|
| 1-20 | 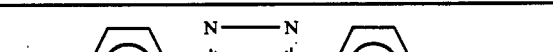 | 1 |
| 1-112 |  | 2 |

| Ex. Comp. No. | Structural formula | wt. parts |
|---|---|---|
| 1-119 | [structure: C₂H₅CH(CH₃)(CH₂)₂-thiazole-N=N-naphthalene-C₈H₁₇] | 2 |
| 1-136 | [structure: C₇H₁₅-thiazole-N=N-naphthalene-COO-phenyl(CN)(CN)-OC₈H₁₇] | 1 |
| Composition K | | 94 |

A ferroelectric liquid crystal device was prepared in the same manner as in Example 6 except for using the composition O. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

|  | 15° C. | 25° C. | 35° C. |
|---|---|---|---|
| Response time (μsec) | 351 | 237 | 188 |

Further, when the device was driven, a clear switching action was observed, and good bistability was shown after the termination of the voltage application.

EXAMPLE 18

A liquid crystal composition P was prepared by mixing the following compounds in respectively indicated proportions.

| Ex. Comp. No. | Structural formula | wt. parts |
|---|---|---|
| 250 | C₈H₁₇O—⌬—COS—⌬—CH₂*CH(CH₃)C₂H₅ | 18 |
| 19 | C₁₂H₂₅O—⌬—COS—⌬—CH₂*CH(CH₃)C₂H₅ | 18 |
| 81 | C₈H₁₇O—⌬—COS—⌬—OCH₂*CH(CH₃)C₂H₅ | 8 |
| 11 | C₁₀H₂₁O—⌬—COS—⌬—OCH₂*CH(CH₃)C₂H₅ | 8 |
| 251 | C₈H₁₇O*CH(CH₃)CH₂O—⌬—COO—⌬—⌬—COOC₆H₁₃ | 12 |
| 252 | C₄H₉OCH₂CH₂O—⌬—COO—⌬—⌬—COOC₆H₁₃ | 12 |
| 253 | C₅H₁₁O*CH(CH₃)CH₂O—⌬—COO—⌬—⌬—COOC₁₀H₂₁ | 6 |

-continued

| Ex. Comp. No. | Structural formula | wt. parts |
|---|---|---|
| 170 | 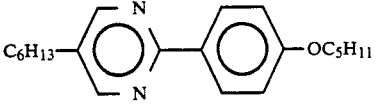 | 6 |
| 174 | 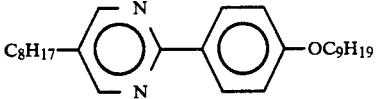 | 6 |
| 195 | 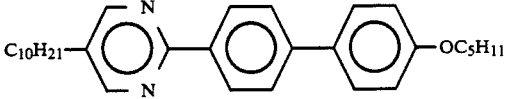 | 4 |
| 203 | 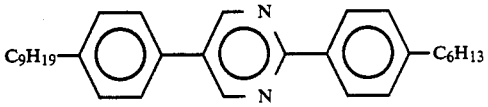 | 2 |

The liquid crystal composition P was further mixed with the following Example Compounds in the proportions respectively indicated below to provide a liquid crystal composition Q.

| Ex. Comp. No. | Structural formula | wt. parts |
|---|---|---|
| 1-11 | 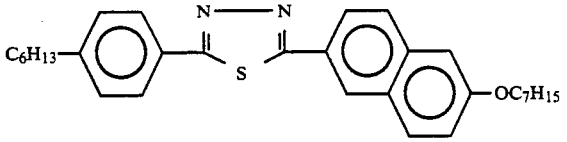 | 2 |
| 1-88 | 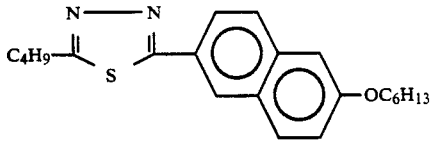 | 3 |
| 1-121 | 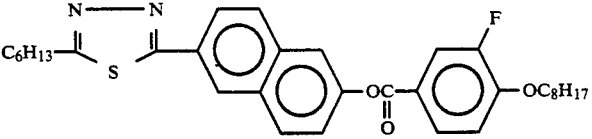 | 1 |
| | Composition P | 94 |

A ferroelectric liquid crystal device was prepared in the same manner as in Example 6 except for using the composition Q. The ferroelectric liquid crystal device was subjected to measurement of response time in the same manner as in Example 6, whereby the following results were obtained.

|  | 15° C. | 25° C. | 40° C. |
|---|---|---|---|
| Response time (μsec) | 1760 | 491 | 153 |

COMPARATIVE EXAMPLE 5

A ferroelectric liquid crystal device was prepared in the same manner as in Example 6 except that the liquid crystal composition P prepared in Example 18 was injected into a cell. The measured values of the response time of the device were as follows.

|  | 15° C. | 25° C. | 40° C. |
|---|---|---|---|
| Response time (μsec) | 1980 | 548 | 170 |

EXAMPLE 19

A liquid crystal composition R was prepared in the same manner as in Example 18 except that the following Example Compounds were used instead of Example Compounds Nos. 1-11, 1-88 and 1-121 in respectively indicated proportions.

| Ex. Comp. No. | Structural formula | wt. parts |
| --- | --- | --- |
| 1-142 | ![structure with C6H13CH(F)- thiazole-naphthalene-OCOC8H17] | 1 |
| 1-146 | ![structure with C8H17COO-phenyl-thiazole-naphthalene-OC5H11] | 1 |
| 1-153 | ![structure with C7H15-thiazole-naphthalene-C8H17] | 2 |
| | Composition P | 96 |

A ferroelectric liquid crystal device was prepared in the same manner as in Example 6 except for using the composition R. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

| | 10° C. | 25° C. | 40° C. |
| --- | --- | --- | --- |
| Response time (μsec) | 1790 | 496 | 151 |

Further, when the device was driven, a clear switching action was observed, and good bistability was shown after the termination of the voltage application.

As is apparent from the results shown in the above Examples 9–19, the ferroelectric liquid crystal devices containing the liquid crystal compositions F to J, L to O, Q and R showed an improved low-temperature operation characteristic, a high-speed responsiveness, and a decreased temperature dependence of the response speed.

EXAMPLE 20

A blank cell was prepared in the same manner as in Example 6 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition I prepared in Example 12. The liquid crystal device was subjected to measurement of optical response time in the same manner as in Example 6. The results are shown below.

| | 15° C. | 25° C. | 35° C. |
| --- | --- | --- | --- |
| Response time (μsec) | 120 | 86 | 70 |

EXAMPLE 21

A blank cell was prepared in the same manner as in Example 6 except for omitting the SiO2 layer to form an alignment control layer composed of the polyimide resin layer alone on each electrode plate. A ferroelectric liquid crystal device was prepared by filling the blank cell with the liquid crystal composition I prepared in Example 12. The liquid crystal device was subjected to measurement of optical response time in the same manner as in Example 6. The results are shown below.

| | 15° C. | 25° C. | 35° C. |
| --- | --- | --- | --- |
| Response time (μsec) | 118 | 84 | 72 |

As is apparent from the above Examples 20 and 21, also in the cases of different device structures, the devices containing the ferroelectric liquid crystal composition I according to the present invention respectively provided a remarkably improved operation characteristic at a lower temperature and also a decreased temperature-dependence of the response speed similar to those in Example 12.

EXAMPLE 22

A commercially available ferroelectric liquid crystal ("CS-1014" available from Chisso K.K.) having a $\Delta\epsilon$ of nearly 0 ($\Delta\epsilon \approx -0.4$ (sine wave, 100 kHz)) and the following example compounds were mixed in the proportions respectively indicated below to prepare a liquid crystal composition S.

| Ex. Comp. No. | Structural formula | wt. parts |
|---|---|---|
| 1-5 | $C_5H_{11}$—⌬—(thiadiazole)—(naphthyl)—$OC_6H_{13}$ | 1 |
| 1-40 | $C_5H_{11}\overset{F}{\underset{*}{C}}HCH_2O$—⌬—(thiadiazole)—(naphthyl)—$OC_7H_{15}$ | 1 |
| 1-80 | $C_3H_7$—(cyclohexyl-H)—(thiadiazole)—(naphthyl)—$OC_4H_9$ | 2 |
| 1-101 | $C_7H_{15}$—(thiadiazole)—(naphthyl)—$OC_8H_{17}$ | 2 |
| CS-1014 | | 94 |

Ferroelectric liquid crystal devices were prepared in the same manner as in Example 6 except that the above liquid crystal CS1014 and the liquid crystal composition S were used respectively and the liquid crystal layer thicknesses were changed to 1.5 microns.

The above liquid crystal devices were subjected to measurement of a tilt angle under right angle cross nicols at 25° C. Then, the devices were subjected application of a ±8 V rectangular waveform at a frequency of 60 kHz, and the tilt angles were measured under the voltage application and microscopic observation. Under these conditions, the transmittances and contrast ratios were also measured. The results are shown below.

|  | CS-1014 | Composition S |
|---|---|---|
| Tilt angle (under right angle cross nicols) | 7 degrees | 7.6 degrees |
| Tilt angle (under application ±8V, 60 KHz) | 8.8 degrees | 12.8 degrees |
| Transmittance (under application ±8V, 60 KHz) | 7.8% | 11.9% |
| Contrast ratio (under application ±8V, 60 KHz) | 8:1 | 31:1 |

EXAMPLE 23

A liquid crystal composition T was prepared in the same manner as in Example 22 except that the following example compounds were used in the indicated proportions.

| Ex. Comp. No. | Structural formula | wt. parts |
|---|---|---|
| 1-51 | $C_4H_9$—⌬—(thiadiazole)—(naphthyl)—$OCC_6H_{13}$ (with C=O) | 1 |
| 1-90 | $C_4H_9$—(thiadiazole)—(naphthyl)—$OC_9H_{19}$ | 2 |

-continued

| Ex. Comp. No. | Structural formula | wt. parts |
|---|---|---|
| 1-109 | 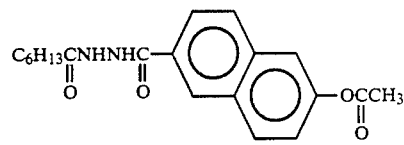 | 2 |
| 1-129 | | 2 |
| | CS-1014 | 93 |

Ferroelectric liquid crystal devices were prepared in the same manner as in Example 6 except that the above liquid crystal CS1014 and the liquid crystal composition T were used respectively and the liquid crystal layer thicknesses were changed to 1.5 microns.

The above liquid crystal devices were subjected to measurement of a tilt angle under right angle cross nicols at 25° C. Then, the devices were subjected application of a ±8 V rectangular waveform at a frequency of 60 kHz, and the tilt angles were measured under the voltage application and microscopic observation. Under these conditions, the transmittances and contrast ratios were also measured. The results are shown below.

|  | CS-1014 | Composition T |
|---|---|---|
| Tilt angle (under right angle cross nicols) | 7 degrees | 8.0 degrees |
| Tilt angle (under application ±8V, 60 KHz) | 8.8 degrees | 14.1 degrees |
| Transmittance (under application ±8V, 60 KHz) | 7.8% | 13.2% |
| Contrast ratio (under application ±8V, 60 KHz) | 8:1 | 38:1 |

The above results of Examples 22 and 23 show the addition of the mesomorphic compound example of the present invention to a liquid crystal CS 1014 having a Δε of nearly 0 provided a liquid crystal device showing improved display characteristics due to AC stabilization effect.

EXAMPLE 24

2-hexyl-5-(6-heptanoyloxynaphthalene-2-yl)-1,3,4-thiadiazole (Example Compound No. 1-163) was synthesized through the following steps i) to iii).

Step i)

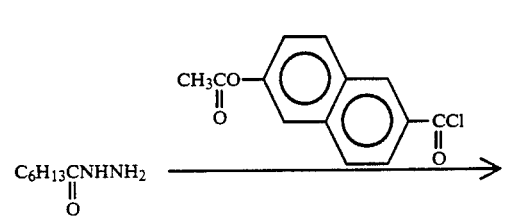

-continued
Step i)

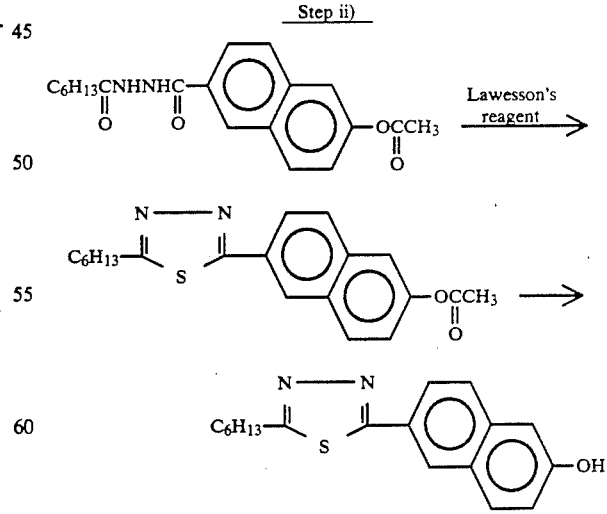

In a 200 ml-three-necked flask, 1.77 g (12.3 mM) of heptanohydrazide, 3,23 g (13.0 mM) of 6-acetoxy-2-naphthoyl chloride prepared in the same manner as in Example 3 and 90 ml of dioxane were placed and heated to about 80° C. To the mixture, 5.0 ml of pyridine was added at about 80° C. under stirring, followed by heating to 90°-92° C. and stirring for 1 hour at 90°-92° C. After the reaction, the reaction mixture was cooled on an iced water bath and poured into 350 ml of iced water to precipitate a crystal. The crystal was recovered by filtration, followed by washing with water and recrystallization from a mixture solvent (acetoneethyl acetate) to obtain 3.23 g of N-heptanoyl-N'-(6-acetoxy-2-naphthoyl)hydrazine (Yield: 75.4 %)

In a 100 ml-round-bottomed flask, 3.00 g (8.42 mM) of N-heptanoyl-N'-(6-acetoxy-2-naphthoyl)hydrazine, 3.83 g (9.47 mM) of Lawesson's reagent and 40 ml of tetrahydrofuran were placed, followed by refluxing for 1 hour under stirring. After the reaction, the reaction mixture was cooled on an iced water bath and poured into a solution of 3.00 g of sodium hydroxide in 250 ml of iced water to precipitate a crystal. The crystal was recovered by filtration and washed with water to obtain 2.92 g of 2-hexyl-5-(6-acetoxynaphthalene-2-yl)-1,3,4-thiadiazole (Yield: 97.9 %).

1.50 g (22.7 mM) of potassium hydroxide was dissolved in 72 ml of ethanol at 60°-65° C. To the solution, 2.90 g (8.18 mM) of 2-hexyl-5-(6-acetoxynaphthalene-2-yl)-1,3,4-thiadiazole was added, followed by stirring for 20 minutes at 60°-65° C. The reaction mixture was poured into 200 ml of iced water and 3 ml of concentrated hydrochloric acid was added thereto to precipitate a crystal. The crystal was recovered by filtration and washed with water to obtain 1.90 g of 2-hexyl-5-(6-hydroxynaphthalene-2-yl)-1,3,4-thiadiazole (Yield: 71.9 %).

Step iii)

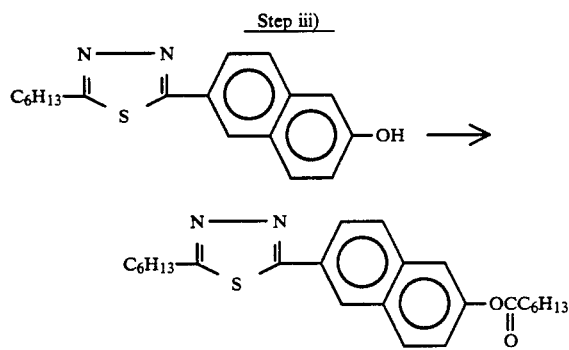

In a 30 ml-round-bottomed flask, 0.60 g (1.92 mM) of 2-hexyl-5-(6-hydroxynaphthalene-2-yl)-1,3,4-thiadiazole, 0.25 g (1.92 mM) of heptanoic acid were dissolved in 10 ml of dichloromethane. Under stirring, 0.39 g (1.89 mM) of N,N'-dicyclohexylcarbodiimide and 0.02 g of 4-pyrrolidinopyridine were successively added the above solution at room temperature, followed by stirring for 8 hours at room temperature. After the reaction, precipitated N,N'-dicyclohexylurea was filtered off and the filtrate was dried off under reduced pressure to obtain a solid. The solid was purified by silica gel column chromatography (eluent: toluene/ethyl acetate=3/1) and recrystallized from a mixture solvent (ethanol-ethyl acetate) to obtain 0.42 g of 2-hexyl-5-(6-heptanoyloxynaphthalene-2-yl)-1,3,4-thiadiazole (Yield: 81.5 %).

Phase transition temperature (°C.)

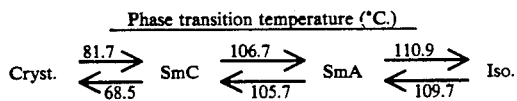

EXAMPLE 25

2-hexyl-5-(6-hexyloxynaphthalene-2-yl)-1,3,4-thiadiazole (Example Compound No. 1-157) was synthesized through the following reaction scheme.

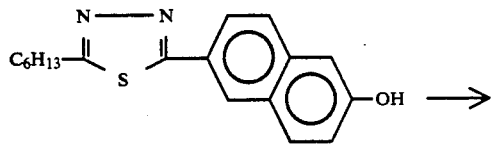

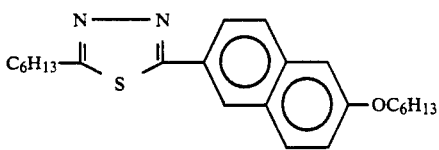

In a 50 ml-round-bottomed flask, 0.60 g (1.92 mM) of 2-hexyl-5-(6-hydroxynaphthalene-2-yl)-1,3,4-thiadiazole prepared in Step ii) of Example 24, 0.18 g (2.73 mM) of potassium hydroxide and 15 ml of butanol were placed and dissolved under heating. To the mixture, 0.53 g (2.50 mM) of hexyl iodide was added at about 100° C. under stirring, followed by refluxing for 6 hours under stirring. After the reaction, butanol was distilled off under reduced pressure, and water and ethyl acetate were added to the residue, followed by stirring. The resultant organic layer was washed with water, followed by drying with anhydrous sodium sulfate and distilling-off of the solvent to obtain a solid. The solid was purified by silica gel column chromatography (eluent: benzene) and recrystallized from a mixture solvent (ethyl acetate-ethanol) to obtain 0.27 g of 2-hexyl-5-(6-hexyloxynaphthalene-2-yl)-1,3,4-thiadiazole (Yield: 35.5 %).

Phase transition temperature (°C.)

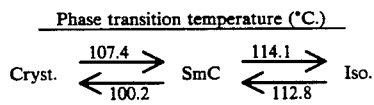

As described hereinabove, the ferroelectric liquid crystal composition according to the present invention provides a liquid crystal device which shows a good switching characteristic, an improved operation characteristic at a lower temperature and a decreased temperature dependence of response speed. Further, the liquid crystal composition according to the present invention provides a liquid crystal device which shows a remarkably improved display characteristic when used in a driving method utilizing AC stabilization.

We claim:

1. A mesomorphic compound represented by the following formula (I):

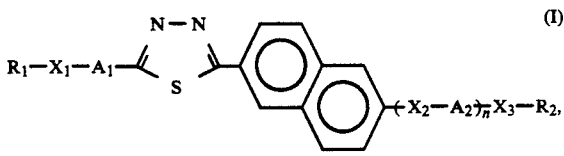

wherein $R_1$ and $R_2$ respectively denote an alkyl group having 1-16 carbon atoms capable of having a substituent;

$X_1$ and $X_3$ respectively denote a single bond, —O—, $$-O-, -O-\underset{O}{\overset{\parallel}{C}}-, -\underset{O}{\overset{\parallel}{C}}-O-, \text{ or } -\underset{O}{\overset{\parallel}{C}}-;$$

$X_2$ denotes a single bond,

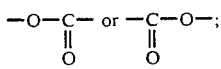

$A_1$ denotes a single bond,

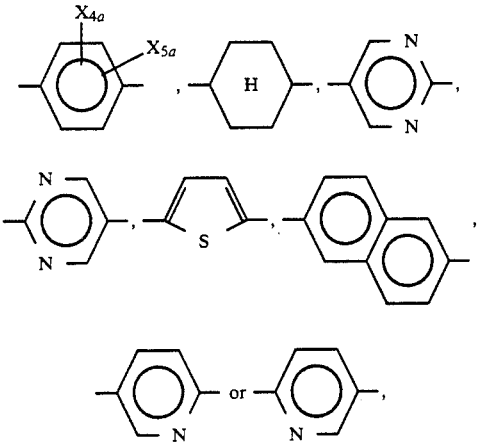

wherein $X_{4a}$ and $X_{5a}$ respectively denote hydrogen, fluorine, bromine, —CH$_3$ or —CF$_3$ with the proviso that $X_1$ always denotes a single bond when $A_1$ denotes a single bond;
$A_2$ denotes a single bond,

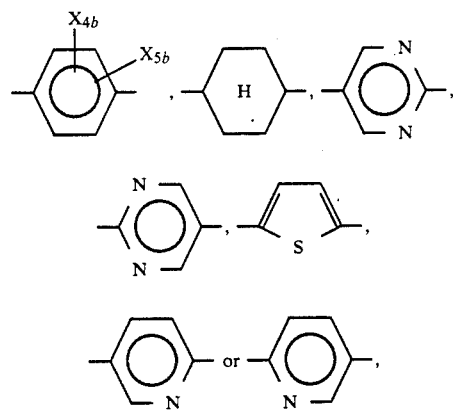

wherein $X_{4b}$ and $X_{5b}$ respectively denote hydrogen, fluorine or —CN;
and n is 0 or 1.

2. A mesomorphic compound according to claim 1, wherein $X_1$ denotes any one of a single bond, —O— and

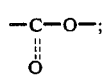

$X_2$ denotes any one of a single bond,

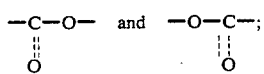

and
$X_3$ denotes any one of a single bond, —O—,

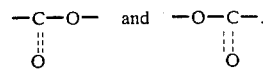

3. A mesomorphic compound according to claim 1, wherein $R_1$ and $R_2$ respectively denote any one of the following groups (i) to (iv):
(i) an n-alkyl group having 1-16 carbon atoms;
(ii)

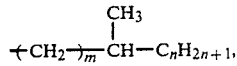

wherein m is an integer of 1-6 and n is an integer of 2-8;
(iii)

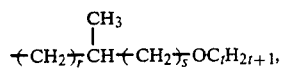

wherein r is an integer of 0-6, s is 0 or 1 and t is an integer of 1-12; and
(iv)

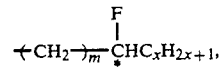

wherein m is 0 or 1 and x is an integer of 1-14.

4. A mesomorphic compound according to claim 3, wherein the group (i) is an n-alkyl group having 3-12 carbon atoms.

5. A mesomorphic compound according to claim 1, wherein $A_1$ denotes any one of

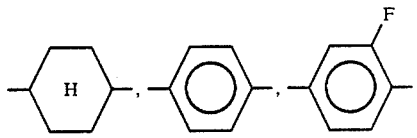

and a single bond; and $A_2$ denotes any one of

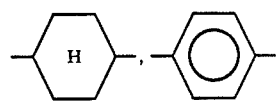

and a single bond.

6. A compound according to claim 1, of the formula:

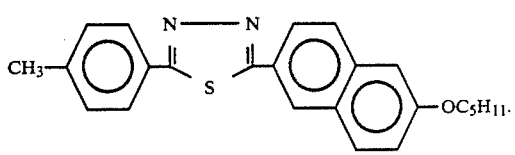

7. A compound according to claim 1, of the formula:

8. A compound according to claim 1, of the formula:

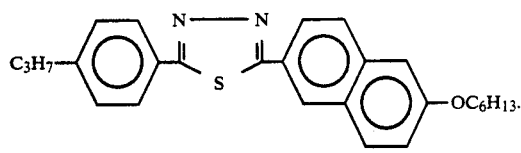

9. A compound according to claim 1, of the formula:

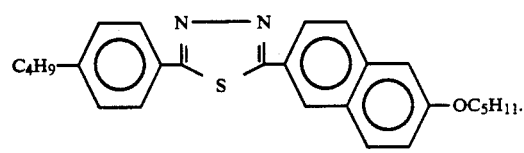

10. A compound according to claim 1, of the formula:

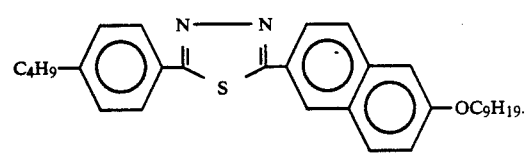

11. A compound according to claim 1, of the formula:

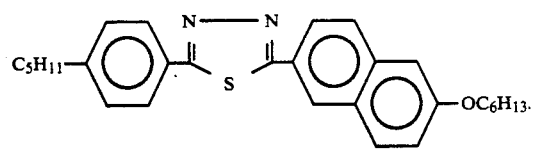

12. A compound according to claim 1, of the formula:

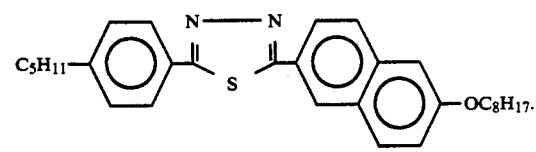

13. A compound according to claim 1, of the formula:

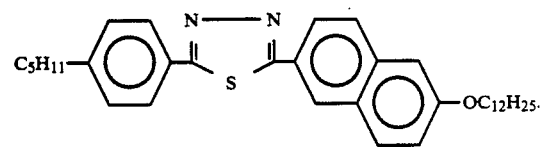

14. A compound according to claim 1, of the formula:

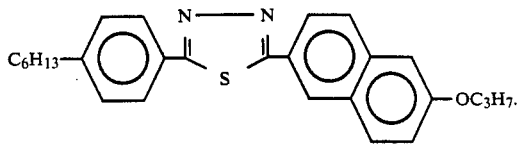

15. A compound according to claim 1, of the formula:

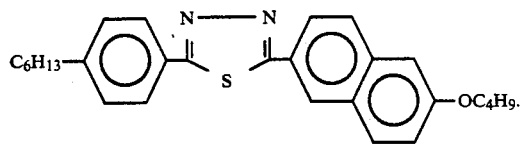

16. A compound according to claim 1, of the formula:

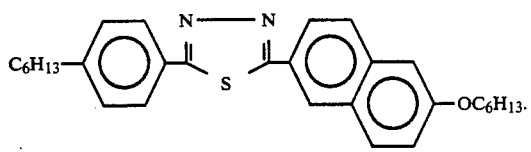

17. A compound according to claim 1, of the formula:

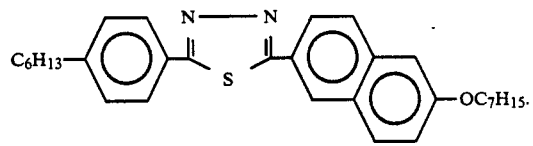

18. A compound according to claim 1, of the formula:

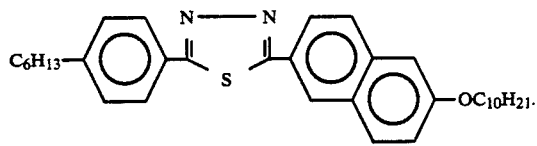

19. A compound according to claim 1, of the formula:

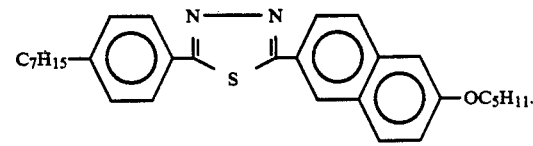

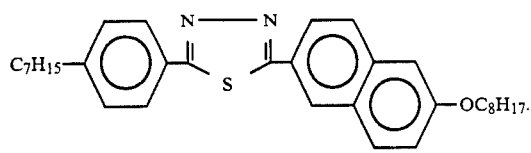

20. A compound according to claim 1, of the formula:

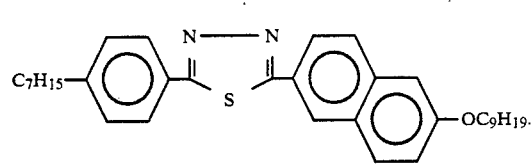

21. A compound according to claim 1, of the formula:

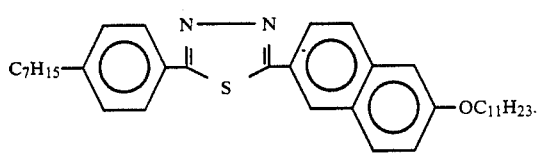

22. A compound according to claim 1, of the formula:

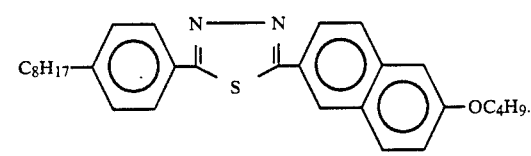

23. A compound according to claim 1, of the formula:

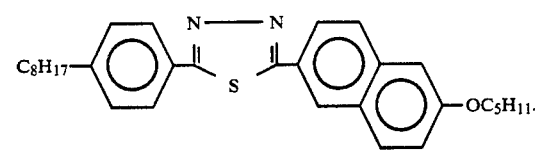

24. A compound according to claim 1, of the formula:

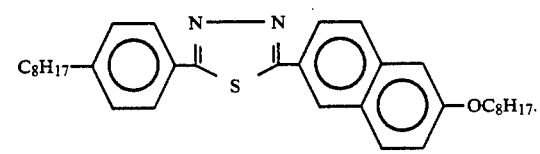

25. A compound according to claim 1, of the formula:

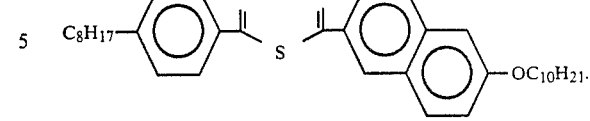

26. A compound according to claim 1, of the formula:

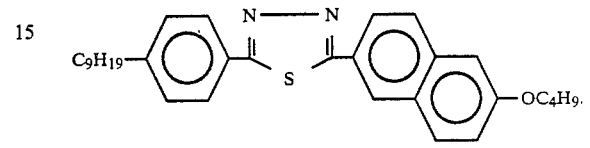

27. A compound according to claim 1, of the formula:

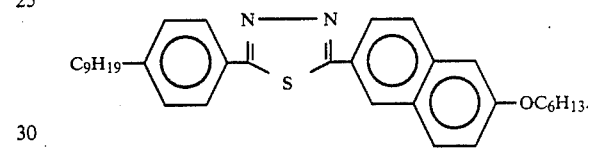

28. A compound according to claim 1, of the formula:

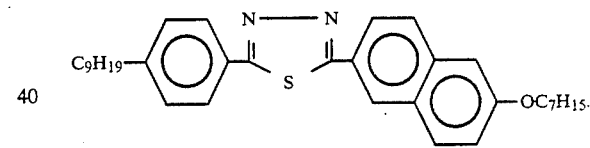

29. A compound according to claim 1, of the formula:

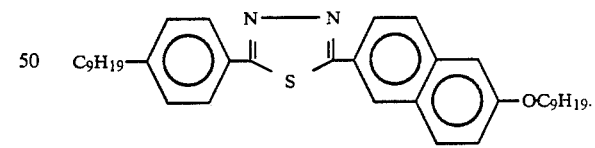

30. A compound according to claim 1, of the formula:

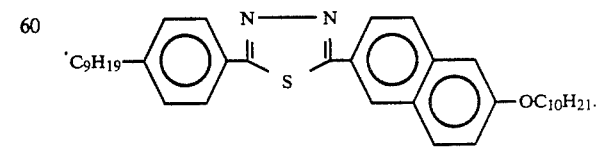

31. A compound according to claim 1, of the formula:

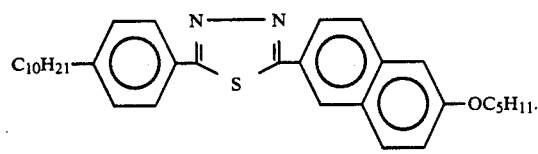

32. A compound according to claim 1, of the formula:

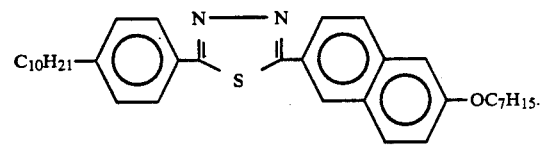

33. A compound according to claim 1, of the formula:

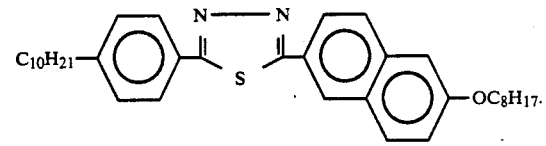

34. A compound according to claim 1, of the formula:

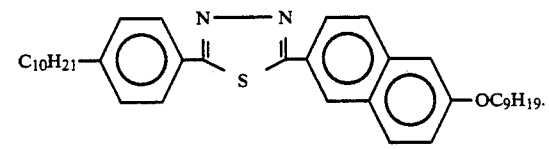

35. A compound according to claim 1, of the formula:

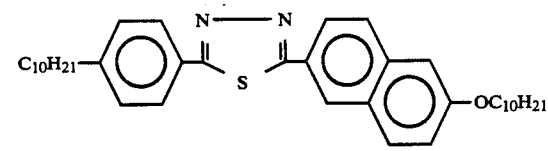

36. A compound according to claim 1, of the formula:

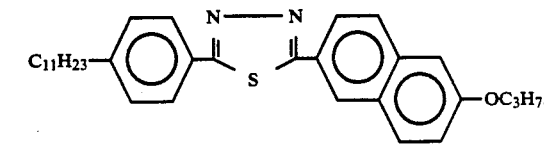

37. A compound according to claim 1, of the formula:

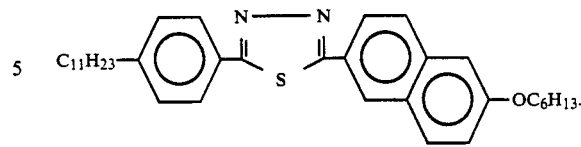

38. A compound according to claim 1, of the formula:

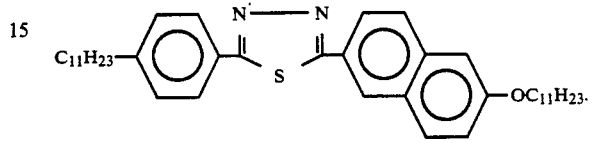

39. A compound according to claim 1, of the formula:

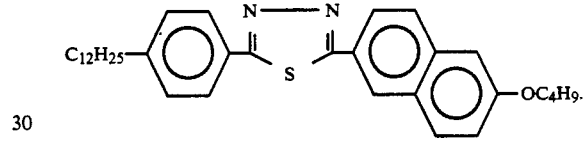

40. A compound according to claim 1, of the formula:

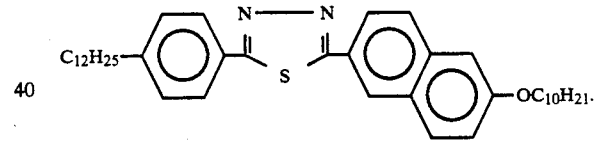

41. A compound according to claim 1, of the formula:

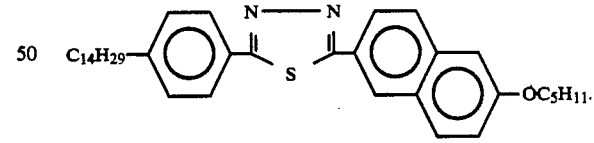

42. A compound according to claim 1, of the formula:

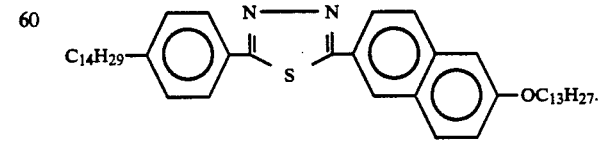

43. A compound according to claim 1, of the formula:

44. A compound according to claim 1, of the formula:
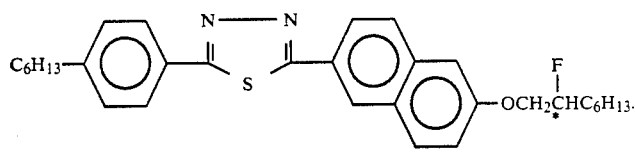
45. A compound according to claim 1, of the formula:
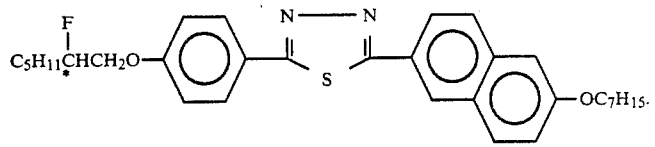
46. A compound according to claim 1, of the formula:
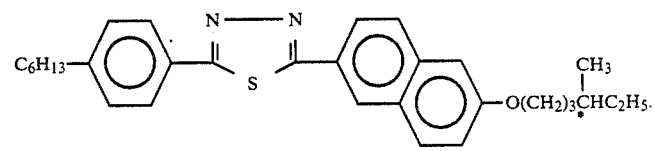
47. A compound according to claim 1, of the formula:
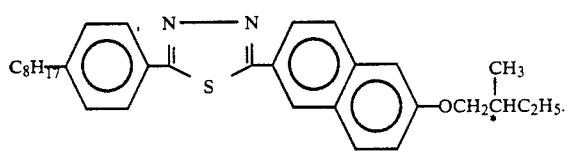
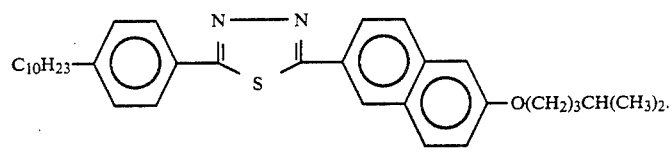
48. A compound according to claim 1, of the formula:
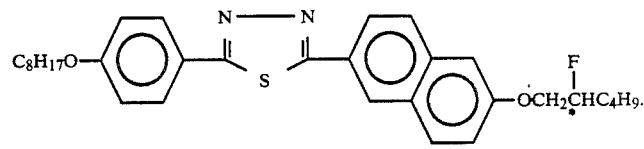
49. A compound according to claim 1, of the formula:
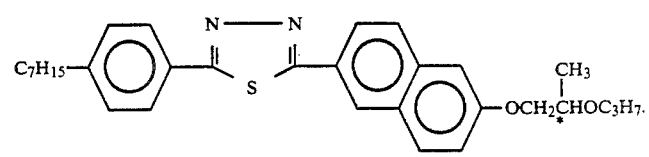
50. A compound according to claim 1, of the formula:

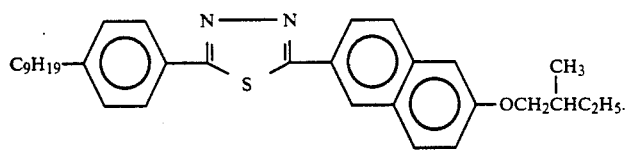

51. A compound according to claim 1, of the formula:

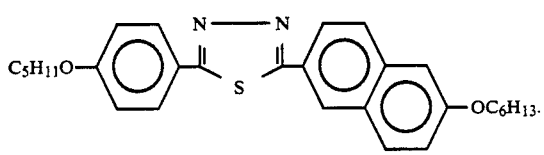

52. A compound according to claim 1, of the formula:

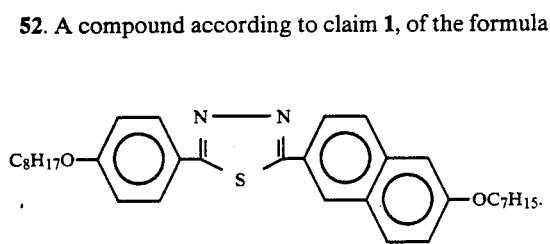

53. A compound according to claim 1, of the formula:

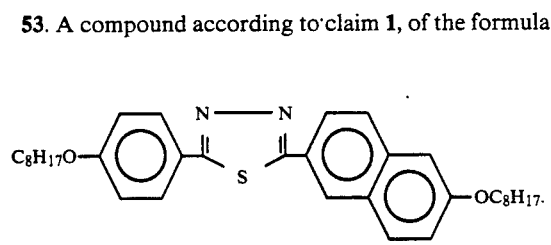

54. A compound according to claim 1, of the formula:

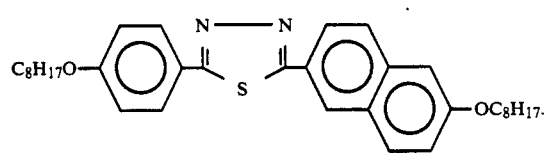

55. A compound according to claim 1, of the formula:

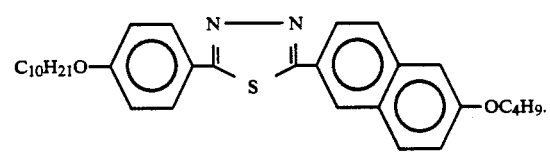

56. A compound according to claim 1, of the formula:

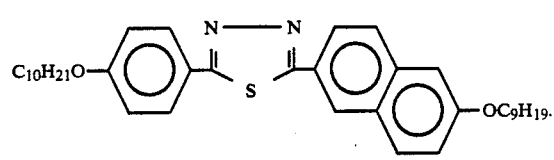

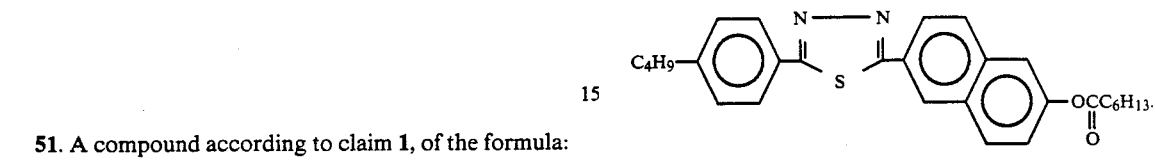

57. A compound according to claim 1, of the formula:

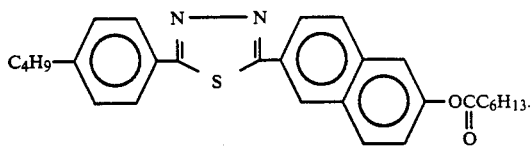

58. A compound according to claim 1, of the formula:

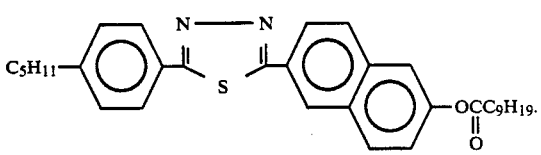

59. A compound according to claim 1, of the formula:

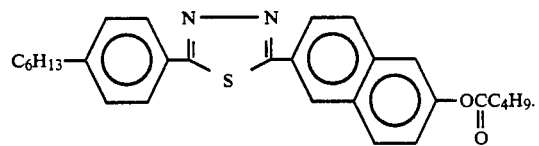

60. A compound according to claim 1, of the formula:

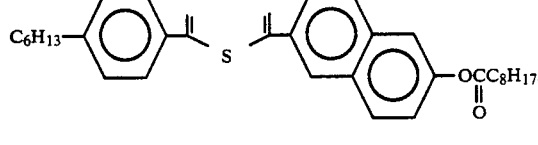

61. A compound according to claim 1, of the formula:

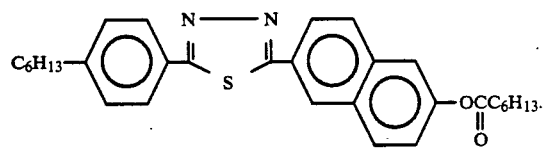

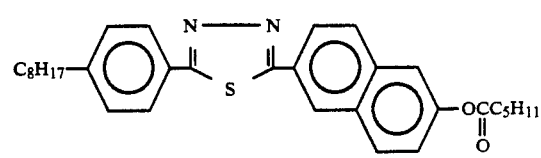

62. A compound according to claim 1, of the formula:

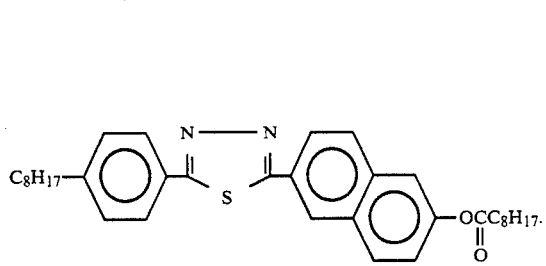

63. A compound according to claim 1, of the formula:

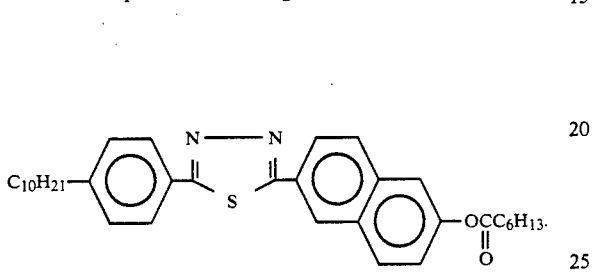

64. A compound according to claim 1, of the formula:

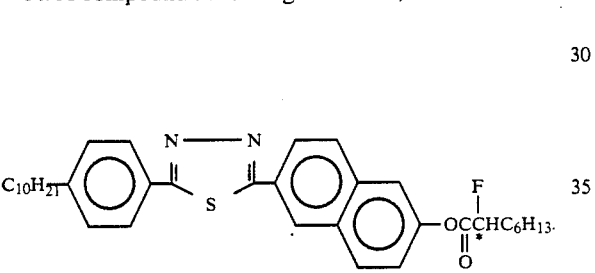

65. A compound according to claim 1, of the formula:

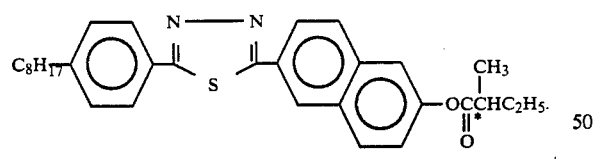

66. A compound according to claim 1, of the formula:

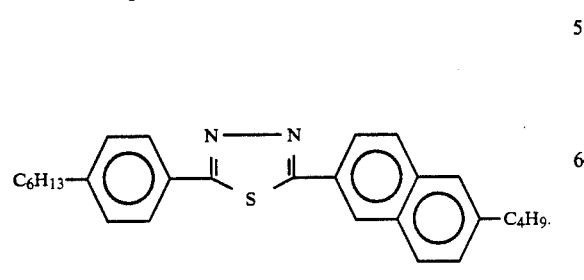

67. A compound according to claim 1, of the formula:

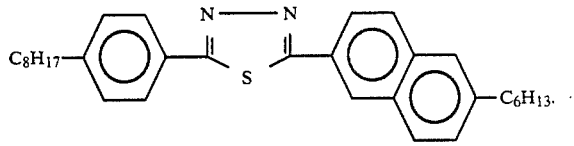

68. A compound according to claim 1, of the formula:

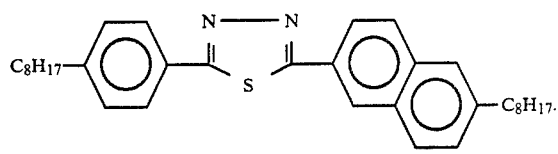

69. A compound according to claim 1, of the formula:

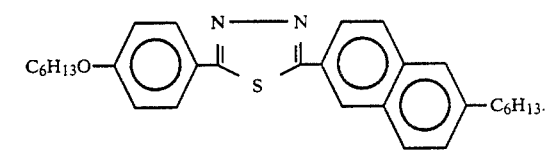

70. A compound according to claim 1, of the formula:

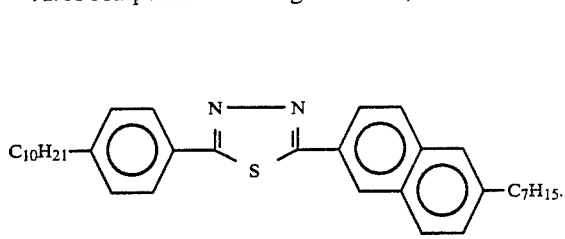

71. A compound according to claim 1, of the formula:

72. A compound according to claim 1, of the formula:

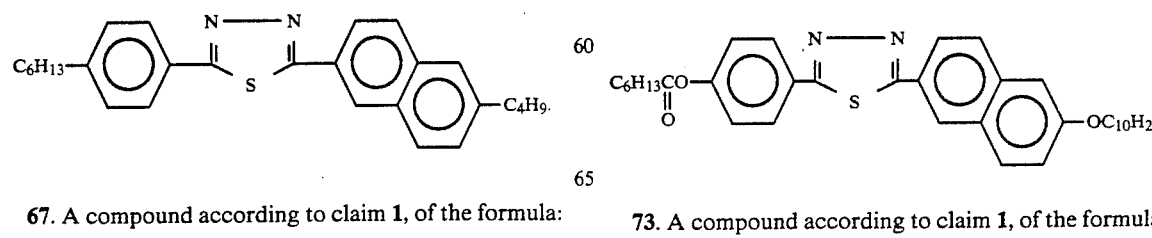

73. A compound according to claim 1, of the formula:

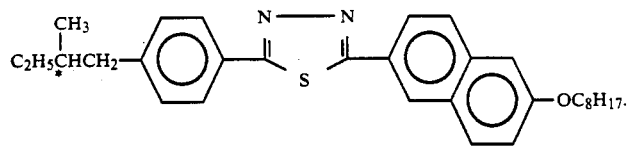

74. A compound according to claim 1, of the formula:

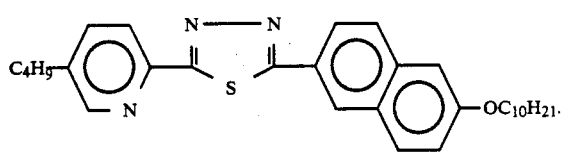

75. A compound according to claim 1, of the formula:

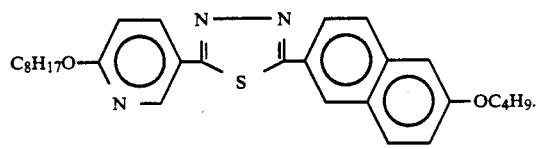

76. A compound according to claim 1, of the formula:

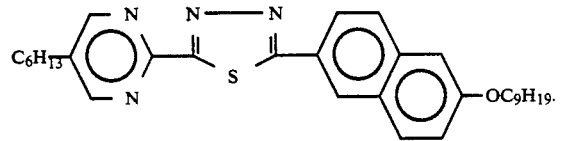

77. A compound according to claim 1, of the formula:

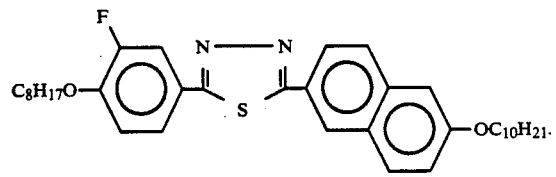

78. A compound according to claim 1, of the formula:

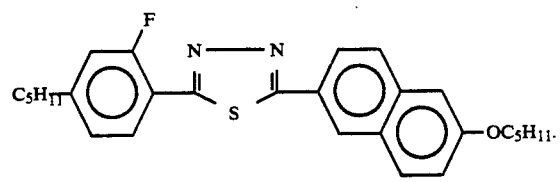

79. A compound according to claim 1, of the formula:

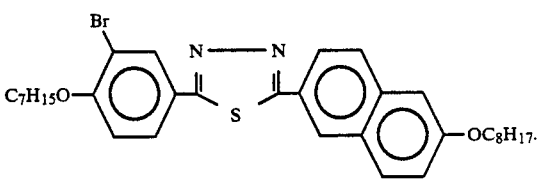

80. A compound according to claim 1, of the formula:

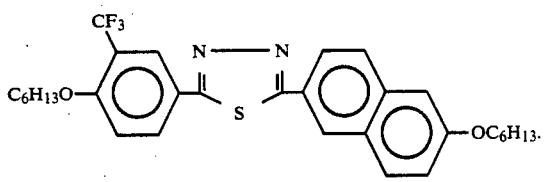

81. A compound according to claim 1, of the formula:

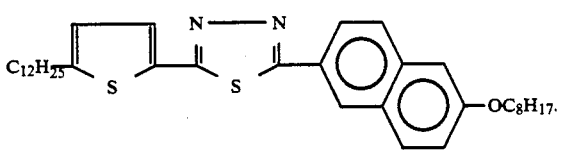

82. A compound according to claim 1, of the formula:

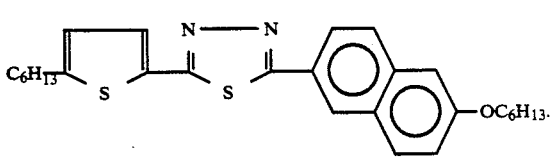

83. A compound according to claim 1, of the formula:

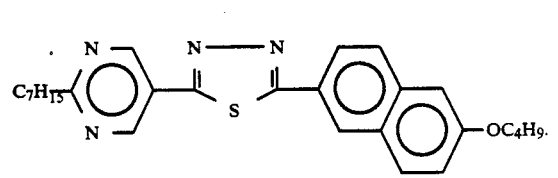

84. A compound according to claim 1, of the formula:

90. A compound according to claim 1, of the formula:

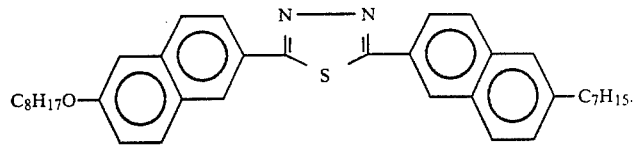

85. A compound according to claim 1, of the formula:

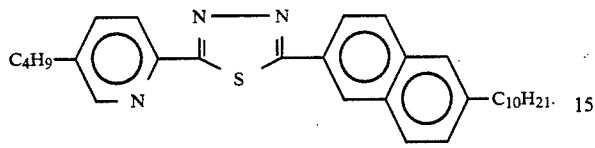

91. A compound according to claim 1, of the formula:

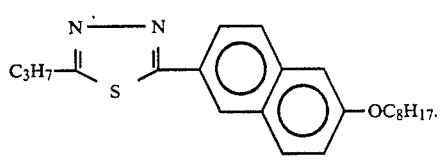

86. A compound according to claim 1, of the formula:

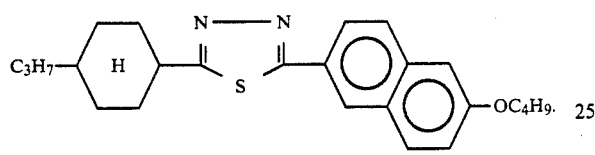

92. A compound according to claim 1, of the formula:

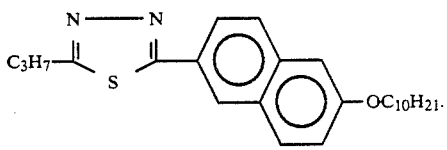

87. A compound according to claim 1, of the formula:

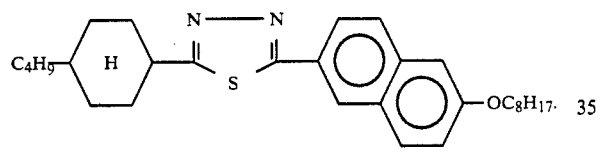

93. A compound according to claim 1, of the formula:

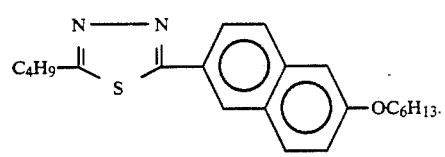

88. A compound according to claim 1, of the formula:

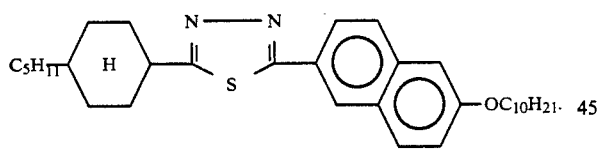

94. A compound according to claim 1, of the formula:

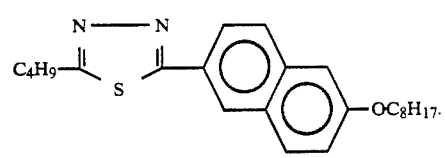

89. A compound according to claim 1, of the formula:

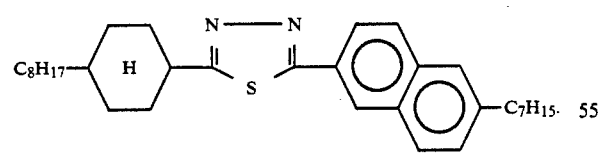

95. A compound according to claim 1, of the formula:

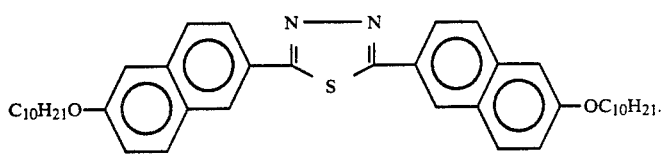

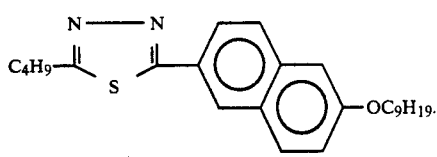

96. A compound according to claim 1, of the formula:

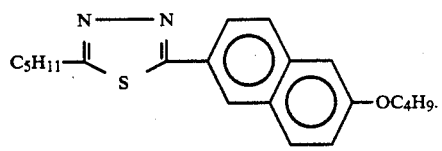

97. A compound according to claim 1, of the formula:

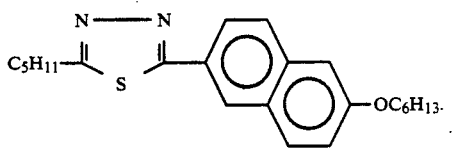

98. A compound according to claim 1, of the formula:

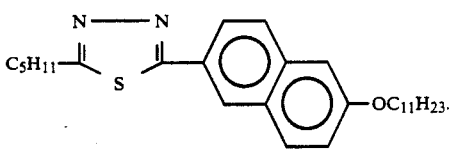

99. A compound according to claim 1, of the formula:

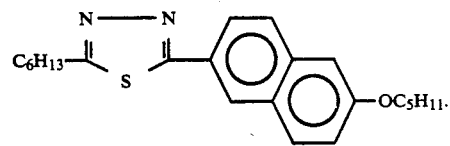

100. A compound according to claim 1, of the formula:

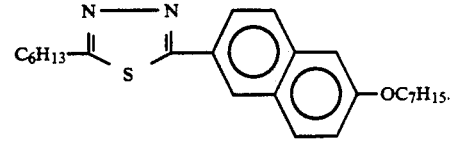

101. A compound according to claim 1, of the formula:

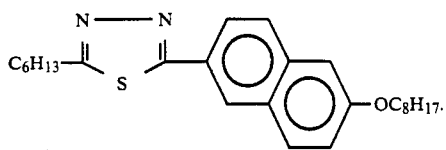

102. A compound according to claim 1, of the formula:

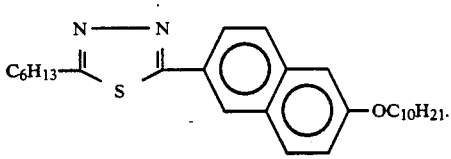

103. A compound according to claim 1, of the formula:

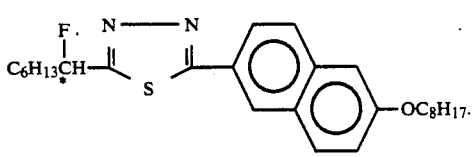

104. A compound according to claim 1, of the formula:

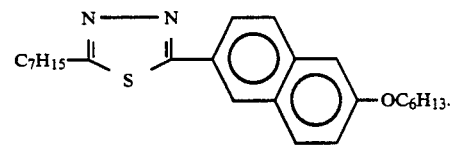

105. A compound according to claim 1, of the formula:

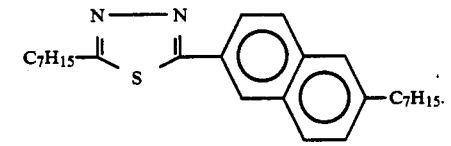

106. A compound according to claim 1, of the formula:

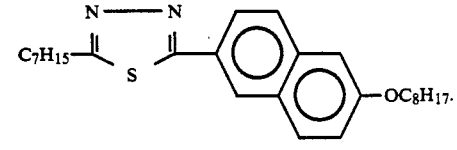

107. A compound according to claim 1, of the formula:

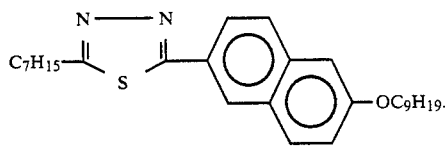

108. A compound according to claim 1, of the formula:

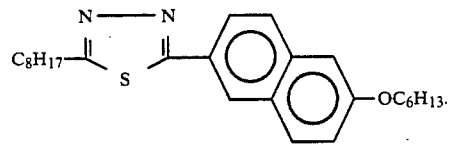

109. A compound according to claim 1, of the formula:

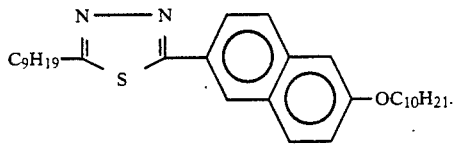

110. A compound according to claim 1, of the formula:

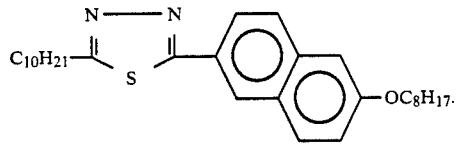

111. A compound according to claim 1, of the formula:

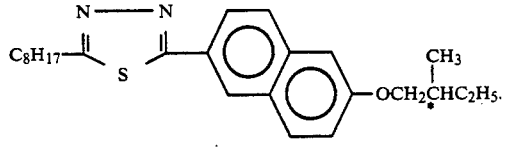

112. A compound according to claim 1, of the formula:

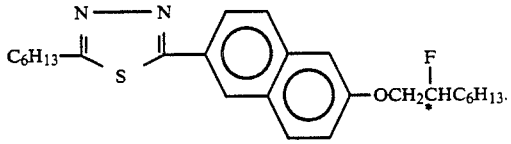

113. A compound according to claim 1, of the formula:

114. A compound according to claim 1, of the formula:

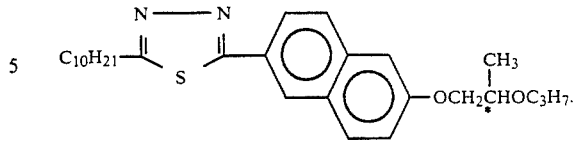

115. A compound according to claim 1, of the formula:

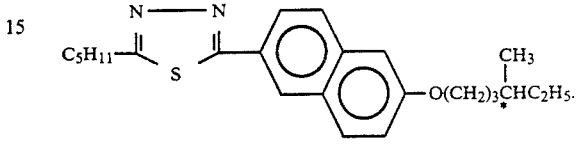

116. A compound according to claim 1, of the formula:

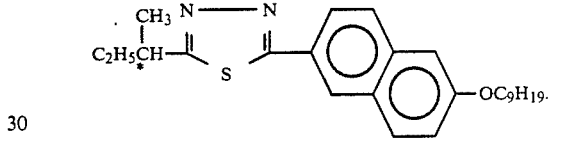

117. A compound according to claim 1, of the formula:

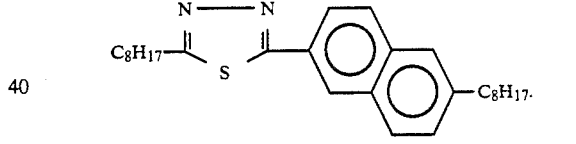

118. A compound according to claim 1, of the formula:

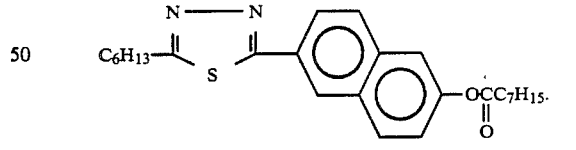

119. A compound according to claim 1, of the formula:

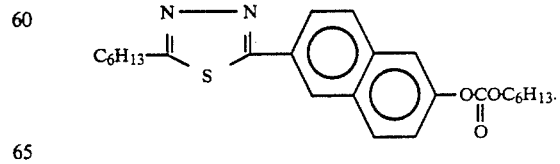

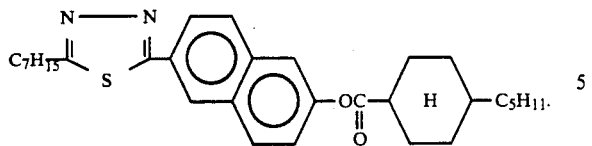

120. A compound according to claim 1, of the formula:

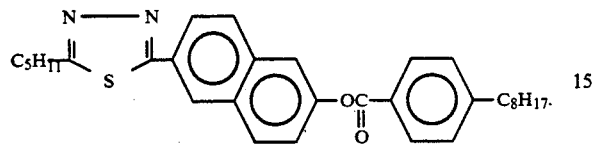

121. A compound according to claim 1, of the formula:

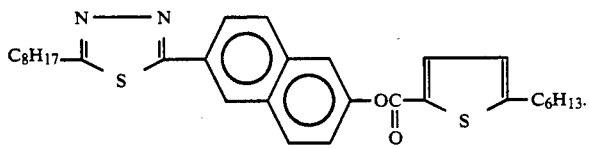

122. A compound according to claim 1, of the formula:

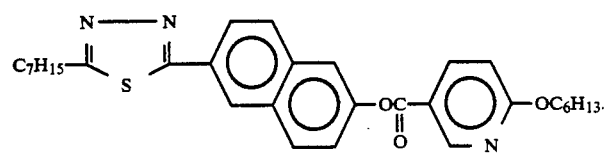

123. A compound according to claim 1, of the formula:

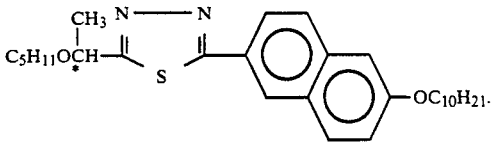

124. A compound according to claim 1, of the formula:

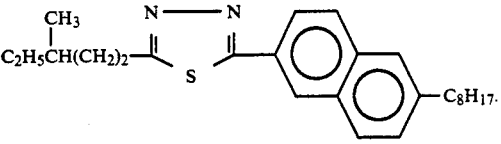

125. A compound according to claim 1, of the formula:

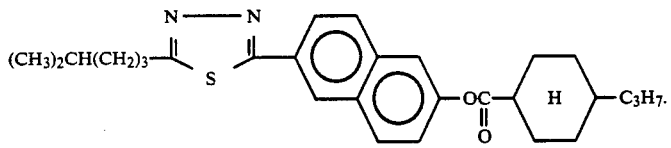

126. A compound according to claim 1, of the formula:

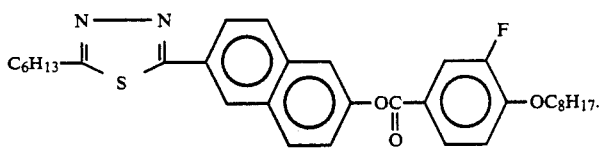

127. A compound according to claim 1, of the formula:

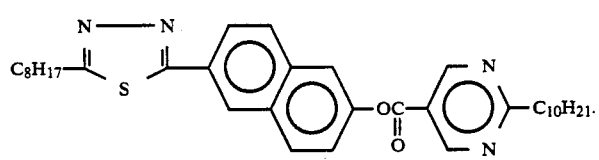

128. A compound according to claim 1, of the formula:

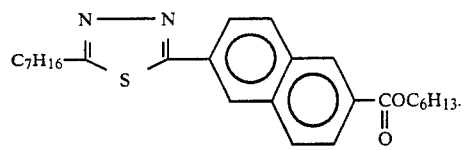

129. A compound according to claim 1, of the formula:

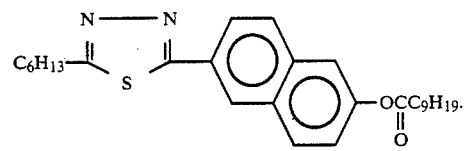

130. A compound according to claim 1, of the formula:

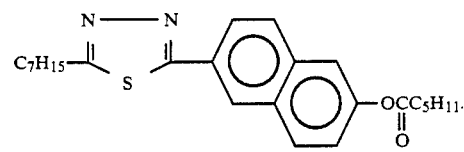

131. A compound according to claim 1, of the formula:

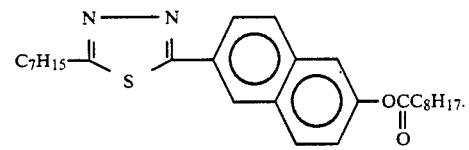

132. A compound according to claim 1, of the formula:

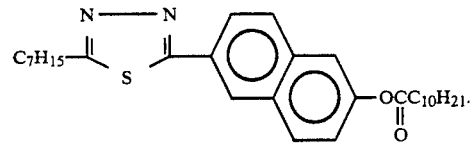

133. A compound according to claim 1, of the formula:

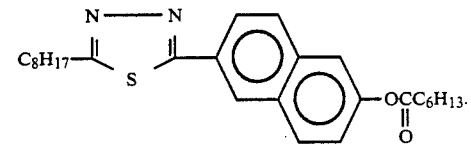

134. A compound according to claim 1, of the formula:

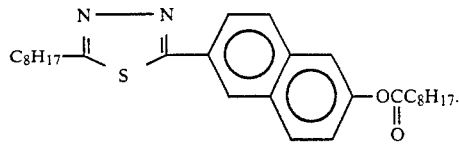

135. A compound according to claim 1, of the formula:

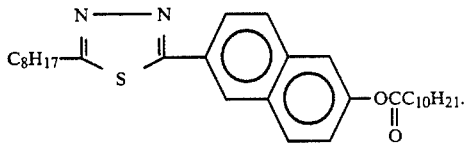

136. A compound according to claim 1, of the formula:

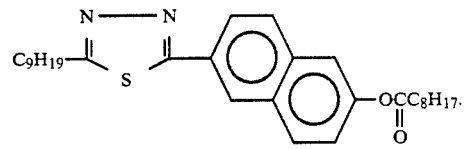

137. A compound according to claim 1, of the formula:

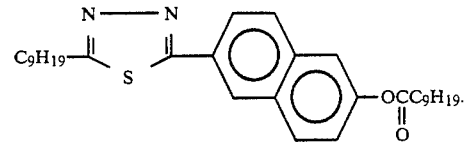

138. A compound according to claim 1, of the formula:

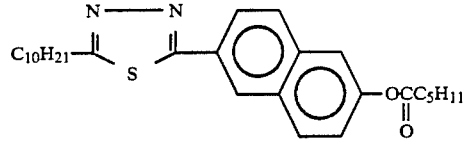

139. A compound according to claim 1, of the formula:

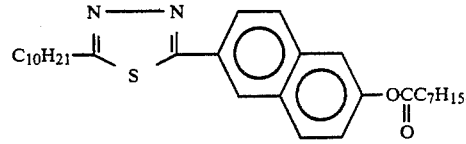

140. A compound according to claim 1, of the formula:

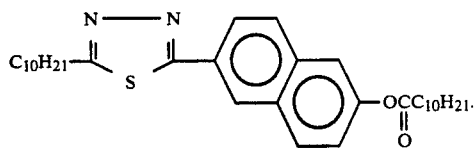

141. A compound according to claim 1, of the formula:

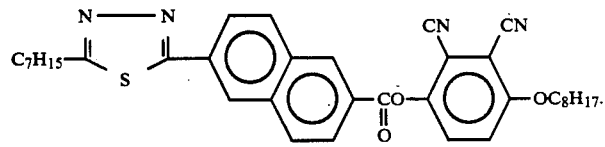

142. A compound according to claim 1, of the formula:

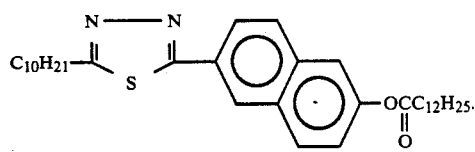

143. A compound according to claim 1, of the formula:

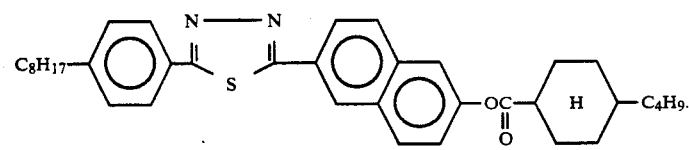

144. A compound according to claim 1, of the formula:

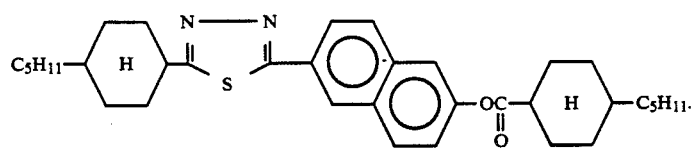

145. A compound according to claim 1, of the formula:

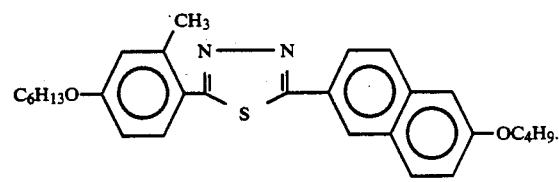

146. A compound according to claim 1, of the formula:

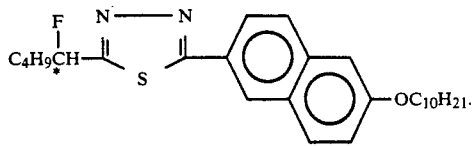

147. A compound according to claim 1, of the formula:

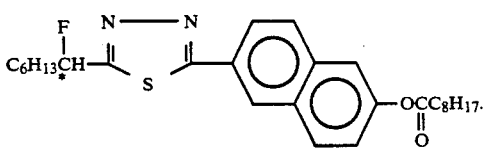

148. A compound according to claim 1, of the formula:

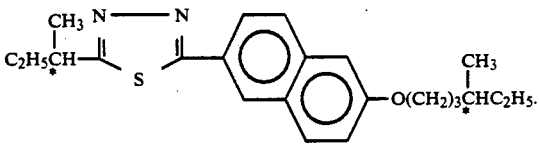

149. A compound according to claim 1, of the formula:

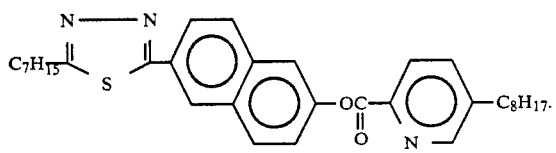

150. A compound according to claim 1, of the formula:

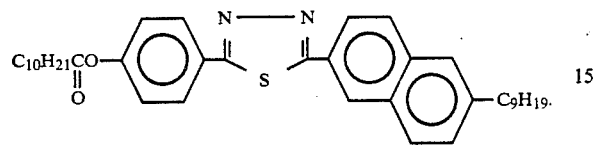

151. A compound according to claim 1, of the formula:

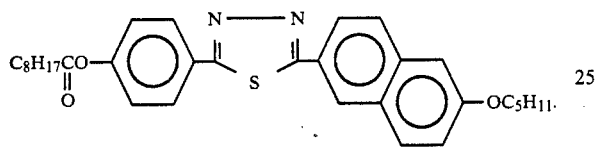

152. A compound according to claim 1, of the formula:

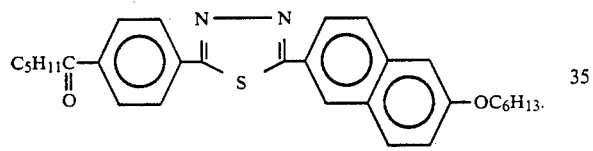

153. A compound according to claim 1, of the formula:

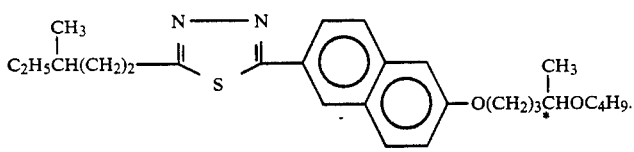

154. A compound according to claim 1, of the formula:

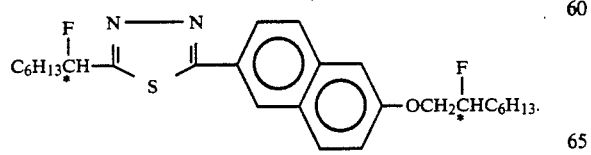

155. A compound according to claim 1, of the formula:

156. A compound according to claim 1, of the formula:

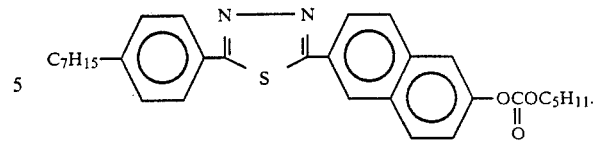

157. A compound according to claim 1, of the formula:

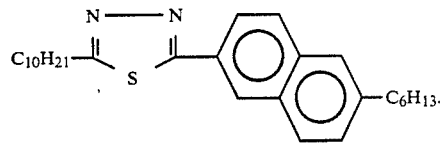

158. A compound according to claim 1, of the formula:

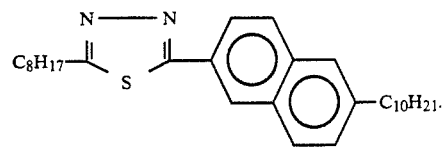

159. A compound according to claim 1, of the formula:

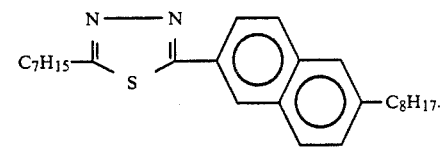

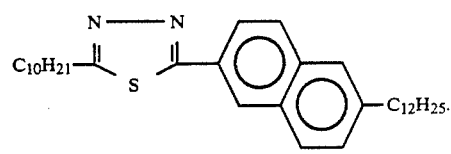

160. A compound according to claim 1, of the formula:

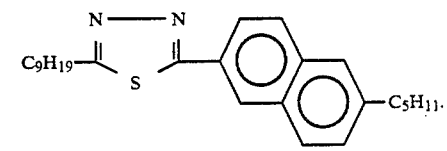

161. A compound according to claim 1, of the formula:

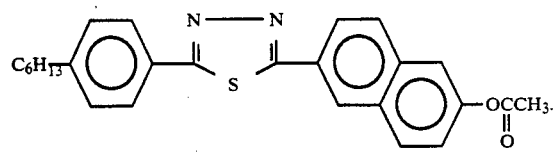

162. A compound according to claim 1, of the formula:

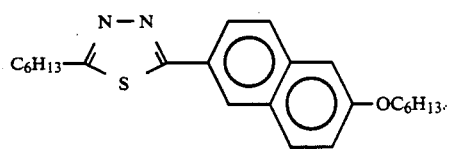

163. A compound according to claim 1, of the formula:

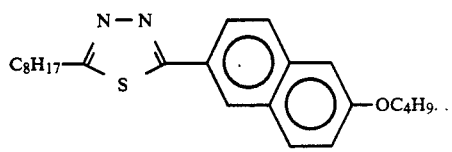

164. A compound according to claim 1, of the formula:

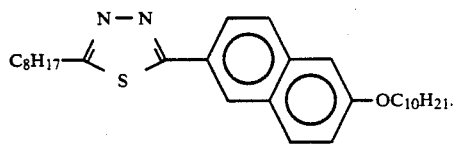

165. A compound according to claim 1, of the formula:

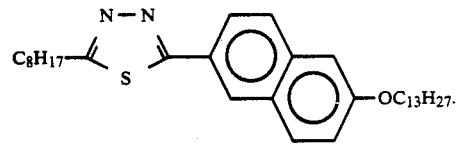

166. A compound according to claim 1, of the formula:

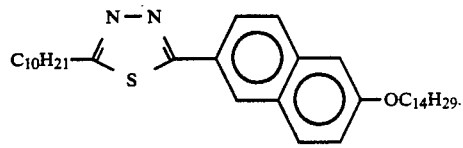

167. A compound according to claim 1, of the formula:

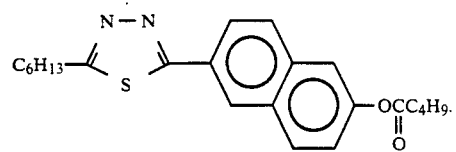

168. A compound according to claim 1, of the formula:

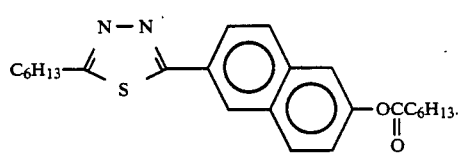

169. A compound according to claim 1, of the formula:

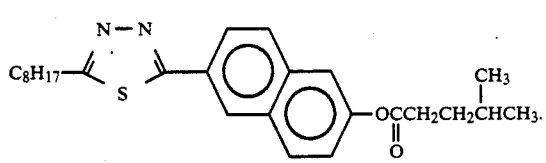

170. A compound according to claim 1, of the formula:

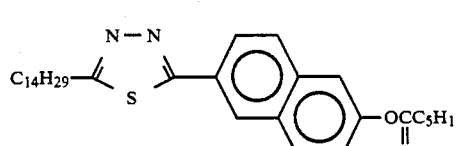

171. A compound according to claim 1, of the formula:

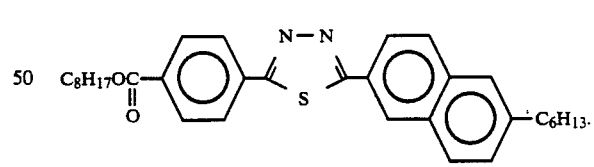

172. A compound according to claim 1, of the formula:

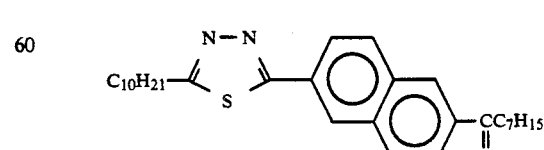

173. A compound according to claim 1, of the formula:

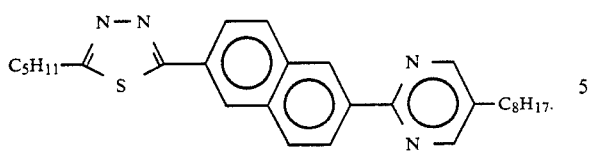  5

174. A liquid crystal composition comprising at least two mesomorphic compounds, at least one of which is a mesomorphic compound according to claim 1.

175. A liquid crystal composition according to claim 174, which comprises another mesomorphic compound other than that represented by the formula (I) and comprises 1-500 wt. parts of a mesomorphic compound of the formula (I) per 100 wt. parts of said another mesomorphic compound.

176. A liquid crystal device, comprising a pair of electrode plates and a liquid crystal composition according to claim 174 disposed between the electrode plates.

177. A liquid crystal composition according to claim 174, which comprises a chiral smectic phase.

178. A liquid crystal composition according to claim 174, wherein $X_1$ denotes any one of a single bond, —O— and

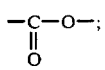

$X_2$ denotes any one of a single bond,

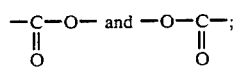

and
$X_3$ denotes any one of a single bond, —O—,

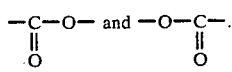

179. A liquid crystal composition according to claim 174, wherein $R_1$ and $R_2$ respectively denote any one of the following groups (i) to (iv);
(i) an n-alkyl group having 1-16 carbon atoms;

(ii)

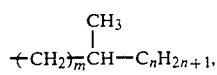

wherein m is an integer of 1-6 and n is an integer of 2-8;

(iii)

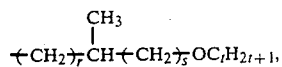

wherein r is an integer of 0-6, s is 0 or 1 and t is an integer of 1-12; and (iv)

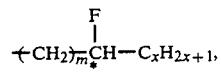

wherein m is 0 or 1 and x is an integer of 1-14.

180. A liquid crystal composition according to claim 179, wherein the group (i) is an n-alkyl group having 3-12 carbon atoms.

181. A liquid crystal composition according to claim 174, wherein $A_1$ denotes any one of

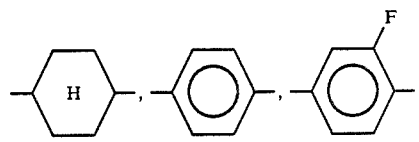

and a single bond; and
$A_2$ denotes any one of

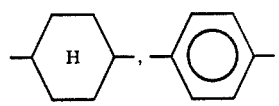

p1   and a single bond.

182. A liquid crystal composition comprising at least two mesomorphic compounds, at least one of said mesomorphic compounds being a mesomorphic compound represented by a formula selected from the group consisting of:

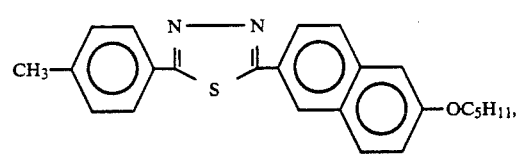

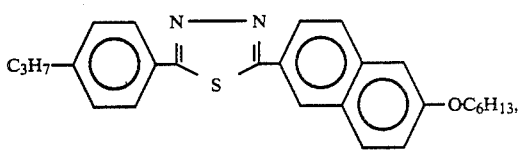

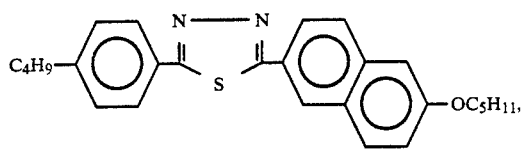

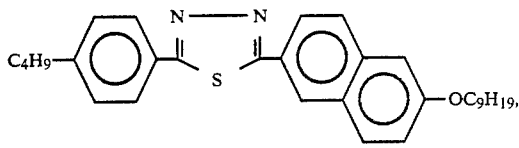

157
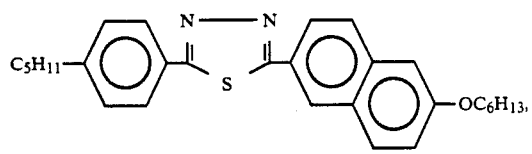
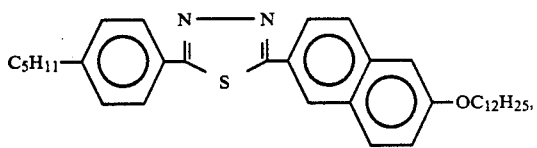
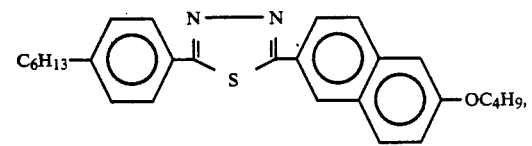
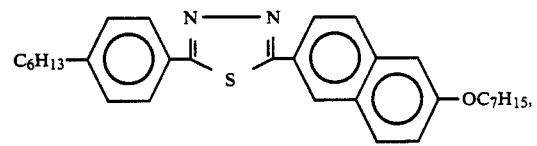
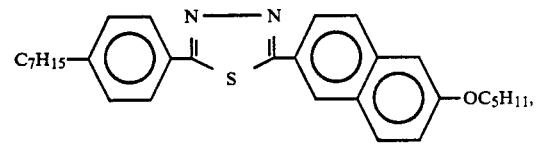
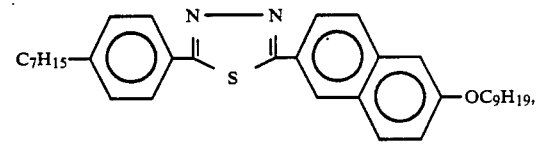
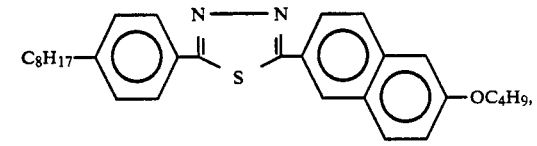
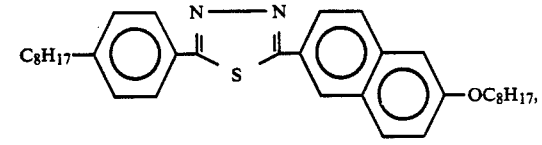
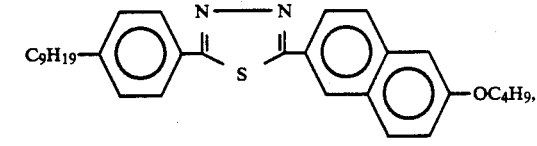
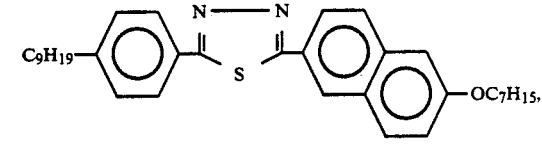
-continued
158
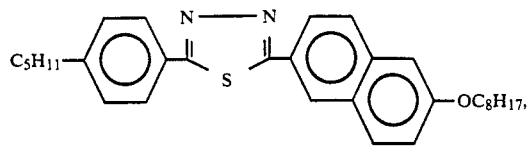
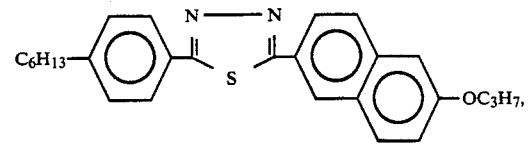
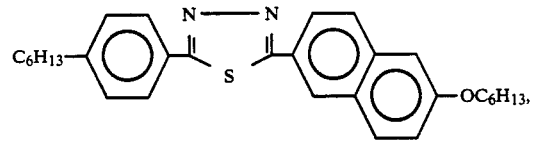
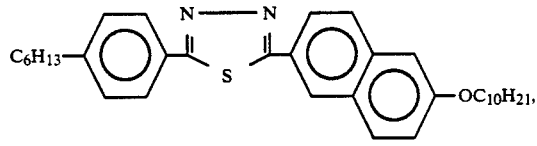
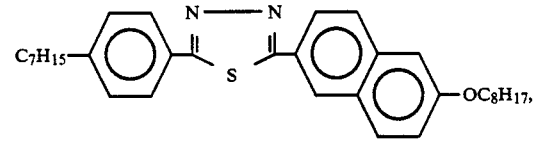
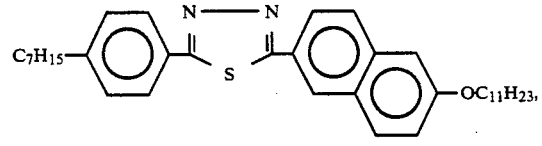
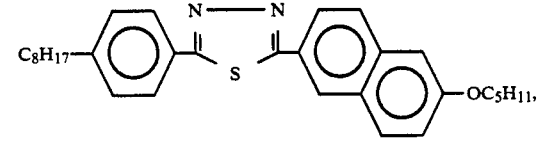
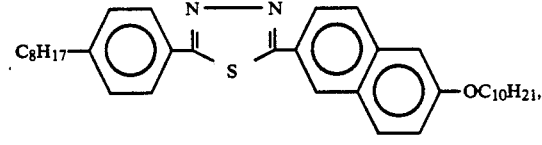
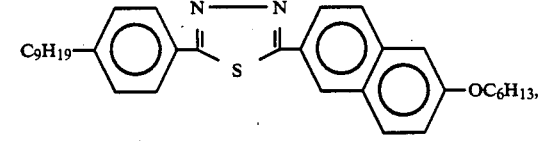
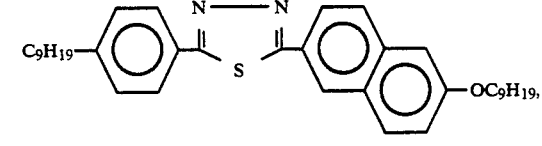

-continued
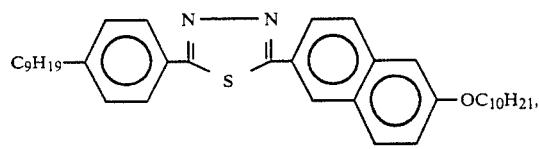
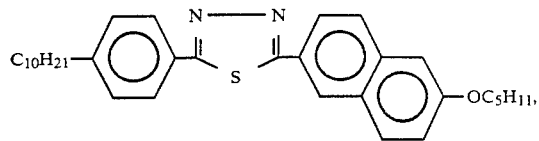
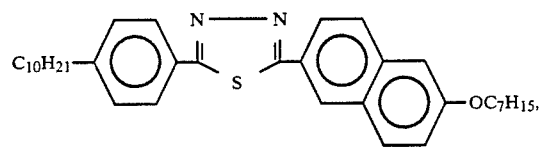
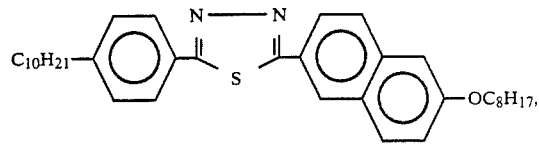
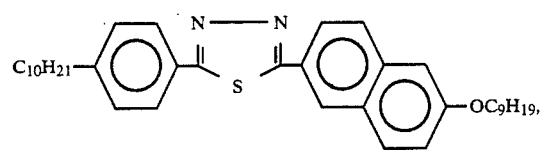
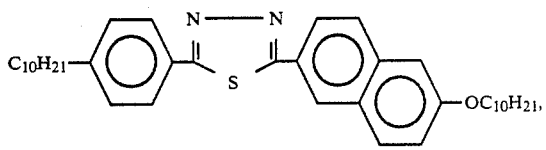
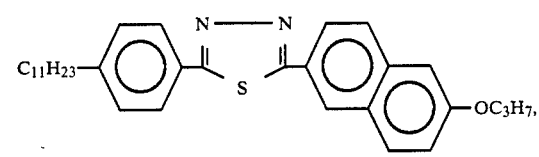
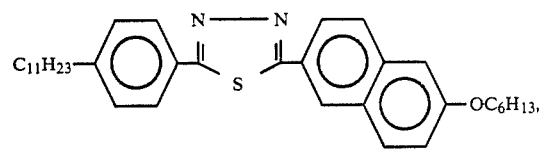
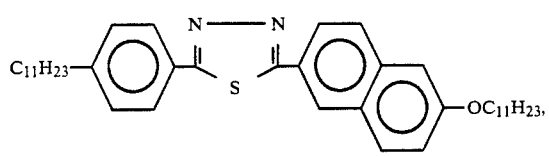
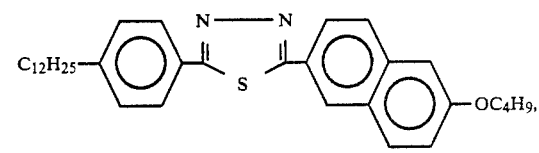
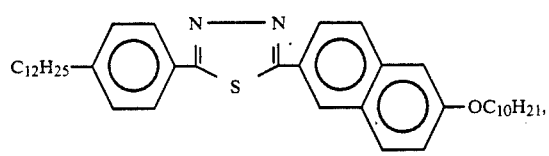
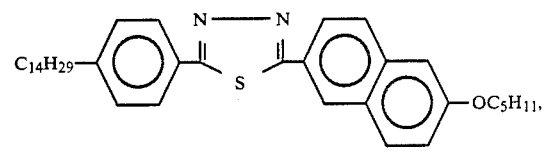
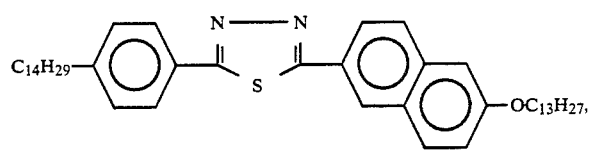
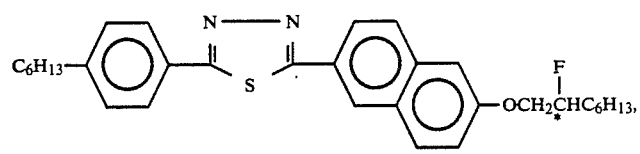
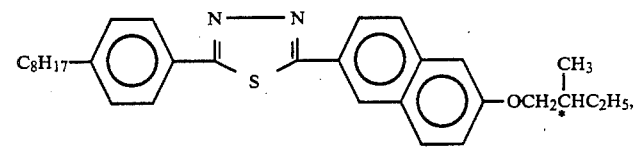
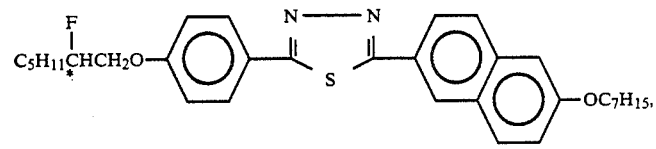

-continued
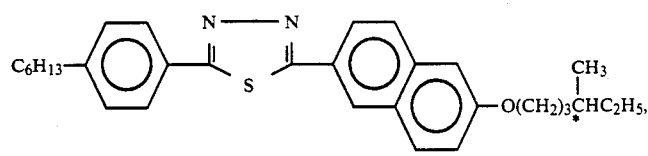
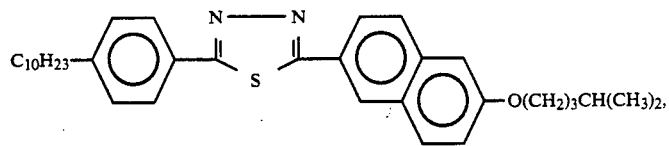
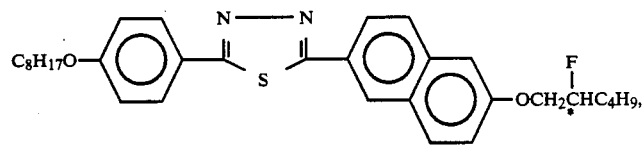
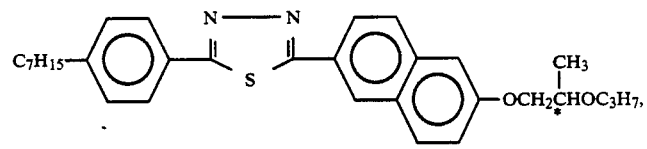
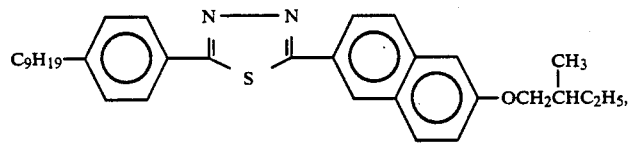
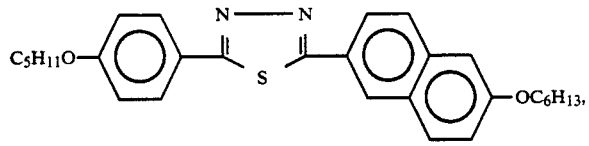
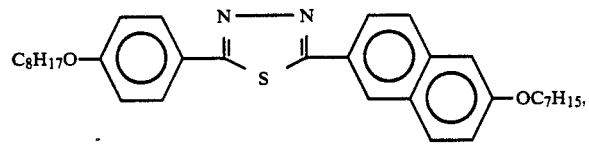
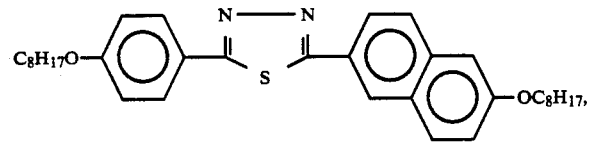
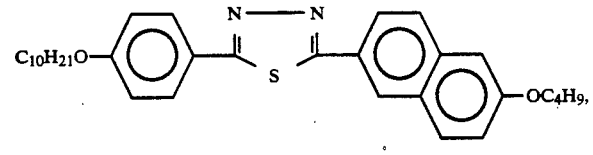
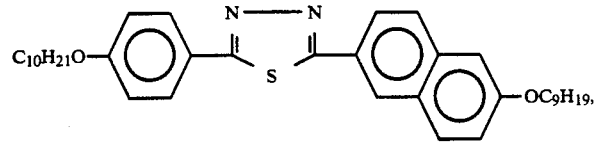

-continued
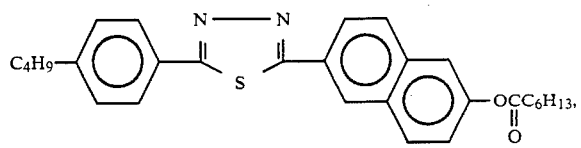
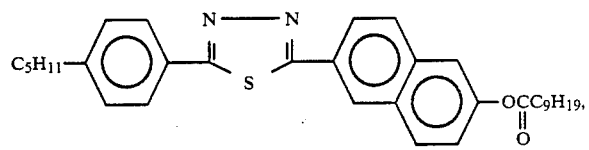
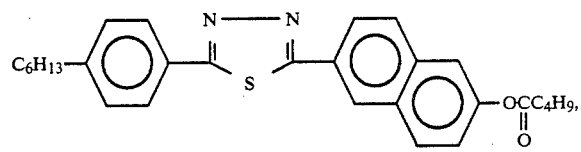
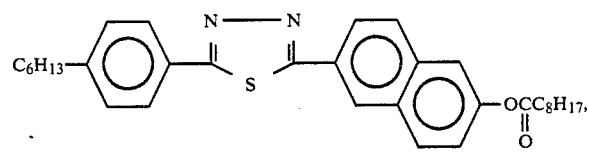
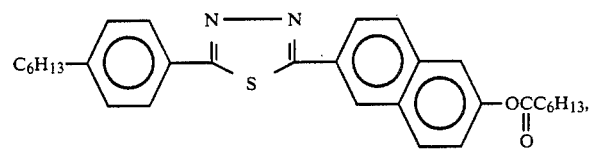
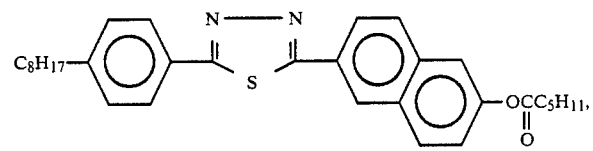
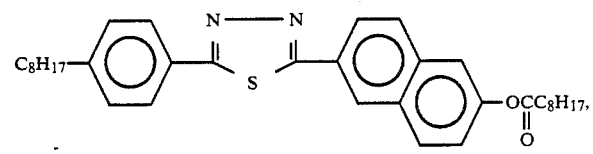
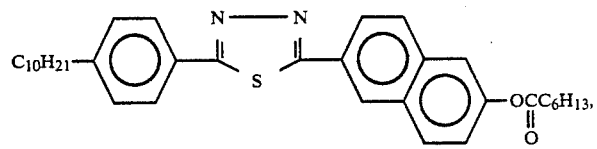
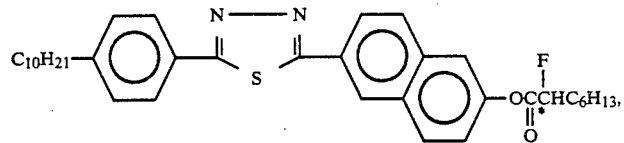
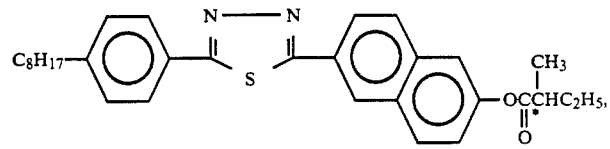

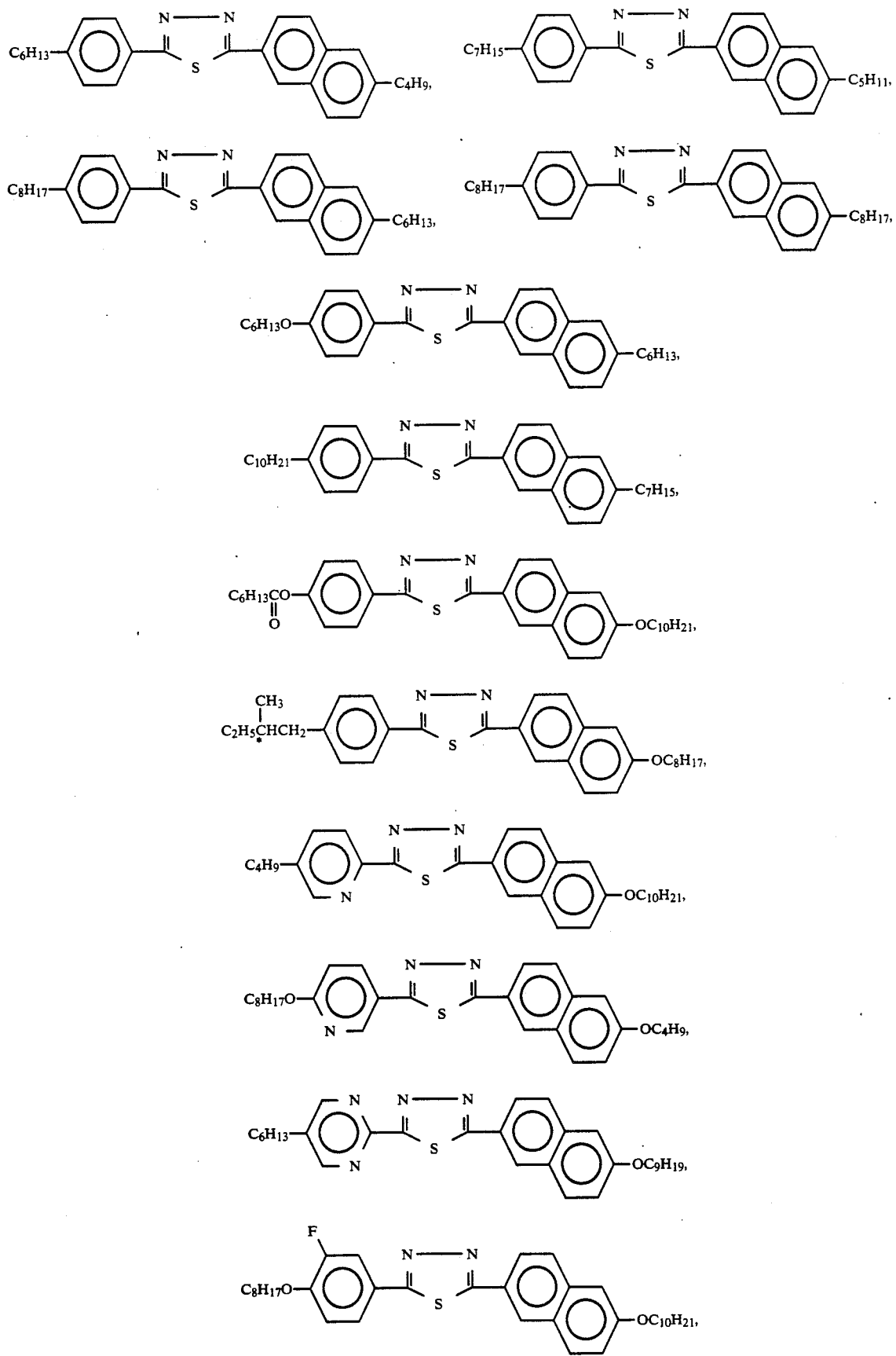

-continued
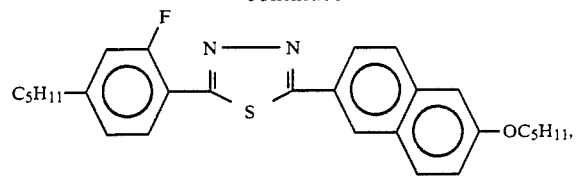
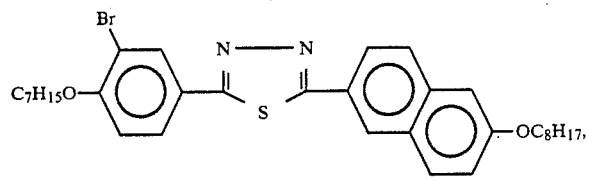
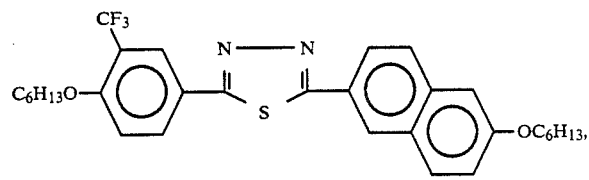
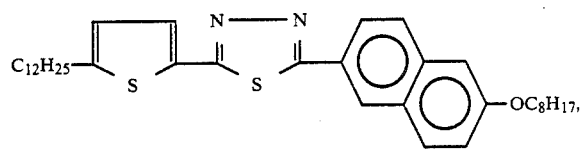
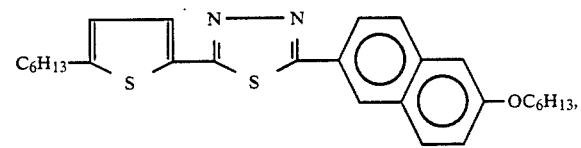
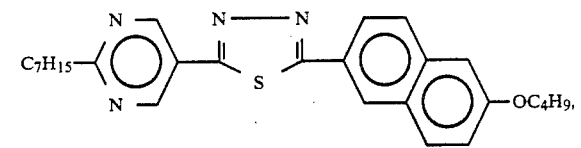
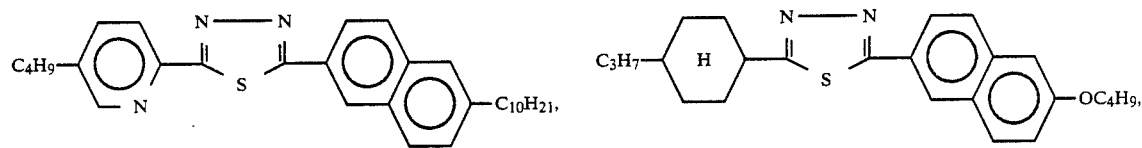
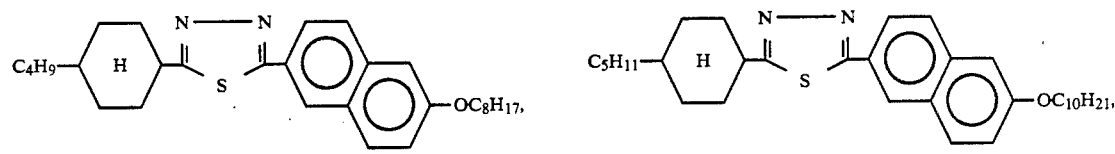
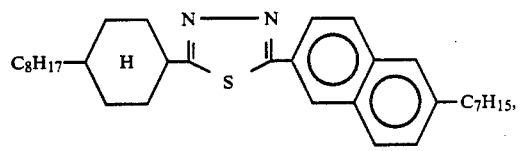
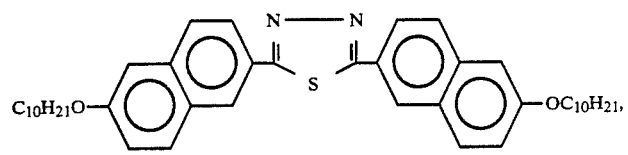

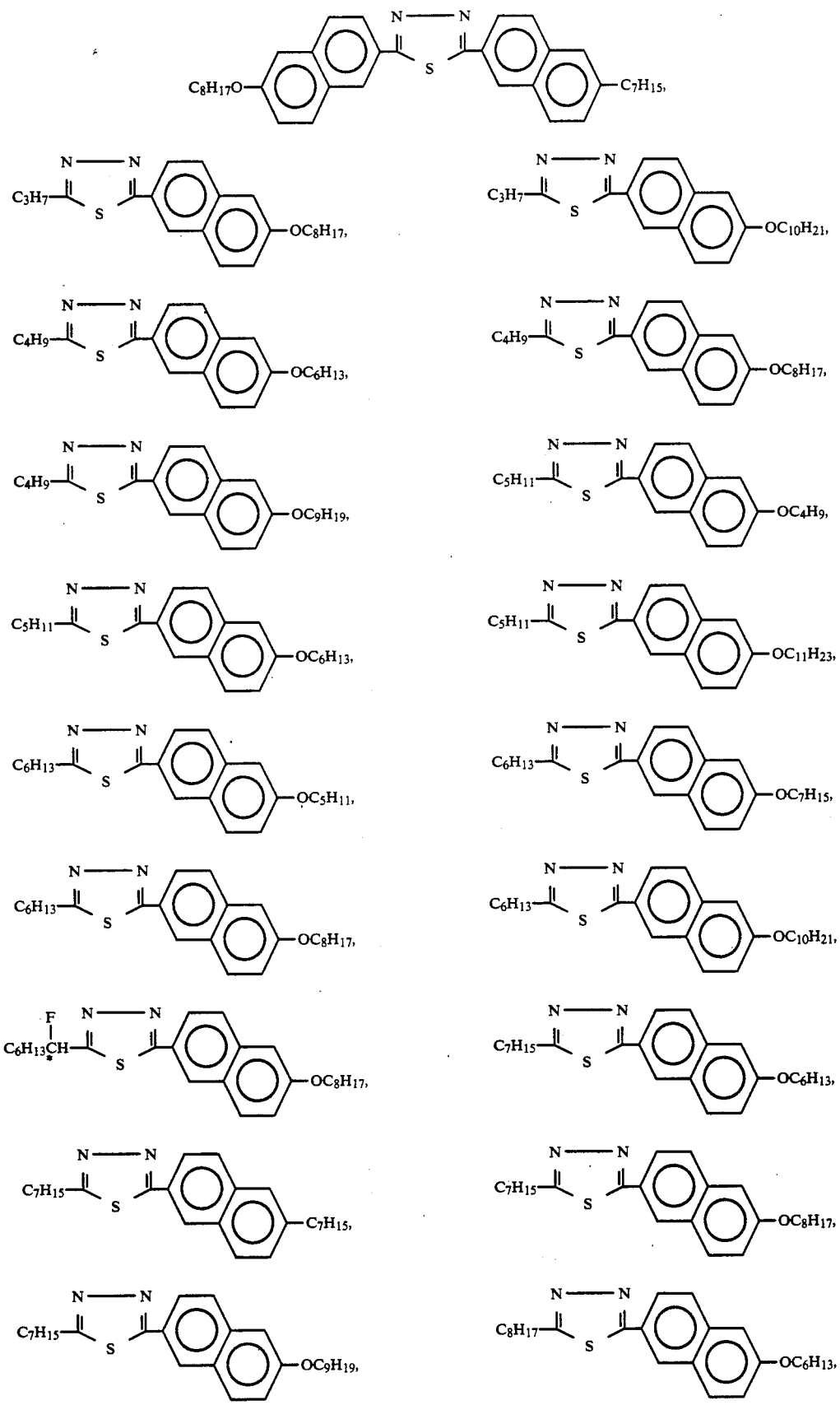

-continued
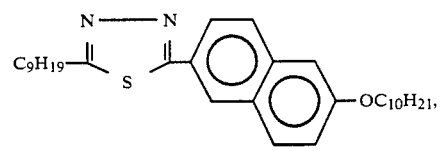
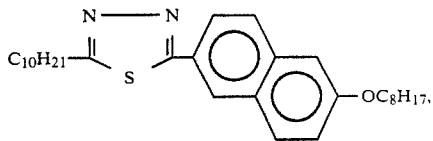
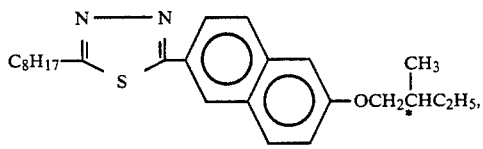
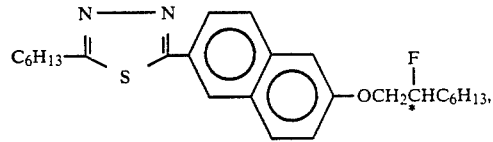
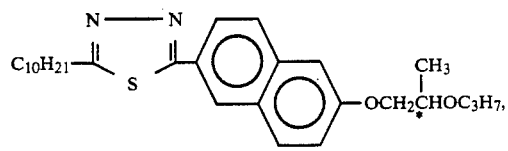
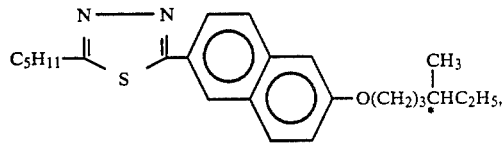
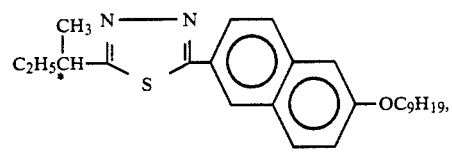
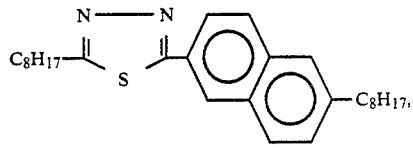
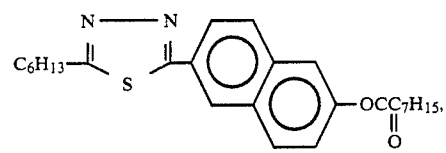
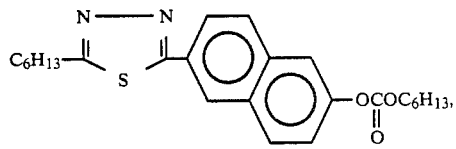
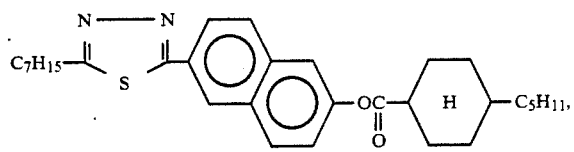
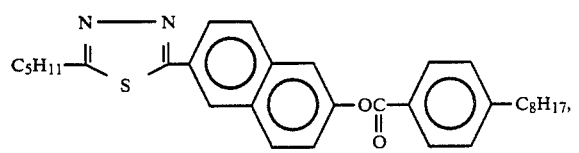
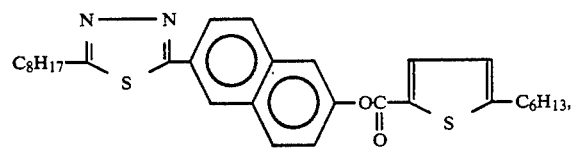
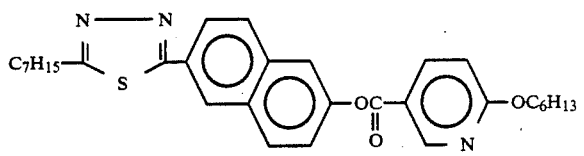
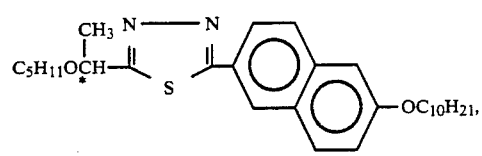
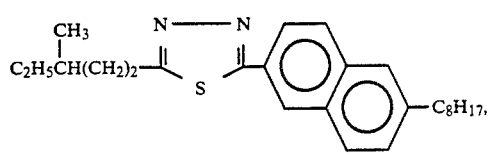

-continued
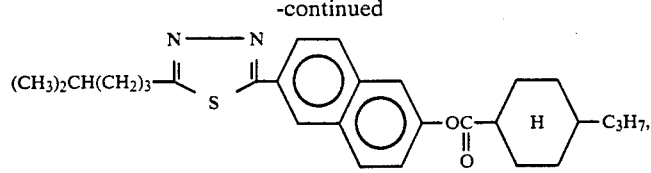
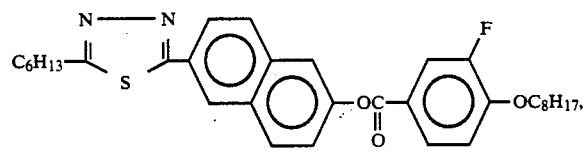
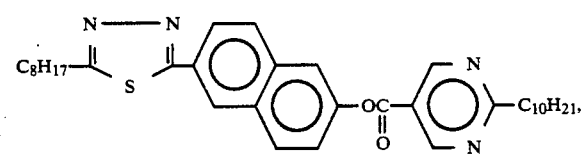
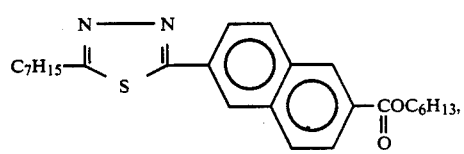
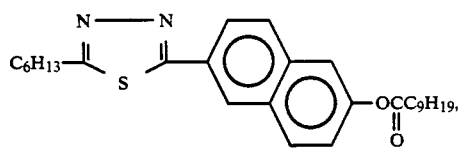
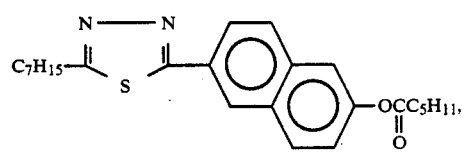
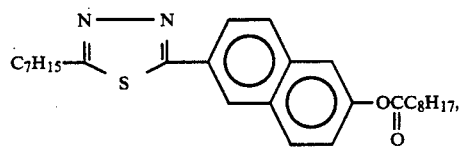
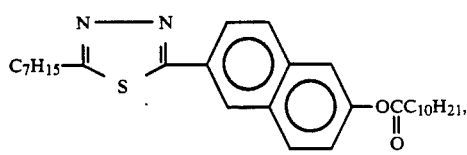
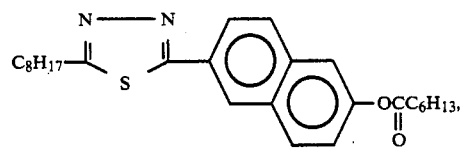
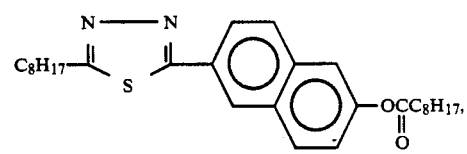
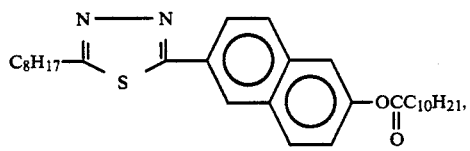
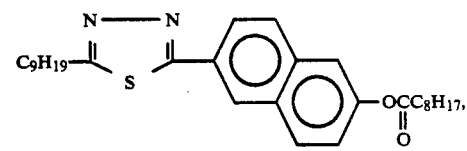
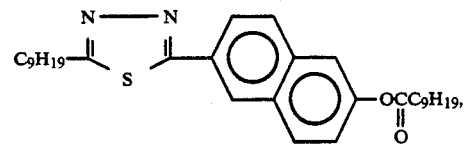
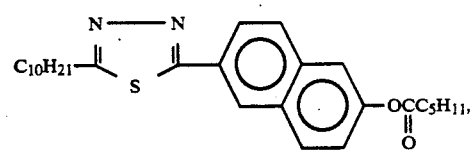
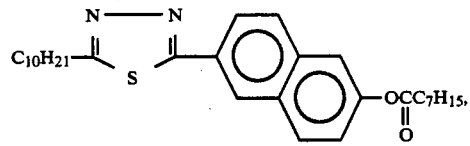
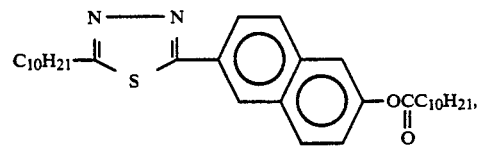

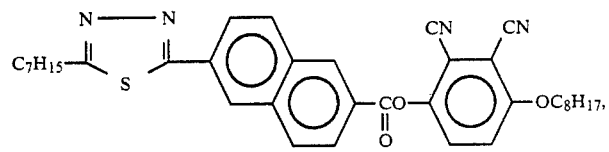
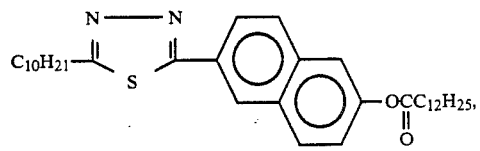
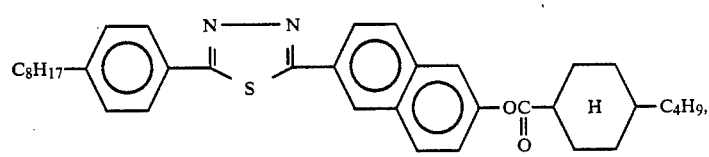
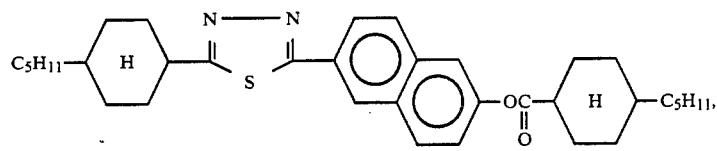
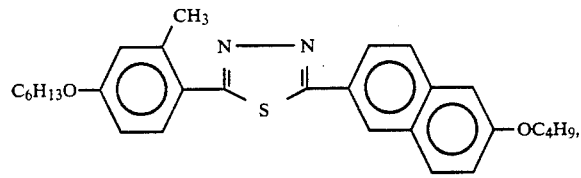
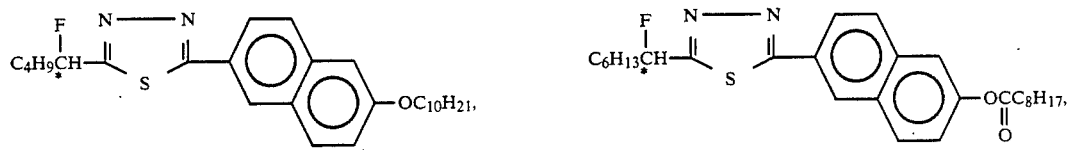
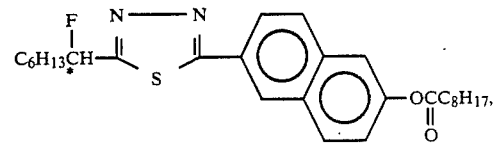
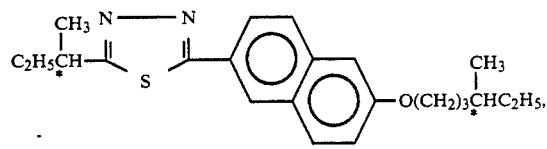
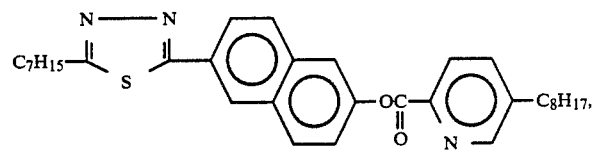
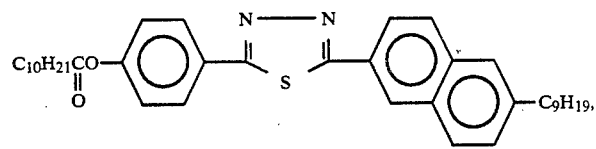
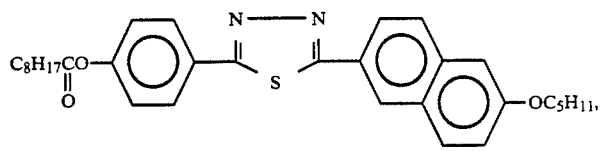

-continued
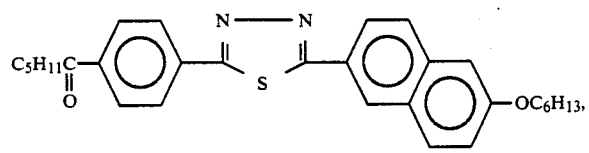
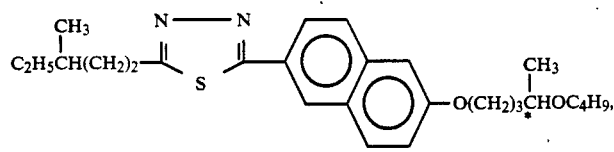
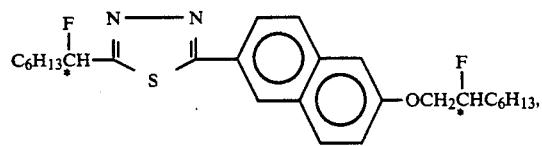
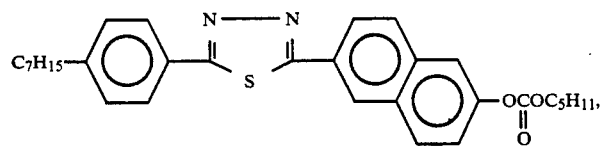
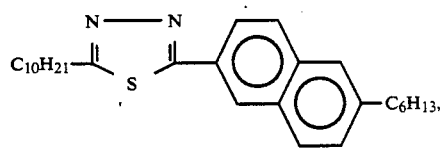
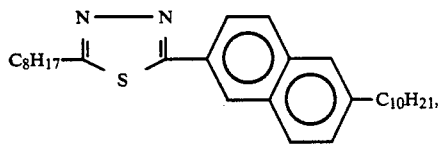
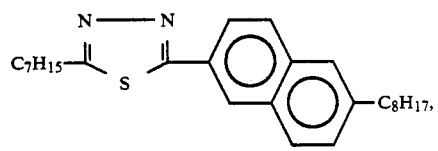
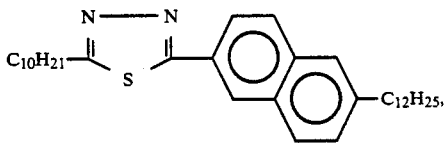
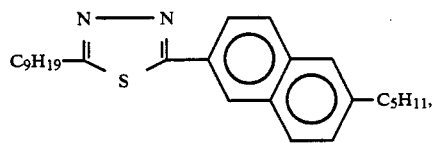
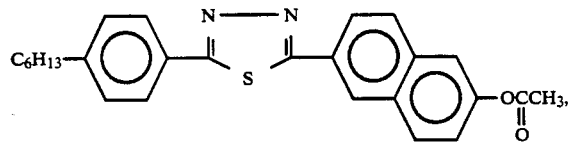
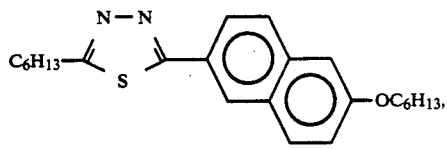
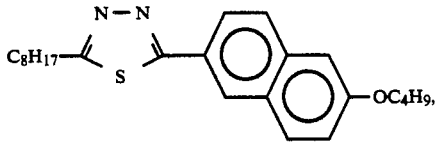
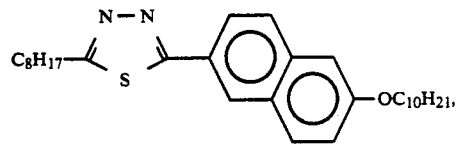
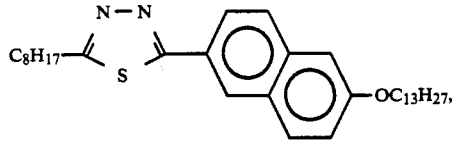

-continued

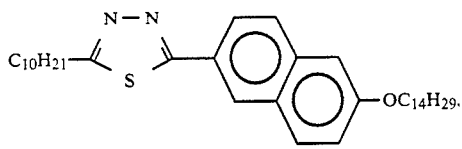

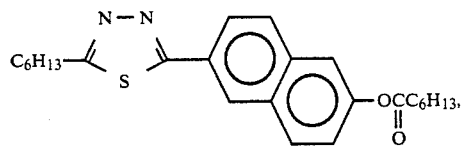

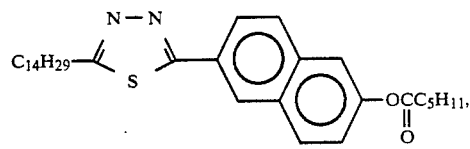

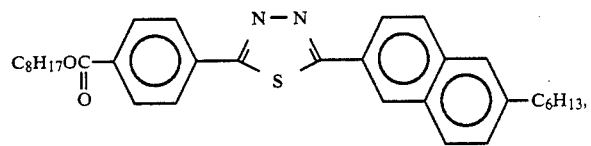

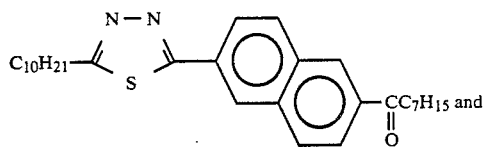

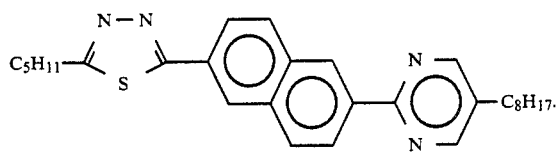

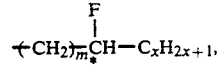

183. A liquid crystal device according to claim 176, wherein $X_1$ denotes any one of a single bond, —O— and

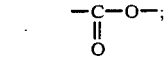

$X_2$ denotes any one of a single bond,

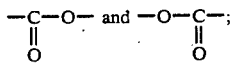

and $X_3$ denotes any one of a single bond, —O—,

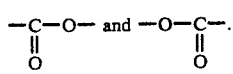

184. A liquid crystal device according to claim 176, wherein $R_1$ and $R_2$ respectively denote any one of the following groups (i) to (iv);
(i) an n-alkyl group having 1–16 carbon atoms;
(ii)

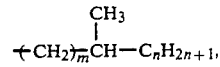

wherein m is an integer of 1–6 and n is an integer of 2–8;
(iii)

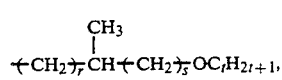

wherein r is an integer of 0–6, s is 0 or 1 and t is an integer of 1–12; and
(iv)

wherein m is 0 or 1 and x is an integer of 1–14.
185. A liquid crystal device according to claim 184, wherein the group (i) is an n-alkyl group having 3–12 carbon atoms.
186. A liquid crystal device according to claim 176, wherein $A_1$ denotes any one of

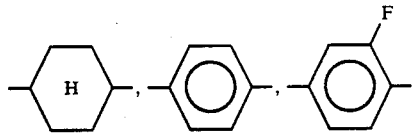

and a single bond; and

A₂ denotes any one of

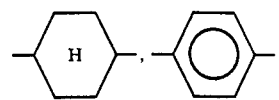

an a single bond.

187. A liquid crystal device comprising a pair of electrode plates and a liquid crystal composition according to claim 182 disposed between the electrode plates.

188. A liquid crystal device according to claim 176, which further comprises an insulating alignment control layer on the electrode plates.

189. A liquid crystal device according to claim 188, wherein the insulating alignment control layer has been subjected to rubbing.

* * * * *

United States Patent and Trademark Office

CERTIFICATE OF CORRECTION

PATENT NO. : 5,091,109
DATED : February 25, 1992
INVENTOR(S) : Takao Takiguchi, et al It is certified that error appears in the above-indentified patent and that said Letters Patent is hereby corrected as shown below:

On the title page:

IN [56] REFERENCES CITED

Under FOREIGN PATENT DOCUMENTS, insert:
-- 411906  11/1966  Switzerland
   426848   6/1967  Switzerland --.

IN [57] ABSTRACT

Line 7, "respectively" should read --respectively denote--.

COLUMN 1

Line 48, "so called" should read --so-called--.

COLUMN 7

Line 11, 

COLUMN 53

Formula (73), 

COLUMN 69

Formula (179), "$C_6H_{13}$" should read --$C_6H_{13}O$--.

COLUMN 79

Formula (225), "(225)" should read --(235)--.

UNITED STATES PATENT AND TRADEMARK OFFICE
CERTIFICATE OF CORRECTION

PATENT NO. : 5,091,109
DATED : February 25, 1992
INVENTOR(S) : Takao Takiguchi, et al It is certified that error appears in the above-indentified patent and that said Letters Patent is hereby corrected as shown below:

COLUMN 79

Formula (245), "$C_{10}H_{21}$--$OC_8H_{17}$" should read

--$C_{10}H_{21}$-(pyrazine ring)-(phenyl ring)-$OC_8H_{17}$--.

COLUMN 83

Line 7, "cf" should read --of--.

COLUMN 84

Line 13, "upper direction 34e" should read --upper direction 34a--.

COLUMN 90

Line 22, "was" should read --and--.
Line 35, "-5(6-" should read -- -5-(6- --.

COLUMN 93

Line 57, "15 second" should read --15 seconds--.

COLUMN 100

Line 11, "Examples" should read --Example--.

COLUMN 117

Line 41, "subjected" should read --subjected to--.

UNITED STATES PATENT AND TRADEMARK OFFICE
CERTIFICATE OF CORRECTION

PATENT NO. : 5,091,109
DATED : February 25, 1992
INVENTOR(S) : Takao Takiguchi, et al It is certified that error appears in the above-indentified patent and that said Letters Patent is hereby corrected as shown below:

COLUMN 119

Line 29, "subjected" should read --subjected to--.

COLUMN 120

Line 30, "3,23 g" should read --3.23 g--.
Line 40, "(acetoneethyl" should read --(acetone-ethyl--.

COLUMN 121

Line 41, "added" should read --added to--.

COLUMN 122

Line 64, "-O-," should be deleted.

COLUMN 123

Lines 57-60, "$-\overset{\overset{O}{\|}}{C}-O-;$" should read -- $-\underset{\underset{O}{\|}}{C}-O-;$ --.

Lines 63-65, "$-\overset{\overset{O}{\|}}{C}-O-$ and $-O-\overset{\overset{O}{\|}}{C}-;$"

should read -- $-\underset{\underset{O}{\|}}{C}-O-$ and $-O-\underset{\underset{O}{\|}}{C}-;$ --.

UNITED STATES PATENT AND TRADEMARK OFFICE
CERTIFICATE OF CORRECTION

PATENT NO. : 5,091,109
DATED : February 25, 1992
INVENTOR(S) : Takao Takiguchi, et al It is certified that error appears in the above-indentified patent and that said Letters Patent is hereby corrected as shown below:

COLUMN 124

Lines 1-5, "$-\underset{\underset{O}{\|}}{C}-O-$ and $-O-\underset{\underset{O}{\|}}{C}-$."

should read -- $-\underset{\underset{O}{\|}}{C}-O-$ and $-O-\underset{\underset{O}{\|}}{C}-$ --.

COLUMN 147

Line 5, "$C_7H_{16}$" should read --$C_7H_{15}$--.

COLUMN 182

Line 7, "an" should read --and--.

Signed and Sealed this

Third Day of August, 1993

Attest:

MICHAEL K. KIRK

*Attesting Officer*   *Acting Commissioner of Patents and Trademarks*